US009422560B2

(12) United States Patent
Feinstein

(10) Patent No.: US 9,422,560 B2
(45) Date of Patent: Aug. 23, 2016

(54) METHODS AND COMPOSITIONS FOR NEUROPROTECTION

(71) Applicant: QUARK PHARMACEUTICALS, INC., Fremont, CA (US)

(72) Inventor: Elena Feinstein, Rehovot (IL)

(73) Assignee: Quark Pharmaceuticals, Inc., Fremont, CA (US)

( * ) Notice: Subject to any disclaimer, the term of this patent is extended or adjusted under 35 U.S.C. 154(b) by 0 days.

(21) Appl. No.: 14/354,596

(22) PCT Filed: Nov. 1, 2012

(86) PCT No.: PCT/US2012/062894

§ 371 (c)(1),
(2) Date: Apr. 28, 2014

(87) PCT Pub. No.: WO2013/067076

PCT Pub. Date: May 10, 2013

(65) Prior Publication Data

US 2015/0031746 A1 Jan. 29, 2015

Related U.S. Application Data

(60) Provisional application No. 61/554,982, filed on Nov. 3, 2011, provisional application No. 61/663,627, filed on Jun. 25, 2012.

(51) Int. Cl.

| | |
|---|---|
| *A61K 48/00* | (2006.01) |
| *C12N 15/11* | (2006.01) |
| *C12N 15/113* | (2010.01) |
| *A61K 31/713* | (2006.01) |

(52) U.S. Cl.
CPC .......... *C12N 15/1137* (2013.01); *A61K 31/713* (2013.01); *C12N 15/113* (2013.01); *C12Y 304/22017* (2013.01); *C12Y 304/22055* (2013.01); *C12Y 306/03* (2013.01); *C12Y 306/05002* (2013.01); *C12N 2310/14* (2013.01); *C12N 2310/321* (2013.01); *C12N 2320/30* (2013.01); *C12N 2320/32* (2013.01)

(58) Field of Classification Search
USPC ........................................... 514/44; 536/24.5
See application file for complete search history.

(56) References Cited

U.S. PATENT DOCUMENTS

| | | | |
|---|---|---|---|
| 8,431,692 | B2 | 4/2013 | Alpert et al. |
| 9,089,591 | B2 | 7/2015 | Alpert et al. |
| 2008/0108583 | A1 | 5/2008 | Feinstein |
| 2011/0142917 | A1 | 6/2011 | Alpert et al. |
| 2011/0229557 | A1 | 9/2011 | Feinstein et al. |

FOREIGN PATENT DOCUMENTS

| | | |
|---|---|---|
| WO | WO 2009/044392 | 4/2009 |
| WO | WO 2011/072091 | 6/2011 |

OTHER PUBLICATIONS

Debashree Makherjea et al. "Transtympanic Administration of Short Interfering (si) RNA for NOX3 Isoform of NADPH Oxidase Protects Against Cisplatin-Induced Hearing Loss in the Rat", Antioxidant &Redox Signaling, vol. 13, Sep. 2010, pp. 589-598.

*Primary Examiner* — Terra C Gibbs
(74) *Attorney, Agent, or Firm* — Fish & Richardson P.C.

(57) ABSTRACT

Disclosed herein are methods and kits useful for providing neuroprotection to neurons in the inner ear and to methods of treating inner ear diseases and disorders, including tinnitus and Mnire's disease.

14 Claims, 10 Drawing Sheets

Vehicle treated
siCASP2 treated

Cochlea X10

Spiral ganglion X63

Vestibular ganglion X40

SEQUENCE LISTING

```
<160> NUMBER OF SEQ ID NOS: 27

<210> SEQ ID NO 1
<211> LENGTH: 4241
<212> TYPE: RNA
<213> ORGANISM: Homo sapiens

<400> SEQUENCE: 1

uuuugucugu ccgccgagca ccccacuuca ccccauugga ccgcgcggcc gccgcuagag     60

cucugcgccu gcgcacgcac cgggccgggg acugggugge cuggugugug ggcgcggcag    120

ggcgcaggcg caggcgcagu gugcguccgc gucugagggg agggaugugg gggaagcgac    180

ggcccccggu uuguuugggc ugugggcggu gcgcagcgga gagcccggga aaagcgggaa    240

auggcggcgc cgagcgcggg gucuuggucc accuuccagc acaaggagcu gauggccgcu    300

gacaggggac gcaggauauu gggagugugu ggcaugcauc cucaucauca ggaaacucua    360

aaaaagaacc gaguggugcu agccaaacag cuguuguuga gcgaauuguu agaacaucuu    420

cuggagaagg acaucaucac cuuggaaaug agggagcuca uccaggccaa agugggcagu    480

uucagccaga auguggaacu ccucaacuug cugccuaaga ggggucccca agcuuuugau    540

gccuucugug aagcacugag ggagaccaag caaggccacc uggaggauau guugcucacc    600

acccuuucug ggcuucagca uguacuccca ccguugagcu gugacuacga cuugagucuc    660

ccuuuuccgg ugugugaguc cuguccccuu uacaagaagc uccgccuguc gacagauacu    720

guggaacacu cccuagacaa uaaagauggu ccugucugcc uucaggugaa gccuugcacu    780

ccugaauuuu aucaaacaca cuuccagcug gcauauaggu ugcagucucg gccucguggc    840

cuagcacugg uguugagcaa ugugcacuuc acuggagaga aagaacugga auuucgcucu    900

ggagggggaug uggaccacag uacucuaguc acccucuuca agcuuuuggg cuaugacguc    960

cauguucuau gugaccagac ugcacaggaa augcaagaga aacugcagaa uuuugcacag   1020

uuaccugcac accgagucac ggacuccugc aucguggcac uccucucgca uggugugggag   1080

ggcgccaucu auggugugga ugggaaacug cuccagcucc aagagguuuu ucagcucuuu   1140
```

-continued

```
gacaacgcca acugcccaag ccuacagaac aaaccaaaaa uguucuucau ccaggccugc   1200
cguggagaug agacugaucg uggggguugac caacaagaug gaaagaacca cgcaggaucc   1260
ccugggugcg aggagaguga ugccgguaaa gaaaaguugc cgaagaugag acugcccacg   1320
cgcucagaca ugauaugcgg cuaugccugc cucaaaggga cugccgccau gcggaacacc   1380
aaacgagguu ccugguacau cgaggcucuu gcucaagugu uucugagcgg ggcuugugau   1440
augcacgugg ccgacaugcu gguuaaggug aacgcacuua ucaaggaucg ggaagguuau   1500
gcuccuggca cagaauucca ccggugcaag gagaugucug aauacugcag cacucugugc   1560
cgccaccucu accuguuccc aggacacccu cccacaugau gucaccuccc caucauccac   1620
gccaagugga agccacugga ccacaggagg ugugauagag ccuuugaucu ucaggaugca   1680
cgguuucugu ucugccccccu cagggaugug ggaaucuccc agacuuguuu ccugugccca   1740
ucaucucugc cuuugagugu gggacuccag gccagcuccu uuucugugaa gcccuuugcc   1800
uguagagcca gccuugguug gaccuauugc caggaauguu ucagcugcag uugaagagcc   1860
ugacaaguga aguuguaaac acagugugu uaugggggaga gggcauauaa auuccccaua   1920
uuuguguuca guuccagcuu uuguagaugg cacuuuagug auugcuuuua uuacauuagu   1980
uaagaugucu gagagaccau cuccuaucuu uuauuucauu cauauccucc gcccuuuuug   2040
uccuagagug agaguuugga agguguccaa auuuaaugua gacauuaucu uuuggcucug   2100
aagaagcaaa caugacuaga gacgcaccuu gcugcagugu ccagaagcgg ccugugcguu   2160
cccuucagua cugcagcgcc acccagugga aggacacucu uggcucguuu gggcucaagg   2220
caccgcagcc ugucagccaa cauugccuug cauuuguacc uuauugaucu uugcccaugg   2280
aagucucaaa gaucuuucgu ugguuguuuc ucugagcuuu guuacugaaa ugagccucgu   2340
ggggagcauc agagaaggcc aggaagaaug guguguuucc cuagacucug uaaccaccuc   2400
ucugucuuuu uccuuccuga gaaacgucca ucucucuccc uuacuauucc cacuuucauu   2460
caaucaaccu gcacuucaua ucuagauuuc uagaaaagcu uccuagcuua ucucccugcu   2520
ucauaucucu cccuucuuua ccuucauuuc auccuguugg cugcugccac caaaucuguc   2580
uagaauccug cuuuacagga ucauguaaau gcucaaagau guaauguagu ucuuuguucc   2640
ugcuuucucu uucaguauua aacucuccuu ugauauuaug uggcuuuuau uucagugcca   2700
uacauguuau uguuuucaac cuagaaaccu uuaucccugc uuaucugaaa cuucccaacu   2760
ucccuguucu uuaagacuuu uuuuuuuuuu uuuuuuuuuu uugagacaga gucucgcucu   2820
gucgcccagg cuggagggca guggcacgau cucagcucac ugcaagcucc aacuccccggg   2880
uucacgccau ucuccugccu cagccuucca aguagcuggg acuacaggug cccgccaccg   2940
ugcccggcua auuuuuuugu auuuuuagua gagacagggu uucaccaugu uagccgggau   3000
ggucuugauc uccugaccuc augauccacc caccucagcc ucccaaagug uugggauuac   3060
aggcgugagc cacugcgccc gggcaagacc uuuuuuuaaa aaaaaaaaaa aaaaaacuuc   3120
cauucuuucu uccuccaguc uguucucaca uaacagagua guuuugguuu uuaauuuuuu   3180
uugguuguuu gcuguuuuuu guuuuuuaag gugaguucuc acuauguuuc ucagacuggu   3240
cucgaacucc uggccucaag ccaucuuccc gccucagccu cucaaauagc ugggcuuaca   3300
ggcaugagcc accacaccug gccaggauuu gguuguuuaa auauaaaucu gaucaccccc   3360
cugcuuagaa cccuucugcu uucuauuacc ccucauuuaa aauguaaacu cuucaccuug   3420
guuuaugaga acugguucuu gccuuccccu ugaaccucau uaaaugguga uuucuugcua   3480
agcuccagcc cgaguggucu ccucucagcu ucuaauuuug ugcucuuucc ugcccuuuuc   3540
```

cugggccuuc ucagcucucc acccccacca cucuugacuc agguggugucc cuucuuccuc 3600 aagucuugac aauucccggg cccuucaguc ccugagcagu cuacuucugu gucugucacc 3660
acaucuuguc uuuuccccuc auugcauuua uugcaguuua uauauaugcu acuuuuacuu 3720
guucauuucu gucuccccua ccaggcugua aaugagggca gaaaccuugu uuguuuuauu 3780
caccaucaug uaccaagugc uuggcacaua gugggccuuc auuaaauguu uguugaauaa 3840
aagagggaag aaggcaagcc aaccuuagcu acaauccuac cuuuugauaa aauguuccuu 3900
uugacaauau acacggauua uuauuuguac uuuguuuuuc cauguguuuu gcuuuuaucc 3960
acuggcauuu uuagcuccuu gaagacauau caugugugag auaacuuccu ucacaucucc 4020
caugguccuu agcaaaaugc uaggccugua guagucaagg ugcucaauaa auauuuguuu 4080 ggguggguuug ugagccuugc ugccaagucc ugccuuuggg ucgacauagu auggaaguau 4140
uugagagaga gaaccuuucc acucccacug ccaggauuuu guauugccau cgggugccaa 4200 auaaaaugcuc auauuuauua cugaaaaaaa aaaaaaaaaa a 4241

<210> SEQ ID NO 2
<211> LENGTH: 4023
<212> TYPE: RNA
<213> ORGANISM: Homo sapiens

<400> SEQUENCE: 2
uuuugucugu ccgccgagca ccccacuuca ccccauugga ccgcgcggcc gccgcuagag 60
cucugcgccu gcgcacgcac cgggccgggg acugggguggc cuggugugug ggcgcggcag 120
ggcgcaggcg caggcgcagu gugcguccgc gucugagggg agggaugugg gggaagcgac 180
ggcccccggu uuguuugggc ugugggcggu gcgcagcgga gagcccggga aaagcgggaa 240
auggcggcgc cgagcgcggg gucuugguccc accuuccagc acaaggagcu gauggccgcu 300
gacaggggac gcaggauauu gggagugugu ggcaugcauc cucaucauca ggaaacucua 360
aaaaagaacc gaguggugcu agccaaacag cuguuguuga gcgaauuguu agaacaucuu 420
cuggagaagg acaucaucac cuuggaaaug agggagcuca uccaggccaa agugggcagu 480
uucagccaga auguggaacu ccucaacuug cugccuaaga ggggucccca agcuuuugau 540
gccuucugug aagccuugca cuccugaauu uuaucaaaca cacuuccagc uggcauauag 600
guugcagucu cggccucgug gccuagcacu gguguugagc aaugugcacu ucacuggaga 660
gaaagaacug gaauuucgcu cuggaggggga uguggaccac aguacucuag ucacccucuu 720
caagcuuuug ggcuaugacg uccauguucu augugaccag acugcacagg aaaugcaaga 780
gaaacugcag aauuuugcac aguuaccugc acaccgaguc acggacuccu gcaucguggc 840
acuccucucg cauggugugg agggcgccau cuauggugug gaugggaaac ugcuccagcu 900
ccaagagguu uuucagcucu uugacaacgc caacugccca agccuacaga acaaaccaaa 960
aauguucuuc auccaggccu gccguggaga ugagacugau cguggggguug accaacaaga 1020 uggaaagaac cacgcaggau ccccugggug cgaggagagu gaugccggua aagaaaaguu 1080
gccgaagaug agacugccca cgcgcucaga caugauaugc ggcuaugccu gccucaaagg 1140
gacugccgcc augcggaaca ccaaacgagg uuccugguac aucgaggcuc uugcucaagu 1200
guuuucugag cgggcuugug auaugcacgu ggccgacaug cugguuaagg ugaacgcacu 1260
uaucaaggau cgggaagguu augcuccugg cacagaauuc caccggugca aggagauguc 1320
ugaauacugc agcacucugu gccgccaccu cuaccuguuc ccaggacacc cucccacaug 1380
augucaccuc cccaucaucc acgccaagug gaagccacug gaccacagga ggugugauag 1440

-continued agccuuugau cuucaggaug cacgguuucu guucugcccc cucagggaug ugggaaucuc 1500
ccagacuugu uuccugugcc caucaucucu gccuuugagu gugggacucc aggccagcuc 1560
cuuuucugug aagcccuuug ccuguagagc cagccuuggu uggaccuauu gccaggaaug 1620
uuucagcugc aguugaagag ccugacaagu gaaguuguaa acacagugug guuauggga 1680 gagggcauau aaauucccca uauuuguguu caguuccagc uuuuguagau ggcacuuuag 1740
ugauugcuuu uauuacauua guuaagaugu cugagagacc aucuccuauc uuuuauuuca 1800
uucauauccu ccgcccuuuu uguccuagag ugagaguuug gaaggugucc aaauuuaaug 1860
uagacauuau cuuuuggcuc ugaagaagca aacaugacua gagacgcacc uugcugcagu 1920
guccagaagc ggccugugcg uucccuucag uacugcagcg ccacccagug gaaggacacu 1980
cuuggcucgu uugggcucaa ggcaccgcag ccugucagcc aacauugccu ugcauuugua 2040
ccuuauugau cuuugcccau ggaagucuca aagaucuuuc guugguuguu ucucugagcu 2100
uuguuacuga aaugagccuc guggggagca ucagagaagg ccaggaagaa uggugugguu 2160
cccuagacuc uguaaccacc ucucugucuu uuuccuuccu gagaaacguc caucucucuc 2220
ccuuacuauu cccacuuuca uucaaucaac cugcacuuca uaucuagauu ucuagaaaag 2280
cuuccuagcu uaucucccug cuucauaucu cucccuucuu uaccuucauu ucauccuguu 2340
ggcugcugcc accaaaucug ucuagaaucc ugcuuuacag gaucauguaa augcucaaag 2400
auguaaugua guucuuuguu ccugcuuucu cuuucaguau uaaacucucc uuugauauua 2460
uguggcuuuu auuucagugc cauacauguu auuguuuuca accuagaaac cuuuaucccu 2520
gcuuaucuga aacuucccaa cuucccuguu cuuuaagacu uuuuuuuuuu uuuuuuuuuu 2580
uuuugagaca gagucucgcu cugucgccca ggcuggaggg caguggcacg aucucagcuc 2640
acugcaagcu ccaacucccg gguucacgcc auucuccugc cucagccuuc caaguagcug 2700
ggacuacagg ugcccgccac cgugcccggc uaauuuuuuu guauuuuuag uagagacagg 2760
guuucaccau guuagccggg augguucuuga ucuccugacc ucaugaucca cccaccucag 2820
ccucccaaag uguugggauu acaggcguga gccacugcgc ccgggcaaga ccuuuuuuua 2880
aaaaaaaaaa aaaaaaaacu uccauucuuu cuuccuccag ucuguucuca cauaacagag 2940
uaguuuuggu uuuuaauuuu uuuugguugu uugcuguuuu uuguuuuuua aggugaguuc 3000
ucacuauguu ucucagacug gucucgaacu ccuggccuca agccaucuuc ccgccucagc 3060
cucucaaaua gcugggcuua caggcaugag ccaccacacc uggccaggau uugguuguuu 3120
aaauauaaau cugaucaccc cccugcuuag aacccuucug cuuucuauua ccccucauuu 3180
aaaauguaaa cucuucaccu ugguuuauga gaacugguuc uugccuuccc cuugaaccuc 3240
auuaaauggu gauuucuugc uaagcuccag cccgaguggu cuccucucag cuucuaauuu 3300
ugugcucuuu ccugcccuuu uccugggccu ucucagcucu ccaccccccac cacucuugac 3360 ucagguggug uccuucuucc ucaagucuug acaauucccg ggcccuucag ucccugagca 3420
gucuacuucu gugucuguca ccacaucuug ucuuuucccc ucauugcauu uauugcaguu 3480
uauauauaug cuacuuuuac uuguucauuu cugucucccc uaccaggcug uaaaugaggg 3540
cagaaaccuu guuuguuuua uucaccauca uguaccaagu gcuuggcaca uagugggccu 3600
ucauuaaaug uuuguugaau aaaagaggga agaaggcaag ccaaccuuag cuacaauccu 3660
accuuuugau aaaauguucc uuuugacaau auacacggau uauuauuugu acuuuguuuu 3720
uccauguguu uugcuuuuau ccacuggcau uuuuagcucc uugaagacau aucaugugug 3780
agauaacuuc cuucacaucu cccauggucc cuagcaaaau gcuaggccug uaguagucaa 3840
ggugcucaau aaauauuugu uugggugguu ugugagccuu gcugccaagu ccugccuuug 3900
ggucgacaua guauggaagu auuugagaga gagaaccuuu ccacucccac ugccaggauu 3960
uuguauugcc aucgggugcc aaauaaaugc ucauauuuau uacugaaaaa aaaaaaaaaa 4020
aaa 4023

<210> SEQ ID NO 3
<211> LENGTH: 4057
<212> TYPE: RNA
<213> ORGANISM: Homo sapiens

<400> SEQUENCE: 3
agaggaagag aacgauuuaa ggagcgaaua cuacugguaa acuaauggaa gaaaucugcu 60
gcaccacugg auauugggag uguguggcau gcauccucau caucaggaaa cucuaaaaaa 120
gaaccgagug gugcuagcca aacagcuguu guugagcgaa uuguuagaac aucuucugga 180
gaaggacauc aucaccuugg aaaugaggga gcucauccag gccaaagugg gcaguuucag 240
ccagaaugug gaacuccuca acuugcugcc uaagaggggu ccccaagcuu uugaugccuu 300
cugugaagca cugagggaga ccaagcaagg ccaccuggag gauauguugc ucaccacccu 360
uucugggcuu cagcauguac ucccaccguu gagcugugac uacgacuuga gucucccuuu 420
uccggugugu gaguccuguc cccuuuacaa gaagcuccgc cugucgacag auacugugga 480
acacucccua gacaauaaag augguccugu cugccuucag gugaagccuu gcacuccuga 540
auuuuaucaa acacacuucc agcuggcaua uagguugcag ucucggccuc guggccuagc 600
acugguguug agcaaugugc acuucacugg agagaaagaa cuggaauuuc gcucuggagg 660
ggauguggac cacaguacuc uagucacccu cuucaagcuu uugggcuaug acguccaugu 720
ucuaugugac cagacugcac aggaaaugca agagaaacug cagaauuuug cacaguuacc 780
ugcacaccga gucacggacu ccugcaucgu ggcacuccuc ucgcauggug uggagggcgc 840
caucuauggu guggauggga aacugcucca gcuccaagag guuuuucagc ucuuugacaa 900
cgccaacugc ccaagccuac agaacaaacc aaaaaauguuc uucauccagg ccugccgugg 960
aggugcuauu ggaucccuug ggcaccuccu ucuguucacu gcugccaccg ccucucuugc 1020
ucuaugagac ugaucguggg guugaccaac aagauggaaa gaaccacgca ggauccccug 1080
ggugcgagga gagugaugcc gguaaagaaa aguugccgaa gaugagacug cccacgcgcu 1140
cagacaugau augcggcuau gccugccuca aagggacugc cgccaugcgg aacaccaaac 1200
gagguuccug guacaucgag gcucuugcuc aaguguuuuc ugagcgggcu ugugauaugc 1260
acguggccga caugcugguu aaggugaacg cacuuaucaa ggaucgggaa gguuaugcuc 1320
cuggcacaga auuccaccgg ugcaaggaga ugucugaaua cugcagcacu cugugccgcc 1380
accucuaccu guucccagga cacccuccca caugauguca ccuccccauc auccacgcca 1440
aguggaagcc acuggaccac aggaggugug auagagccuu ugaucuucag gaugcacggu 1500
uucuguucug cccccucagg gaugugggaa ucucccagac uuguuuccug ugcccaucau 1560
cucugccuuu gagugugggga cuccaggcca gcuccuuuuc ugugaagccc uuugccugua 1620
gagccagccu ugguuggacc uauugccagg aauguuucag cugcaguuga agagccugac 1680
aagugaaguu guaaacacag ugugguuaug gggagagggc auauaaauuc cccauauuug 1740
uguucaguuc cagcuuuugu agauggcacu uuagugauug cuuuuauuac auuaguuaag 1800
augucugaga gaccaucucc uaucuuuuau uucauucaua uccuccgccc uuuuuguccu 1860
agagugagag uuuggaaggu guccaaauuu aauguagaca uuaucuuuug gcucugaaga 1920

-continued

```
agcaaacaug acuagagacg caccuugcug caguguccag aagcggccug ugcguucccu   1980
ucaguacugc agcgccaccc aguggaagga cacucuuggc ucguuugggc ucaaggcacc   2040
gcagccuguc agccaacauu gccuugcauu uguaccuuau ugaucuuugc ccauggaagu   2100
cucaaagauc uuucguuggu uguuucucug agcuuuguua cugaaaugag ccucgugggg   2160
agcaucagag aaggccagga agaauggugu guuucccuag acucuguaac caccucucug   2220
ucuuuuuccu uccugagaaa cguccaucuc ucucccuuac uauucccacu uucauucaau   2280
caaccugcac uucauaucua gauuucuaga aaagcuuccu agcuuaucuc ccugcuucau   2340
aucucucccu ucuuuaccuu cauuucaucc uguuggcugc ugccaccaaa ucugucuaga   2400
auccugcuuu acaggaucau guaaaugcuc aaagauguaa uguaguucuu uguuccugcu   2460
uucucuuuca guauuaaacu cuccuuugau auuauguggc uuuuauuuca gugccauaca   2520
uguuauuguu uucaaccuag aaaccuuuau cccugcuuau cugaaacuuc ccaacuuccc   2580
uguucuuuaa gacuuuuuuu uuuuuuuuuu uuuuuuuuga gacagagucu cgcucugucg   2640
cccaggcugg agggcagugg cacgaucuca gcucacugca agcuccaacu cccggguuca   2700
cgccauucuc cugccucagc cuuccaagua gcugggacua caggugcccg ccaccgugcc   2760
cggcuaauuu uuuuguauuu uuaguagaga cagggguuuca ccauguuagc cgggauggucc   2820
uugaucuccu gaccucauga uccacccacc ucagccuccc aaaguguugg gauuacaggc   2880
gugagccacu gcgcccgggc aagaccuuuu uuuaaaaaaa aaaaaaaaaa aacuuccauu   2940
cuuucuuccu ccagucuguu cucacauaac agaguaguuu ugguuuuuaa uuuuuuuugg   3000
uuguuugcug uuuuuuguuu uuuaagguga guucucacua uguuucucag acuggucucg   3060
aacuccuggc cucaagccau cuucccgccu cagccucuca aauagcuggg cuuacaggca   3120
ugagccacca caccuggcca ggauuugguu guuuaaauau aaaucugauc acccccccugc   3180
uuagaacccu ucugcuuucu auuaccccuc auuuaaaaug uaaacucuuc accuugguuu   3240
augagaacug guucuugccu uccccuugaa ccucauuaaa uggugauuuc uugcuaagcu   3300
ccagcccgag ugguucuccuc ucagcuucua auuuugugcu cuuuccugcc cuuuuccugg   3360
gccuucucag cucuccaccc ccaccacucu ugacucaggu gguguccuuc uuccucaagu   3420
cuugacaauu cccgggcccu ucagucccug agcagucuac uucugugucu gucaccacau   3480
cuugucuuuu ccccucauug cauuuauugc aguuuauaua uaugcuacuu uuacuuguuc   3540
auuucugucu ccccuaccag gcuguaaaug agggcagaaa ccuuguuugu uuuauucacc   3600
aucauguacc aagugcuugg cacauagugg gccuucauua aauguuuguu gaauaaaaga   3660
gggaagaagg caagccaacc uuagcuacaa uccuaccuuu ugauaaaaug uuccuuuuga   3720
caauauacac ggauuauuau uuguacuuug uuuuuccaug uguuuugcuu uuauccacug   3780
gcauuuuuag cuccuugaag acauaucaug ugugagauaa cuuccuucac aucucccaug   3840
gucccuagca aaaugcuagg ccuguaguag ucaaggugcu caauaaauau uuguuugggu   3900
gguuugugag ccuugcugcc aaguccugcc uuugggucga cauaguaugg aaguauuuga   3960
gagagagaac cuuuccacuc ccacugccag gauuuuguau ugccaucggg ugccaaauaa   4020
augcucauau uuauuacuga aaaaaaaaaa aaaaaaa                            4057
```

<210> SEQ ID NO 4
<211> LENGTH: 4057
<212> TYPE: RNA
<213> ORGANISM: Homo sapiens -continued

<400> SEQUENCE: 4

```
agaggaagag aacgauuuaa ggagcgaaua cuacugguaa acuaauggaa gaaaucugcu     60
gcaccacugg auauugggag uguguggcau gcauccucau caucaggaaa cucuaaaaaa    120
gaaccgagug gugcuagcca aacagcuguu guugagcgaa uuguuagaac aucuucugga    180
gaaggacauc aucaccuugg aaaugaggga gcucauccag gccaaagugg gcaguuucag    240
ccagaaugug gaacuccuca acuugcugcc uaagaggggu ccccaagcuu uugaugccuu    300
cugugaagca cugagggaga ccaagcaagg ccaccuggag gauauguugc ucaccacccu    360
uucugggcuu cagcauguac ucccaccguu gagcugugac uacgacuuga gucucccuuu    420
uccggugugu gaguccuguc cccuuuacaa gaagcuccgc cugucgacag auacugugga    480
acacucccua gacaauaaag augguccugu cugccuucag gugaagccuu gcacuccuga    540
auuuuaucaa acacacuucc agcuggcaua uagguugcag ucucggccuc guggccuagc    600
acugguguug agcaaugugc acuucacugg agagaaagaa cuggaauuuc gcucuggagg    660
ggauguggac cacaguacuc uagucacccu cuucaagcuu uugggcuaug acguccaugu    720
ucuaugugac cagacugcac aggaaaugca agagaaacug cagaauuuug cacaguuacc    780
ugcacaccga gucacggacu ccugcaucgu ggcacuccuc ucgcauggug uggagggcgc    840
caucuauggu guggauggga aacugcucca gcuccaagag guuuuucagc ucuuugacaa    900
cgccaacugc ccaagccuac agaacaaacc aaaaauguuc uucauccagg ccugccgugg    960
aggugcuauu ggaucccuug ggcaccuccu ucuguucacu gcugccaccg ccucucuugc   1020
ucuaugagac ugaucguggg guugaccaac aagauggaaa gaaccacgca ggaucccug    1080
ggugcgagga gagugaugcc gguaaagaaa aguugccgaa gaugagacug cccacgcgcu   1140
cagacaugau augcggcuau gccugccuca aagggacugc cgccaugcgg aacaccaaac   1200
gagguuccug guacaucgag gcucuugcuc aaguguuuuc ugagcgggcu ugugauaugc   1260
acguggccga caugcugguu aaggugaacg cacuuaucaa ggaucgggaa gguuaugcuc   1320
cuggcacaga auuccaccgg ugcaaggaga ugucugaaua cugcagcacu cugugccgcc   1380
accucuaccu guucccagga cacccuccca caugauguca ccucccccauc auccacgcca   1440
aguggaagcc acuggaccac aggaggugug auagagccuu ugaucuucag gaugcacggu   1500
uucuguucug cccccucagg gaugugggaa ucucccagac uuguuuccug ugcccaucau   1560
cucugccuuu gaguguggga cuccaggcca gcuccuuuuc ugugaagccc uuugccugua   1620
gagccagccu ugguuggacc uauugccagg aauguuucag cugcaguuga agagccugac   1680
aagugaaguu guaaacacag ugugguuaug gggagagggc auauaaauuc cccauauuug   1740
uguucaguuc cagcuuuugu agauggcacu uuagugauug cuuuuauuac auuaguuaag   1800
augucugaga gaccaucucc uaucuuuuau uucauucaua ucccucgccc uuuuugccu    1860
agagugagag uuuggaaggu guccaaauuu aauguagaca uuaucuuuug gcucugaaga   1920
agcaaacaug acuagagacg caccuugcug caguguccag aagcggccug ugcguucccu   1980
ucaguacugc agcgccaccc aguggaagga cacucuuggc ucguuugggc ucaaggcacc   2040
gcagccuguc agccaacauu gccuugcauu uguaccuuau ugaucuuugc ccauggaagu   2100
cucaaagauc uuucguuggu uguuucucug agcuuuguua cugaaaugag ccucgugggg   2160
agcaucagag aaggccagga agaauggugu guuucccuag acucuguaac caccucucug   2220
ucuuuuuccu uccugagaaa cguccaucuc ucucccuuac uauucccacu uucauucaau   2280
caaccugcac uucauaucua gauuucuaga aaagcuuccu agcuuaucuc ccugcuucau   2340
```

-continued

```
aucucucccu ucuuuaccuu cauuucaucc uguuggcugc ugccaccaaa ucugucuaga   2400

auccugcuuu acaggaucau guaaaugcuc aaagauguaa uguaguucuu uguuccugcu   2460

uucucuuuca guauuaaacu cuccuuugau auuauguggc uuuuauuuca gugccauaca   2520

uguuauuguu uucaaccuag aaaccuuuau cccugcuuau cugaaacuuc ccaacuuccc   2580

uguucuuuaa gacuuuuuuu uuuuuuuuuu uuuuuuuuga gacagagucu cgcucugucg   2640

cccaggcugg agggcagugg cacgaucuca gcucacugca agcuccaacu cccggguuca   2700

cgccauucuc cugccucagc cuuccaagua gcugggacua caggugcccg ccaccgugcc   2760

cggcuaauuu uuuguauuu uuaguagaga cagggguuuca ccauguuagc cgggaugguc   2820

uugaucuccu gaccucauga uccacccacc ucagccuccc aaaguguugg gauuacaggc   2880

gugagccacu gcgcccgggc aagaccuuuu uuuaaaaaaa aaaaaaaaaa aacuuccauu   2940

cuuucuuccu ccagucuguu cucacauaac agaguaguuu ugguuuuuaa uuuuuuuugg   3000

uuguuugcug uuuuuuguuu uuuaagguga guucucacua uguuucucag acuggucucg   3060

aacuccuggc cucaagccau cuucccgccu cagccucuca aauagcuggg cuuacaggca   3120

ugagccacca caccuggcca ggauuugguu guuuaaauau aaaucugauc accccccugc   3180

uuagaacccu ucugcuuucu auuaccccuc auuuaaaaug uaaacucuuc accuugguuu   3240

augagaacug guucuugccu uccccuugaa ccucauuaaa uggugauuuc uugcuaagcu   3300

ccagcccgag uggucuccuc ucagcuucua auuuugugcu cuuuccugcc cuuuuccugg   3360

gccuucucag cucuccaccc ccaccacucu ugacucaggu ggguccuuc uuccucaagu   3420

cuugacaauu cccgggcccu ucagucccug agcagucuac uucugugucu gucaccacau   3480

cuugucuuuu ccccucauug cauuuauugc aguuuauaua uaugcuacuu uuacuuguuc   3540

auuucugucu ccccuaccag gcuguaaaug agggcagaaa ccuuguuugu uuuauucacc   3600

aucauguacc aagugcuugg cacauagugg gccuucauua aauguuuguu gaauaaaaga   3660

gggaagaagg caagccaacc uuagcuacaa uccuaccuuu ugauaaaaug uuccuuuuga   3720

caauauacac ggauuauuau uuguacuuug uuuuuccaug uguuuugcuu uuauccacug   3780

gcauuuuuag cuccuugaag acauaucaug ugugagauaa cuuccuucac aucucccaug   3840

gucccuagca aaaugcuagg ccuguaguag ucaaggugcu caauaaaauau uuguuugggu   3900

gguuugugag ccuugcugcc aaguccugcc uuugggucga cauaguaugg aaguauuuga   3960

gagagagaac cuuuccacuc ccacugccag gauuuuguau ugccaucggg ugccaaauaa   4020

augcucauau uuauuacuga aaaaaaaaaa aaaaaaa                            4057
```

<210> SEQ ID NO 5
<211> LENGTH: 1492
<212> TYPE: RNA
<213> ORGANISM: Homo sapiens

<400> SEQUENCE: 5

```
cgggcgacag cagggccgcg gugcaguguc cgacccgaga guugcggccu gagucaccgg     60

ccccgcccuc cggagccgga cgcugcggga ggcccgggag cggcagugga accgacuccc    120

agaacuccgg acgugugcgg cgcagugagu cgcagccaug uuccugguua acucguucuu    180

gaagggcggc ggcggcggcg gcgggggagg cgggggccug ggugggggcc ugggaaaugu    240

gcuuggaggc cugaucagcg ggccgggggg cggcggcggc ggcggcggcg gcggcggcgg    300

ugguggaggc ggcgguggcg guggaacggc caugcgcauc cuaggcggag ucaucagcgc    360

caucagcgag gcggcugcgc aguacaaccc ggagcccccg cccccacgca cacauuacuc    420
```

-continued

```
caacauugag gccaacgaga gugaggaggu ccggcaguuc cggagacucu uugcccagcu    480

ggcuggagau gacauggagg ucagcgccac agaacucaug aacauucuca auaagguugu    540

gacacgacac ccugaucuga agacugaugg uuuuggcauu gacacauguc gcagcauggu    600

ggccgugaug gauagcgaca ccacaggcaa gcugggcuuu gaggaauuca aguacuugug    660

gaacaacauc aaaagguggc aggccauaua caaacaguuc gacacugacc gaucagggac    720

cauuugcagu agugaacucc caggugccuu ugaggcagca ggguuccacc ugaaugagca    780

ucucuauaac augaucaucc gacgcuacuc agaugaaagu gggaacaugg auuuugacaa    840

cuucaucagc ugcuugguca ggcuggacgc cauguuccgu gccuucaaau cucuugacaa    900

agauggcacu ggacaaaucc aggugaacau ccaggagugg cugcagcuga cuauguauuc    960

cugaacugga gccccagacc cgcccccuca cugccuugcu auaggaguca ccuggagccu   1020

cggucucucc cagggccgau ccugucugca gucacaucuu uguggggccu gcugacccac   1080

aagcuuuugu ucucucagua cuuguuaccc agcuucucaa cauccagggc ccaauuugcc   1140

cugccuggag uucccccugg cucuaggaca cucuaacaag cucuguccac gggucucccc   1200

auucccacca ggcccugcac acacccacuc cguaaccucu ccccuguacc ugugccaagc   1260

cuagcacuug ugaugccucc augccccgag ggcccucucu caguucuggg aggaugacuc   1320

cagucccugc acgcccuggc acacccuuca cgguugcuac ccaggcggcc aagcuccaga   1380

ccgugccaga cccaggugcc ccagugccuu ugucuauauu cugcucccag ccugccaggc   1440

ccaggaggaa auaaacaugc cccaguugcu gaucucuaaa aaaaaaaaaa aa           1492
```

<210> SEQ ID NO 6
<211> LENGTH: 1200
<212> TYPE: RNA
<213> ORGANISM: Homo sapiens

<400> SEQUENCE: 6

```
cgggcgacag cagggccgcg ggcaggccga cccgagaggc ggccgagcac cggccccgcc     60

cccggagccg gacgcgcggg aggcccggga gcggcaggga accgacccca gaacccggac    120

gggcggcgga gcgcagccag ccggaaccgc gaagggcggc ggcggcggcg gcgggggagg    180

cgggggccgg ggggggccgg gaaaggcgga ggccgacagc ggggccgggg gcggcggcgg    240

cggcggcggc ggcggcggcg gggggaggcg gcggggcggg gaacggccag cgcaccaggc    300

ggagcacagc gccacagcga ggcggcgcgc agacaacccg gagcccccgc ccccacgcac    360

acaacccaac agaggccaac gagaggagga ggccggcagc cggagaccgc ccagcggcgg    420

agagacagga ggcagcgcca cagaaccaga acaccaaaag gggacacgac acccgacgaa    480

gacgaggggc agacacagcg cagcaggggc cggaggaagc gacaccacag gcaagcgggc    540

gaggaacaag acgggaacaa cacaaaaggg gcaggccaaa caaacagcga cacgaccgac    600

agggaccagc agaggaaccc cagggccgag gcagcagggc caccgaagag caccaaacag    660

acaccgacgc accagagaaa ggggaacagg agacaaccac agcgcggcag gcggacgcca    720

gccggcccaa accgacaaag aggcacggac aaaccaggga acaccaggag ggcgcagcga    780

cagaccgaac ggagccccag acccgccccc cacgccgcaa ggagcaccgg agcccggccc    840

ccagggccga ccgcgcagca cacgggggcc gcgacccaca agcgcccaga cgacccagcc    900

caacaccagg gcccaagccc gccggagccc ccggccagga caccaacaag ccgccacggg    960

cccccaccca ccaggcccgc acacacccac ccgaaccccc ccgaccggcc aagccagcac   1020

ggagccccag ccccgagggc cccccagcgg gaggagaccc agcccgcacg cccggcacac   1080
```

-continued

```
cccacgggca cccaggcggc caagcccaga ccggccagac ccagggcccc aggccgcaac   1140

gccccagccg ccaggcccag gaggaaaaaa cagccccagg cgaccaaaaa aaaaaaaaaa   1200
```

<210> SEQ ID NO 7
<211> LENGTH: 1925
<212> TYPE: RNA
<213> ORGANISM: Homo sapiens

<400> SEQUENCE: 7

```
uggaugagcu gugagugcgc gcgcgugcgc ggggccgcga ccugugccgg cucgagcccg     60

cugggcacuc ggaggcgcgc acgucguucc ccgcccuccc gccgccgccc gcccucgcuc    120

ucucgcgcua cccucccgcc gcccgcgguc cuccgucggu ucucucguua guccacgguc    180

uggucuucag cuacccgccu ucgucuccga guuugcgacu cgcggaccgg cguccccggc    240

gcgaagaggc uggacucgga uucguugccu gagcaauggc ugccauccgg aagaaacugg    300

ugauuguugg ugauggagcc uguggaaaga caugcuugcu cauagucuuc agcaaggacc    360

aguucccaga ggguguaugug cccacagugu uugagaacua uguggcagau aucgaggugg    420

auggaaagca gguagaguug gcuuuguggg acacagcugg gcaggaagau uaugaucgcc    480

ugaggccccu cuccuaccca gauaccgaug uuauacugau guguuuuucc aucgacagcc    540

cugauaguuu agaaaacauc ccagaaaagu ggaccccaga agucaagcau uucugucca    600

acgugcccau cauccugguu gggaauaaga aggaucuucg gaaugaugag cacacaaggc    660

gggagcuagc caagaugaag caggagccgg ugaaaccuga agaaggcaga gauauggcaa    720

acaggauugg cgcuuuuggg uacauggagu guucagcaaa gaccaaagau ggagugagag    780

agguuuuuga aauggcuacg agagcugcuc ugcaagcuag acgugggaag aaaaaaucug    840

ggugccuugu cuugugaaac cuugcugcaa gcacagcccu uaugcgguua auuuugaagu    900

gcuguuuauu aaucuuagug uaugauuacu ggccuuuuuc auuuaucuau aauuuaccua    960

agauuacaaa ucagaaguca ucuugcuacc aguauuuaga agccaacuau gauuauuaac   1020

gauguccaac ccgucuggcc caccaggguc cuuuugacac ugcucuaaca gcccuccucu   1080

gcacucccac cugacacacc aggcgcuaau ucaaggaauu ucuuaacuuc uugcuucuuu   1140

cuagaaagag aaacaguugg uaacuuuugu gaauuaggcu guaacuacuu uauaacuaac   1200

auguccugcc uauuaucugu cagcugcaag guacucuggu gagucaccac uucagggcuu   1260

uacuccguaa cagauuuugu uggcauagcu cugggguggg caguuuuuug aaaaugggcu   1320

caaccagaaa agcccaaguu caugcagcug uggcagaguu acaguucugu gguuucaugu   1380

uaguuaccuu auaguuacug uguaauuagu gccacuuaau guauguuacc aaaaauaaau   1440

auaucuaccc cagacuagau guaguauuuu uuguauaauu ggauuuccua auacugucau   1500

ccucaaagaa aguguauugg uuuuuuaaaa aagaaagugu auuuggaaau aaagucagau   1560

ggaaaauuca uuuuuuaaau ucccguuuug ucacuuuuuc ugauaaaaga uggccauauu   1620

accccuuuuc ggccccaugu aucucaguac cccauggagc ugggcuaagu aaauaggaau   1680

ugguuucacg ccugaggcaa uuagacacuu uggaagaugg cauaaccugu cucaccugga   1740

cuuaagcauc uggcucuaau ucacagugcu cuuuucuccu cacuguaucc agguucccuc   1800

ccagaggagc caccaguucu caugggugc acucagucuc ucuucucucc agcugacuaa   1860

acuuuuuuuc uguaccaguu aauuuuucca acuacuaaua gaauaaaggc aguuucuaa   1920

aaaaa                                                                1925
```

<210> SEQ ID NO 8
<211> LENGTH: 19
<212> TYPE: RNA
<213> ORGANISM: Artificial
<220> FEATURE:
<223> OTHER INFORMATION: Chemically synthesized
<220> FEATURE:
<221> NAME/KEY: misc_feature
<222> LOCATION: (1)..(1)
<223> OTHER INFORMATION: optional capping moiety covalently attached to position 1 (5') ribonucleotide
<220> FEATURE:
<221> NAME/KEY: misc_feature
<222> LOCATION: (19)..(19)
<223> OTHER INFORMATION: optional 3' overhang moiety covalently attached to position 19 (3') ribonucleotide

<400> SEQUENCE: 8
gccagaaugu ggaacuccu 19

<210> SEQ ID NO 9
<211> LENGTH: 19
<212> TYPE: RNA
<213> ORGANISM: Artificial
<220> FEATURE:
<223> OTHER INFORMATION: Chemically synthesized
<220> FEATURE:
<221> NAME/KEY: misc_feature
<222> LOCATION: (19)..(19)
<223> OTHER INFORMATION: optional capping moiety covalently attached to position 19 (3') ribonucleotide

<400> SEQUENCE: 9
aggaguucca cauucuggc 19

<210> SEQ ID NO 10
<211> LENGTH: 19
<212> TYPE: RNA
<213> ORGANISM: Artificial
<220> FEATURE:
<223> OTHER INFORMATION: Chemically synthesized

<400> SEQUENCE: 10
uccuggaacu ucacaugaa 19

<210> SEQ ID NO 11
<211> LENGTH: 19
<212> TYPE: RNA
<213> ORGANISM: Artificial
<220> FEATURE:
<223> OTHER INFORMATION: Chemically synthesized

<400> SEQUENCE: 11
uucaugugaa guuccagga 19

<210> SEQ ID NO 12
<211> LENGTH: 19
<212> TYPE: RNA
<213> ORGANISM: Artificial
<220> FEATURE:
<223> OTHER INFORMATION: Chemically synthesized

<400> SEQUENCE: 12
gcuacagaac ucaugaaua 19

<210> SEQ ID NO 13
<211> LENGTH: 19
<212> TYPE: RNA
<213> ORGANISM: Artificial

<220> FEATURE:
<223> OTHER INFORMATION: Chemically synthesized

<400> SEQUENCE: 13
uauucaugag uucuguagc 19

<210> SEQ ID NO 14
<211> LENGTH: 19
<212> TYPE: RNA
<213> ORGANISM: Artificial
<220> FEATURE:
<223> OTHER INFORMATION: Chemically synthesized

<400> SEQUENCE: 14
gccacuuaau guauguuac 19

<210> SEQ ID NO 15
<211> LENGTH: 19
<212> TYPE: RNA
<213> ORGANISM: Artificial
<220> FEATURE:
<223> OTHER INFORMATION: Chemically synthesized

<400> SEQUENCE: 15
guaacauaca uuaaguggc 19

<210> SEQ ID NO 16
<211> LENGTH: 21
<212> TYPE: RNA
<213> ORGANISM: Artificial
<220> FEATURE:
<223> OTHER INFORMATION: Chemically synthesized

<400> SEQUENCE: 16
ggcuacgucc aggagcgcac c 21

<210> SEQ ID NO 17
<211> LENGTH: 21
<212> TYPE: RNA
<213> ORGANISM: Artificial
<220> FEATURE:
<223> OTHER INFORMATION: Chemically synthesized

<400> SEQUENCE: 17
ggugcgcucc uggacguagc c 21

<210> SEQ ID NO 18
<211> LENGTH: 19
<212> TYPE: RNA
<213> ORGANISM: Artificial
<220> FEATURE:
<223> OTHER INFORMATION: Chemically synthesized

<400> SEQUENCE: 18
gcacuccuga auuuuauca 19

<210> SEQ ID NO 19
<211> LENGTH: 19
<212> TYPE: RNA
<213> ORGANISM: Artificial
<220> FEATURE:
<223> OTHER INFORMATION: Chemically synthesized

<400> SEQUENCE: 19
ugauaaaauu caggagugc 19

-continued

```
<210> SEQ ID NO 20
<211> LENGTH: 19
<212> TYPE: RNA
<213> ORGANISM: Artificial
<220> FEATURE:
<223> OTHER INFORMATION: Chemically synthesized

<400> SEQUENCE: 20

gcacaggaaa ugcaagaga                                                19


<210> SEQ ID NO 21
<211> LENGTH: 19
<212> TYPE: RNA
<213> ORGANISM: Artificial
<220> FEATURE:
<223> OTHER INFORMATION: Chemically synthesized

<400> SEQUENCE: 21

ucucuugcau uuccugugc                                                19


<210> SEQ ID NO 22
<211> LENGTH: 19
<212> TYPE: RNA
<213> ORGANISM: Artificial
<220> FEATURE:
<223> OTHER INFORMATION: Chemically synthesized

<400> SEQUENCE: 22

gggcuuguga uaugcacgu                                                19


<210> SEQ ID NO 23
<211> LENGTH: 19
<212> TYPE: RNA
<213> ORGANISM: Artificial
<220> FEATURE:
<223> OTHER INFORMATION: Chemically synthesized

<400> SEQUENCE: 23

acgugcauau cacaagccc                                                19


<210> SEQ ID NO 24
<211> LENGTH: 19
<212> TYPE: RNA
<213> ORGANISM: Artificial
<220> FEATURE:
<223> OTHER INFORMATION: Chemically synthesized
<220> FEATURE:
<221> NAME/KEY: misc_feature
<222> LOCATION: (1)..(1)
<223> OTHER INFORMATION: optional capping moiety covalently attached to
      position 1 (5') ribonucleotide
<220> FEATURE:
<221> NAME/KEY: misc_feature
<222> LOCATION: (18)..(18)
<223> OTHER INFORMATION: L-deoxycytidine
<220> FEATURE:
<221> NAME/KEY: misc_feature
<222> LOCATION: (19)..(19)
<223> OTHER INFORMATION: optional 3' overhang moiety covalently attached
      to position 19 (3') ribonucleotide

<400> SEQUENCE: 24

gccagaaugu ggaacuccu                                                19


<210> SEQ ID NO 25
<211> LENGTH: 19
<212> TYPE: RNA
<213> ORGANISM: Artificial
```

```
<220> FEATURE:
<223> OTHER INFORMATION: Chemically synthesized
<220> FEATURE:
<221> NAME/KEY: misc_feature
<222> LOCATION: (1)..(19)
<223> OTHER INFORMATION: strand comprises at least five (5) alternating
      unmodified and 2'-O-methyl sugar modified ribonucleotides
<220> FEATURE:
<221> NAME/KEY: misc_feature
<222> LOCATION: (19)..(19)
<223> OTHER INFORMATION: optional capping moiety covalently attached to
      position 9 (3') ribonucleotide

<400> SEQUENCE: 25

aggaguucca cauucuggc                                                19


<210> SEQ ID NO 26
<211> LENGTH: 19
<212> TYPE: RNA
<213> ORGANISM: Artificial
<220> FEATURE:
<223> OTHER INFORMATION: Chemically synthesized
<220> FEATURE:
<221> NAME/KEY: misc_feature
<222> LOCATION: (1)..(1)
<223> OTHER INFORMATION: inverted deoxyabasic moiety covalently attached
      to position 1 (5') ribonucleotide
<220> FEATURE:
<221> NAME/KEY: misc_feature
<222> LOCATION: (18)..(18)
<223> OTHER INFORMATION: L-deoxycytidine

<400> SEQUENCE: 26

gccagaaugu ggaacuccu                                                19


<210> SEQ ID NO 27
<211> LENGTH: 19
<212> TYPE: RNA
<213> ORGANISM: Artificial
<220> FEATURE:
<223> OTHER INFORMATION: Chemically synthesized
<220> FEATURE:
<221> NAME/KEY: misc_feature
<222> LOCATION: (2)..(2)
<223> OTHER INFORMATION: 2'O-methyl sugar modified ribonucleotide
<220> FEATURE:
<221> NAME/KEY: misc_feature
<222> LOCATION: (4)..(4)
<223> OTHER INFORMATION: 2'O-methyl sugar modified ribonucleotide
<220> FEATURE:
<221> NAME/KEY: misc_feature
<222> LOCATION: (6)..(6)
<223> OTHER INFORMATION: 2'O-methyl sugar modified ribonucleotide
<220> FEATURE:
<221> NAME/KEY: misc_feature
<222> LOCATION: (8)..(8)
<223> OTHER INFORMATION: 2'O-methyl sugar modified ribonucleotide
<220> FEATURE:
<221> NAME/KEY: misc_feature
<222> LOCATION: (11)..(11)
<223> OTHER INFORMATION: 2'O-methyl sugar modified ribonucleotide
<220> FEATURE:
<221> NAME/KEY: misc_feature
<222> LOCATION: (13)..(13)
<223> OTHER INFORMATION: 2'O-methyl sugar modified ribonucleotide
<220> FEATURE:
<221> NAME/KEY: misc_feature
<222> LOCATION: (15)..(15)
<223> OTHER INFORMATION: 2'O-methyl sugar modified ribonucleotide
<220> FEATURE:
<221> NAME/KEY: misc_feature
<222> LOCATION: (17)..(17)
<223> OTHER INFORMATION: 2'O-methyl sugar modified ribonucleotide
```

-continued

```
<220> FEATURE:
<221> NAME/KEY: misc_feature
<222> LOCATION: (19)..(19)
<223> OTHER INFORMATION: 2'O-methyl sugar modified ribonucleotide

<400> SEQUENCE: 27

aggaguucca cauucuggc                                             19
```

METHODS AND COMPOSITIONS FOR NEUROPROTECTION

RELATED APPLICATIONS

This is the U.S. National Stage of International Application No. PCT/US2012/062894, filed Nov. 1, 2012, which was published in English under PCT Article 21(2), which in turn claims the benefit of U.S. Provisional Application Ser. No. 61/554,982 filed Nov. 3, 2011 entitled "Compositions and Methods For Treating Meniere's Disease" and of U.S. Provisional Application Ser. No. 61/663,627 filed Jun. 25, 2012 entitled "Compositions and Methods For Treating Meniere's Disease" which are incorporated herein by reference in their entirety and for all purposes.

SEQUENCE LISTING

This application incorporates-by-reference nucleotide and/or amino acid sequences which are present in the file named "240_PCT1_ST25.txt", which is 33 kilobytes in size, and which was created Nov. 1, 2012 in the IBM-PCT machine format, having an operating system compatibility with MS-Windows.

FIELD OF THE INVENTION

Provided herein is use of a double-stranded RNA compound that targets CASP2, NOX3, CAPNS1 or RHOA for use in neuroprotection of neurons in the ear of a subject and for restoration of lost cochlear and/or vestibular function and/or relief of the attendant symptoms. Further provided are methods and kits useful for treating a subject at risk of or afflicted with Ménière's disease or similar diseases and disorders.

BACKGROUND OF THE INVENTION

The human ear is comprised of three major structural components: the outer, middle, and inner ears, which function together to convert sound waves into nerve impulses that travel to the brain, where they are perceived as sound. The inner ear also helps to maintain balance.

The anatomy of the middle and the inner ear is well known to those of ordinary skill in the art (see, e.g., Atlas of Sensory Organs: Functional and Clinical Analysis, Andrs Csillag, Humana Press (2005), pages 1-82, incorporated herein by reference). In brief, the middle ear consists of the eardrum and a small air-filled chamber containing three tiny bones known as the ossicles, which link the eardrum to the inner ear.

The inner ear (labyrinth) is a complex structure consisting of the cochlea, which is the organ of hearing, and the vestibular system, the organ of balance. The vestibular system consists of the saccule and the utricle, which determine position sense, and the semicircular canals, which help maintain balance.

The cochlea houses the organ of Corti, which consists, in part, of about 20,000 specialized sensory cells, called "inner ear hair cells" or "hair cells". These cells have small hairline projections (cilia) that extend into the cochlear fluid. Sound vibrations transmitted from the ossicles in the middle ear to the oval window in the inner ear cause the fluid and cilia to vibrate. Hair cells in different parts of the cochlea vibrate in response to different sound frequencies and convert the vibrations into nerve impulses which are sent to the brain for processing and interpretation. The inner ear hair cells are surrounded by inner ear support cells. Supporting cells underlie, at least partially surround, and physically support sensory hair cells within the inner ear. Representative examples of support cells include inner rod (pillar cells), outer rod (pillar cells), inner phalangeal cells, outer phalangeal cells (of Deiters), cells of Held, cells of Hensen, cells of Claudius, cells of Boettcher, interdental cells and auditory teeth (of Huschke).

The spiral ganglion is the group of nerve cells that send a representation of sound from the cochlea to the brain. The cell bodies of the spiral ganglion neurons are found in the spiral structure of the cochlea and are part of the central nervous system. Their dendrites make synaptic contact with the base of hair cells, and their axons are bundled together to form the auditory portion of the eighth cranial nerve (vestibulocochlear nerve). The vestibular ganglion (also known as Scarpa's ganglion) is the ganglion of the vestibular nerve that contains the cell bodies of the bipolar primary afferent neurons whose peripheral processes form synaptic contact with hair cells of the vestibular sensory end organs.

US Patent Application Publication Nos. 20090162365 and 20110112168 are directed to siRNA compounds, compositions comprising same and to methods of use thereof for treating diseases and disorders related to expression of proapoptotic genes.

U.S. Pat. No. 7,825,099 relates to methods of treating hearing impairment by inhibiting a pro-apoptotic gene.

U.S. Pat. No. 8,088,359 and US Patent Application Publication No. 20120252868 relate to methods of treating hearing loss and phantom hearing.

US Patent Application Publication No. 20110142917 discloses non-invasive methods of delivering dsRNA molecules to the ear.

US Patent Application Publication No. 20110034534 relates to, inter alia, dsRNA molecules to target CAPNS1.

US Patent Application Publication No. 20110229557 relates to dsRNA molecules to various gene targets, including CASP2, useful in treating eye diseases.

PCT Patent Publication No. WO2011/163436 discloses dsRNA to target RHOA.

Tinnitus and Ménière's disease affects many individuals worldwide and current therapies have not been successful at preventing progression of neuronal degeneration and the attendant hearing loss. A therapeutic treatment, which would protect the inner ear neurons, including hair cells and spiral and vestibular ganglion cells, from damage and cell death (e.g. apoptosis), and thereby attenuate or prevent hearing loss in, for example, Ménière's patients would be highly desirable. It is, accordingly, an aspect to provide methods for neuroprotection of neurons in a subject's ear, including human subjects suffering from tinnitus or Ménière's disease or having similar symtoms, using dsRNA compounds not previously known to have such activity.

SUMMARY OF THE INVENTION

This disclosure is directed to methods and kits for providing neuroprotection to neurons in subject's ear, for example to spiral ganglion cells and vestibular ganglion cells. In one aspect, disclosed herein is a double-stranded RNA (dsRNA) compound which down regulates expression of a CASP2 gene, a NOX3 gene, a CAPNS1 gene or a RHOA gene encoding an mRNA having a sequence set forth in any one of SEQ ID NO:1-3, SEQ ID NO:4, SEQ ID NO:5-6 or SEQ ID NO:7 for use in neuroprotection of a neuron in the ear of a subject in need thereof. In various aspects provided is a method providing neuroprotection to neurons in the ear, the method comprising administering to the subject's ear a therapeutically effective amount of a double-stranded RNA (dsRNA) molecule compound which down regulates expression of a CASP2 gene, a NOX3 gene, a CAPNS1 gene, or a RHOA gene, so as to thereby provide neuroprotection to a nerve cell in the subject's ear. In some embodiments the neuron is a ganglion. In some embodiments the neuron is comprised within a ganglion. In some embodiments the neuron comprises a spiral ganglion cell and/or a vestibular ganglion cell. In some embodiments the CASP2 gene encodes a mRNA having a sequence set forth in any one of SEQ ID NO:1-3. In some embodiments the NOX3 gene encodes a mRNA having a sequence set forth in SEQ ID NO:4. In some embodiments the CAPNS1 gene encodes a mRNA having a sequence set forth in any one of SEQ ID NO:5-6. In some embodiments the RHOA gene encodes a mRNA having a sequence set forth in SEQ ID NO:7. In some embodiments, CASP2 is the preferred target gene and in preferred embodiments the dsRNA molecule compound comprises a sense strand with a nucleotide sequence set forth in SEQ ID NO:8 and an antisense strand with a nucleotide sequence set forth in SEQ ID NO:9. In some embodiments neuroprotection comprises attenuation, prevention or reduction of neuronal cell death, preferably apoptotic cell death. According to some embodiments cell death of the neuron is associated with one or more of a disease or disorder, ischemia, physical/mechanical trauma, exposure to a chemical agent or an infectious agent, an immunologic reaction or a nutritional imbalance. In some embodiments cell death of the neuron is associated with ischemia. In some embodiments cell death of the neuron is associated with a disease or a condition. In some embodiments the disease is a genetic disease or disorder. In various embodiments the disease or condition is selected from the group consisting of a disorder associated with pathological abnormality in the auditory organs and a disorder associated with a pathological abnormality in the vestibular organs. In some embodiments the auditory organ is the organ of Corti. The vestibular ganglion are the sensory ganglion of the vestibular part of the eighth cranial nerve, located in the upper part of the lateral end of the internal acoustic meatus. In some embodiments the vestibular organ is selected from the utricle, saccule, internal acoustic meatus and ampullae.

In some embodiments the subject has or is at risk of developing one or more of a disease or condition or a symptom thereof selected from the group consisting of episodic vertigo, hearing loss, tinnitus and aural fullness. In certain embodiments the subject is afflicted with or susceptible to developing Ménière's disease.

In some embodiments, provided herein is a method of treating a subject afflicted with Ménière's disease comprising administering to the subject a therapeutically effective amount of a dsRNA compound that down regulates expression of a CASP2, a NOX3, a RHOA or a CAPNS1 gene, thereby treating the subject.

In some embodiments, the method comprises attenuating a symptom of Ménière's disease in a subject afflicted with Ménière's disease, comprising administering to the subject a therapeutically effective amount of a dsRNA compound that down regulates expression of a CASP2, a NOX3, a RHOA or a CAPNS1 gene, thereby attenuating a symptom of Ménière's disease. In some embodiments the symptom comprises one or more of tinnitus, progressive hearing loss, ELH, vertigo, nausea or aural fullness. In some embodiments the method provides relief of one or more of the symptoms of Ménière's disease. In some embodiments the method provides partial restoration or full restoration of hearing.

In some embodiments the methods and kits include rescuing a spiral ganglion and/or a vestibular ganglion from apoptosis in a subject. In some embodiments the methods include promoting survival of spiral ganglion and/or a vestibular ganglion. In some embodiments the methods include preventing apoptotic cell death of a spiral ganglion cell and or a vestibular ganglion cell in a subject. In some embodiments the methods include providing neuroprotection of a spiral ganglion cell and or a vestibular ganglion cell in a subject. In some embodiments the methods include restoration of cochlear function in the subject. Cochlear function includes partial or full restoration of hearing. In some embodiments the methods include restoration of vestibular function in a subject. Vestibular function includes partial or full restoration of balance.

Further provided are kits for treating a subject afflicted with Ménière's disease comprising a therapeutically effective amount of a dsRNA compound that down regulates expression of a CASP2, a NOX3, a RHOA or a CAPNS1 gene. In some embodiments the kit further includes a device for the administration of the dsRNA compound to the subject; and optionally instructions for use. In some embodiments the kit comprises a dsRNA compound that down regulates expression of a CASP2 gene. In preferred embodiments the CASP2 gene encodes a mRNA set forth in any one of SEQ ID NO:1-3. In preferred embodiments the kit provides a dsRNA compound comprising a sense strand with a nucleotide sequence set forth in SEQ ID NO:8 and an antisense strand with a nucleotide sequence set forth in SEQ ID NO:9.

In some embodiments the methods and kits involve use of dsRNA compounds (for example, short interfering nucleic acid (siNA), short interfering RNA (siRNA), micro-RNA (miRNA) or short hairpin RNA (shRNA)) that bind a nucleotide sequence (such as an mRNA sequence) encoding a human target gene selected from CASP2, NOX3, CAPNS1 and RHOA exemplified by SEQ ID NO:1-3, SEQ ID NO:4, SEQ ID NO:5-6 and SEQ ID NO:7, respectively. In preferred embodiments the methods and kits involve use of a dsRNA compound that binds human CASP2 mRNA set forth in any one of SEQ ID 1-3.

In preferred embodiments the CASP2 dsRNA compound comprises a sense strand and an antisense strand wherein the antisense strand comprises the nucleotide sequence (5'>3') AGGAGUUCCACAUUCUGGC (SEQ ID NO:9). In preferred embodiments the dsRNA compound has the structure:

```
                         (sense strand, SEQ ID NO: 8)
5' z"-GCCAGAAUGUGGAACUCCU-Z 3'

                     (antisense strand, SEQ ID NO: 9)
3' Z'-CGGUCUUACACCUUGAGGA 5'
```

- wherein each A, C, U, and G is an unmodified ribonucleotide, a modified ribonucleotide or an unconventional moiety and each consecutive ribonucleotide or unconventional moiety is joined to the next ribonucleotide or unconventional moiety by a covalent bond;
- wherein each of Z and Z' is independently present or absent, but if present independently includes 1-5 consecutive nucleotides or non-nucleotide moieties or a combination thereof covalently attached at the 3' terminus of the strand in which it is present; and
- wherein z" may be present or absent, but if present is a capping moiety covalently attached at the 5' terminus of the sense strand. In some embodiments the dsRNA compound comprises unmodified and modified ribonucleotides. In preferred embodiments the dsRNA compound comprises unmodified and modified ribonucleotides at least one unconventional moiety.

In some embodiments the dsRNA further comprises at least one unconventional moiety. In certain preferred embodiments the CASP2 dsRNA has the structure:

```
                    (sense strand, SEQ ID NO: 24)
5' z"-GCCAGAAUGUGGAACUCCU-Z' 3'

                 (antisense strand, SEQ ID NO: 25)
3' Z-CGGUCUUACACCUUGAGGA 5'
```

wherein each A, C, U, and G is an unmodified or modified ribonucleotide or an unconventional moiety and each consecutive ribonucleotide or unconventional moiety is joined to the next ribonucleotide or unconventional moiety by a phosphodiester bond; wherein the sense strand comprises, counting from the 5' terminus, an unmodified ribonucleotide at positions 1, 2, 3, 4, 5, 6, 7, 8, 9, 10, 11, 12, 13, 14, 15, 16, 17 and 19, a L-deoxycytidine at position 18; wherein the antisense strand comprises at least five (5) alternating unmodified and 2'-O-methyl sugar modified ribonucleotides; and wherein z", Z and Z' are optionally absent. In some embodiments, the antisense strand comprises 2'-O-methyl sugar modified ribonucleotides present in positions (5'>3') 1, 3, 5, 7 9, 11, 13, 15, 17 and 19 and unmodified ribonucleotides present in positions 2, 4, 6, 8, 10, 12, 14, 16 and 18; preferably the antisense strand comprises 2'O-methyl sugar modified ribonucleotides in positions (5'>3') 2, 4, 6, 8, 11, 13, 15, 17 and 19.

In preferred embodiments the dsRNA compound has the structure:

```
                    (sense strand, SEQ ID NO: 26)
5' iB-GCCAGAAUGUGGAACUCCU-Z' 3'

                 (antisense strand, SEQ ID NO: 27)
3' Z-CGGUCUUACACCUUGAGGA 5'
```

wherein each A, C, U, and G is an unmodified ribonucleotide, a modified ribonucleotide or an unconventional moiety and each consecutive ribonucleotide or unconventional moiety is joined to the next ribonucleotide or unconventional moiety by a covalent bond;

wherein each Z and Z' is absent, wherein the sense strand comprises, counting from the 5' terminus, an unmodified ribonucleotide at positions 1, 2, 3, 4, 5, 6, 7, 8, 9, 10, 11, 12, 13, 14, 15, 16, 17 and 19, a L-deoxycytidine at position 18 and z" is present and comprises an inverted deoxyabasic moiety; and wherein the antisense strand comprises, counting from the 5' terminus, a 2'O-methyl sugar modified ribonucleotide at each of positions 2, 4, 6, 8, 11, 13, 15, 17 and 19 and an unmodified ribonucleotide at each of positions 1, 3, 5, 7, 9, 10, 12, 14, 16 and 18. This molecule is also known as 1007.

The dsRNA compounds are administered by any of the conventional routes of administration, including involving invasive and non-invasive delivery methods. It should be noted that the dsRNA compound can be administered as the compound per se or as pharmaceutically acceptable salt and can be administered alone or as an active ingredient in combination with pharmaceutically acceptable carriers, solvents, diluents, excipients, adjuvants and vehicles.

The dsRNA compounds are preferably administered transtympanically, including topically or via injection. Liquid forms may be prepared for administration. The liquid compositions include aqueous solutions, with and without organic co-solvents, aqueous or oil suspensions, emulsions with edible oils, as well as similar pharmaceutical vehicles. In one embodiment the administration comprises topical administration, in particular topical administration to the ear canal, topical administration to the tympanic membrane, or a combination thereof, thereby allowing the dsRNA compounds to pass the tympanic membrane. In some embodiments the compounds of the present application are applied to the tympanic membrane as an eardrop. In some preferred embodiments the dsRNA compounds are administered by transtympanic injection or by eardrops.

In various embodiments, particularly embodiments in which the pharmaceutical compositions of the invention are administered topically, the pharmaceutical compositions further comprise a permeability enhancer, also known as penetration enhancer.

In various embodiments the penetration enhancer is selected from any compound or any combination of two ore more compounds that enhance the penetration of a therapeutic oligonucleotide through the tympanic membrane in the ear of a subject suffering from Ménière's disease. In certain embodiments the permeability enhancer is a polyol. In some embodiments the oligonucleotide is in admixture with a polyol. In some embodiments the polyol is selected from the group consisting of glycerol, propylene glycol, polyethylene glycol, sorbitol, xylitol, maltitol and combinations thereof.

According to one embodiment the polyol is glycerol. In various embodiments glycerol is present at a final concentration of about 0.1% to about 35%; about 1% to about 30%; about 5% to about 25%, preferably about 10% to about 20% by volume of the pharmaceutical composition.

In some embodiments, the pharmaceutical composition is applied to the ear canal when the subject's head is tilted to one side and the treated ear is facing upward. In some embodiments, the pharmaceutical composition is applied to the ear using a receptacle for liquid, for example using a dropper of for example, 10-100 microliter per drop, or a wick.

An additional embodiment of the present invention provides for the use of any of the above compositions in the preparation of a medicament for the treatment of a subject suffering from Ménière's disease. Further provided is compound that inhibits expression of CASP2 for providing neuroprotection to a neuron in an ear of a subject in need thereof.

The methods, materials, and examples that will now be described are illustrative only and are not intended to be limiting; materials and methods similar or equivalent to those described herein can be used in practice or testing of the invention. Other features and advantages of the invention will be apparent from the following detailed description, and from the claims.

This disclosure is intended to cover any and all adaptations or variations of combination of features that are disclosed in the various embodiments herein. Although specific embodiments have been illustrated and described herein, it should be appreciated that the invention encompasses any arrangement of the features of these embodiments to achieve the same purpose. Combinations of the above features, to form embodiments not specifically described herein, will be apparent to those of skill in the art upon reviewing the instant description.

BRIEF DESCRIPTION OF THE FIGURES

FIGS. 6A and 6B show disorder and death of SG in vehicle treated Phex$^{hyp-Duk}$/Y mice and FIGS. 6B and 6D show rescue of SG in siCASP2 treated Phex$^{hyp-Duk}$/Y mice. FIGS. 6E and 6F show separate histological sections of the vestibular ganglion in vehicle treated Phex$^{hyp-Duk}$/Y mice and siCASP2 treated Phex$^{hyp-Duk}$/Y mice, respectively.

DETAILED DESCRIPTION OF THE INVENTION

Figure 1:
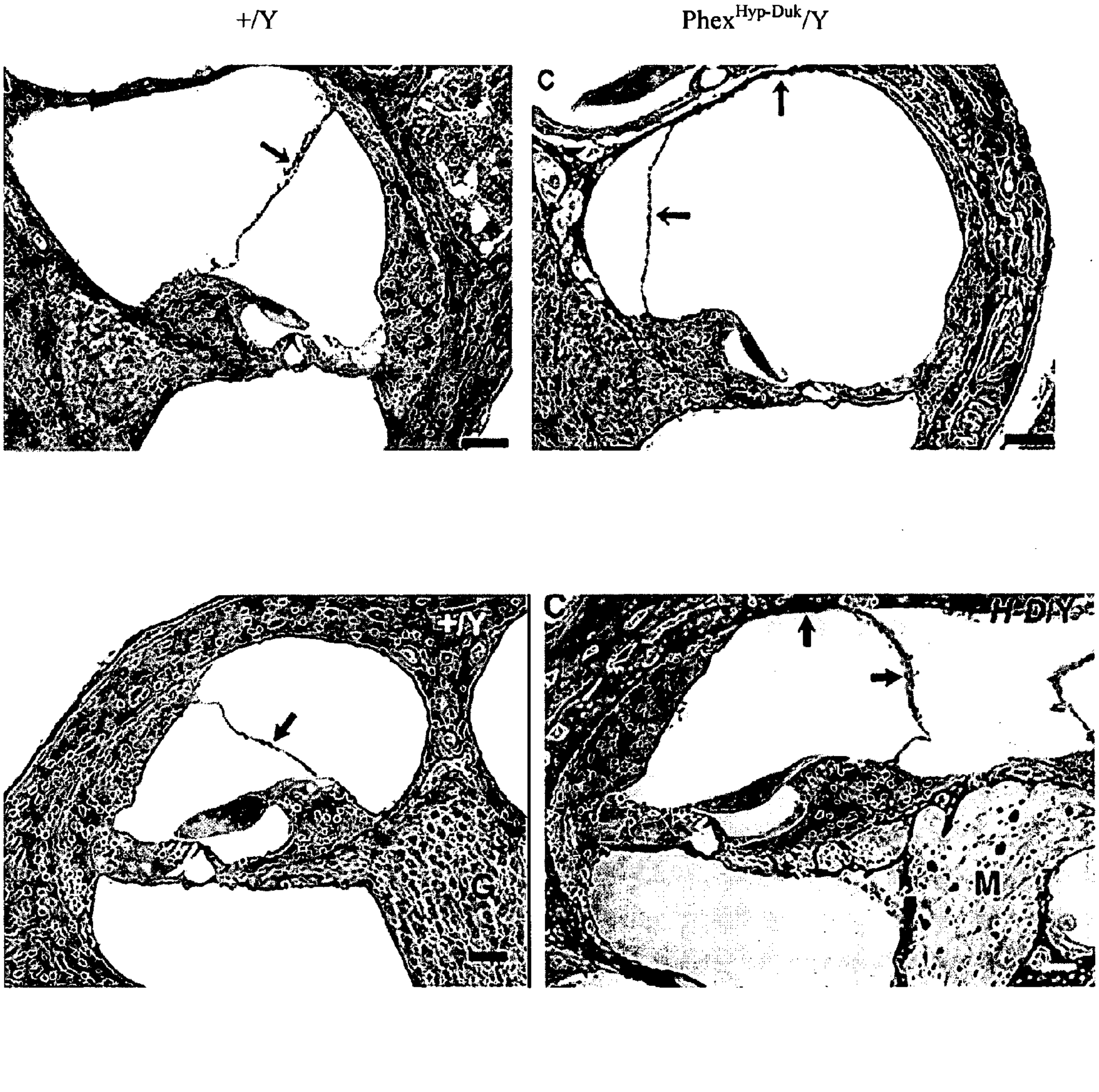
FIG. 1 shows histological sections of wild type (left panels) and Phex$^{hyp\text{-}Duk}$ mutant (right panels) inner ear tissue. Arrows show Endolymphatic hydrop (ELH). In left bottom panel, G refers to spiral ganglion neurons, and in right bottom panel M refers to mutant spiral ganglion neurons, of which there are fewer (compare G to M) in the Phex$^{hyp\text{-}Duk}$ mutant mice. Phex$^{hyp\text{-}Duk}$ mutant mice spontaneously develop endolymphatic hydrop and are thus presented with balance problems and hearing loss phenotype. One of the primary defects is the loss of neurons in the inner ear ganglia (vestibular and spiral) by cell death, or apoptosis.

The present application provides oligonucleotide molecules, compositions comprising same: methods of use thereof and kits for treating Ménière's disease and for ameliorating one or more of the attendant symptoms, including fluctuating hearing loss, episodic vertigo and/or tinnitus. The present disclosure is based in part on the finding that inhibition of any one of the target genes selected from Caspase 2 (CASP2), NADPH Oxidase 3 (NOX3), Calpain S1 (CAPNS1) and Ras homolog gene family, member A (RHOA).

In one aspect, the provided herein is a method of affording neuroprotection of spiral ganglion cells and/or vestibular ganglion cells in a subject in need thereof comprising administering to the subject a therapeutically effective amount of an oligonucleotide molecule which inhibits expression of CASP2, so as to thereby afford neuroprotection in spiral ganglion cells and/or vestibular ganglion cells. In another aspect provided herein is a method of treating a subject afflicted with Ménière's disease comprising administering to the subject an oligonucleotide molecule which inhibits expression of CASP2, so as to thereby treat the patient. Ménière's disease, also known as idiopathic endolymphatic hydrops (ELH), is a disorder of the inner ear resulting in vertigo and tinnitus, and eventual neuronal damage leading to hearing loss. The exact cause of Ménière's disease is unknown but the underlying mechanism is believed to be distortion of the membranous labyrinth due to accumulation of endolymph. Endolymph is produced primarily by the stria vascularis in the cochlea and also by the planum semilunatum and the dark cells in the vestibular labyrinth (Sajjadi H, Paparella M M. Ménière's disease. Lancet. 372(9636):406-14). Endolymphatic hydrops can occur if the flow of endolymph from the endolymphatic fluid space through the vestibular aqueduct to the endolymphatic sac is obstructed. Ménière's disease may affect one or both of a subject's ears. The primary morbidity associated with Ménière's disease is the debilitating nature of vertigo and the progressive hearing loss.

In various embodiments the methods include attenuating hearing loss in a subject. In some embodiments the methods include preventing progressive hearing loss in a subject afflicted with Ménière's disease. In some embodiments the methods include protection of spiral ganglion cells from cell death. In some embodiments the methods include protection of vestibular ganglion cells from cell death.

In a preferred embodiment the subject is a mammal, preferably a human subject.

In various embodiments the molecule that down regulates CASP2 is a Caspase2 inhibitor such as a double-stranded RNA oligonucleotide, optionally an siNA, more preferably a dsRNA molecule detailed in Table A infra and in particular, an siNA comprising the following antisense sequence 5' AGGAGUUCCACAUUCUGGC (also known as CASP2_4) and the use of this oligonucleotide in the preparation of a medicament for use in the therapy of conditions and disorders disclosed herein. In one embodiment the disorder involves spiral ganglion death or vestibular ganglion death. In some embodiments the cell death comprises apoptotic cell death.

TABLE A

Non-limiting examples of Caspase2 oligonucleotide sequences for use in the methods disclosed herein

| ID | SEQ ID NO: | Sense SEQ (5' > 3') | SEQ ID NO: | Antisense SEQ (5' > 3') | residual % |
|---|---|---|---|---|---|
| CASP2_4 | 8 | GCCAGAAUGUGGAACUCCU | 9 | AGGAGUUCCACAUUCUGGC | 11, 18 |
| CASP2_1 | 18 | GCACUCCUGAAUUUUAUCA | 19 | UGAUAAAAUUCAGGAGUGC | 12, 8 |

TABLE A-continued

Non-limiting examples of Caspase2 oligonucleotide sequences for use in the methods disclosed herein

| ID | SEQ ID NO: | Sense SEQ (5' > 3' ) | SEQ ID NO: | Antisense SEQ (5' > 3' ) | residual % |
|---|---|---|---|---|---|
| CASP2_2 | 20 | GCACAGGAAAUGCAAGAGA | 21 | UCUCUUGCAUUUCCUGUGC | 25, 38 |
| CASP2_3 | 22 | GGGCUUGUGAUAUGCACGU | 23 | ACGUGCAUAUCACAAGCCC | 22, 39 |

Additional information about these dsRNAs, as well as additional dsRNAs targeting or down regulating CASP2, NOX3 or RHOA which are useful in the present methods, are provided in PCT Publication Nos. WO 2008/050329 and WO 2010/048352. Non-limiting examples of dsRNAs targeting or down regulating CAPNS1 which are useful in the present methods, are provided in US Patent Application Publication No. 20110034534.

Without being bound by theory, CASP2 is a pro-apoptotic gene that is specifically expressed and activated in ganglion cells (GC) following axonal injury. The present Assignee has previously demonstrated that inhibition of CASP2 in rat models of optic nerve damage resulted in robust rescue of retinal ganglion cells (RGC) from apoptotic death (PMID: 21677688). In some embodiments the methods include the use of oligonucleotide molecules that down regulate or inhibit CASP2 expression. In some embodiments the methods include the use of oligonucleotide molecules that down regulate or inhibit NOX3 expression. In some embodiments the methods include the use of oligonucleotide molecules that down regulate or inhibit CAPNS1 expression. In some embodiments the methods include the use of oligonucleotide molecules that down regulate or inhibit RHOA expression

DEFINITIONS

For convenience certain terms employed in the specification, examples and claims are described herein.

It is to be noted that, as used herein, the singular forms "a", "an" and "the" include plural forms unless the content clearly dictates otherwise.

Where aspects or embodiments of the invention are described in terms of Markush groups or other grouping of alternatives, those skilled in the art will recognize that the invention is also thereby described in terms of any individual member or subgroup of members of the group.

An "inhibitor" is a compound, which is capable of reducing (partially or fully) the expression of a gene or the activity of the product of such gene to an extent sufficient to achieve a desired biological or physiological effect. The term "inhibitor" as used herein refers to a dsRNA inhibitor including a siRNA inhibitor.

As used herein, the term "inhibit", "down-regulate", or "reduce" with respect to gene expression means the expression of the gene, or level of RNA molecules or equivalent RNA molecules encoding one or more proteins or protein subunits (e.g., mRNA), or activity of one or more proteins or protein subunits, is reduced below that observed in the absence of an inhibitory factor (such as a nucleic acid molecule, e.g., an siNA, for example having structural features as described herein); for example the expression may be reduced to 90%, 80%, 70%, 60%, 50%, 40%, 30%, 20%, 10%, 5% or less than that observed in the absence of an inhibitor. In some embodiments of the methods and kits disclosed herein, down regulation of the target gene results in at least a 10% decrease in neuronal cell death in a population of neuronal cells as compared to a control population of neuronal cells.

A "double-stranded RNA inhibitor" is a compound, which is capable of reducing the expression of a gene or the activity of the product of such gene to an extent sufficient to achieve a desired biological or physiological effect. The term as used herein refers to one or more of a siRNA, shRNA, and synthetic shRNA Inhibition may also be referred to as down-regulation or, for RNAi, silencing.

The term "inhibit" as used herein refers to reducing the expression of a gene or the activity of the product of such gene to an extent sufficient to achieve a desired biological or physiological effect. Inhibition is either complete or partial. For example "inhibition" of APP gene means inhibition of the gene expression (transcription or translation) or polypeptide activity of one or more of the variants or an SNP (single nucleotide polymorphism) thereof.

SEQ ID NO:1 refers to *Homo sapiens* caspase 2, apoptosis-related cysteine peptidase (CASP2), transcript variant 1, mRNA gi|320461578|ref|NM_032982.3|;

SEQ ID NO:2 refers to *Homo sapiens* caspase 2, apoptosis-related cysteine peptidase (CASP2), transcript variant 3, mRNA gi|320461587|ref|NM_032983.3|;

SEQ ID NO:3 refers to *Homo sapiens* caspase 2, apoptosis-related cysteine peptidase (CASP2), transcript variant 2, mRNA gi|331999981|ref|NM_001224.4|;

SEQ ID NO:4 refers to *Homo sapiens* NADPH oxidase 3 (NOX3), mRNA gi|229331997|ref|NM_015718.2|;

SEQ ID NO:5 refers to *Homo sapiens* calpain, small subunit 1 (CAPNS1), transcript variant 1, mRNA gi|51599152|ref|NM_001749.2|;

SEQ ID NO:6 refers to *Homo sapiens* calpain, small subunit 1 (CAPNS1), transcript variant 2, mRNA gi|51599150|ref|NM_001003962.1|;

SEQ ID NO:7 refers to *Homo sapiens* ras homolog family member A (RHOA), mRNA gi|50593005|ref|NM_001664.2|.

One aspect of the invention includes the "neuroprotective" activity of the dsRNA disclosed herein. The method of the invention provides for the protection from injury, death or senescence of neurons or protects or improves neuronal function. As used herein, the term "neuroprotection" relates to the arrest and/or slowing and/or attenuation and/or reversing progression of neurodegeneration. As used herein, the term "neurodegeneration" means the progressive loss of neurons. This includes, but is not limited to, immediate loss of neurons followed by subsequent loss of connecting or adjacent neurons.

"Neuron," "neuronal cell" "nerve cell" and "neural cell" (including neural progenitor cells and neural stem cells) are used interchangeably to refer to nerve cells, i.e., cells that are responsible for conducting nerve impulses from one part of the body to another. Most neurons consist of three distinct portions: a cell body which contains the nucleus, and two different types of cytoplasmic processes: dendrites and axons. Dendrites, which are the receiving portion of the neuron, are usually highly branched, thick extensions of the cell body. The axon is typically a single long, thin process that is specialized to conducts nerve impulses away from the cell body to another neuron or muscular or glandular tissue. Axons may have side branches called "axon collaterals." Axon collaterals and axons may terminate by branching into many fine filaments called telodendria. The distal ends of telodendria are called synaptic end bulbs or axonal terminals, which contain synaptic vesicles that store neurotransmitters. Axons may be surrounded by a multilayered, white, phospholipid, segmented covering called the myelin sheath, which is formed by Schwann cells in the peripheral nervous system and oligodendrocytes in the central nervous system. Axons containing such a covering are "myelinated." Neurons include sensory (afferent) neurons, which transmit impulses from receptors in the periphery to the brain and spinal cord and from lower to higher centers of the central nervous system. A neuron can also be motor (efferent) neurons which convey impulses from the brain and spinal cord to effectors in the periphery and from higher to lower centers of the central nervous system. Other neurons are association (connecting or interneuron) neurons which carry impulses from sensory neurons to motor neurons and are located within the central nervous system. The processes of afferent and efferent neurons arranged into bundles are called "nerves" when located outside the CNS or fiber tracts if inside the CNS.

The term "topical administration" or "topical application" is used to mean a local administration of a composition, preferably to the ear canal of the subject but also optionally to the tympanic membrane where topical administration is relevant.

The term "otic" and "auricular" are used herein interchangeably and generally refer to tissue in and/or around an ear, including the outer ear, the middle ear and the inner ear.

The term "ear canal" or "external auditory meatus" is used to mean a tube running from the outer ear to the middle ear.

The "tympanic membrane" (also tympanum or myrinx) refers to the thin membrane that separates the external ear from the middle ear.

Terms such as "pharmaceutical composition" or "otic pharmaceutical composition" or "ocular pharmaceutical composition" "pharmaceutical formulation" or "pharmaceutical preparation" are used herein interchangeably to generally refer to formulations that are adapted to administration and delivery of one or more oligonucleotide active compounds to the ear, specifically to the tissue of the inner ear in an animal or a human.

"Treatment," "treat," or "treating," as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., attenuating or arresting or slowing down or postponing its development or progression; (c) relieving and/or ameliorating the disease or condition, i.e., causing regression of the disease or condition and/or the symptoms thereof; or (d) curing the disease or condition, i.e., stopping its development or progression. The population of subjects treated by the methods of the invention includes subjects suffering from the undesirable condition or disease, as well as subjects at risk for development of the condition or disease.

As used herein, the term "pharmaceutically acceptable" means that the components, in addition to the therapeutic agent, comprising the formulation, are suitable for administration to the patient/subject being treated in accordance with the present invention.

A "penetration enhancer" or "permeability enhancer" refers to a compound or a combination of compounds that enhance the penetration of a therapeutic oligonucleotide through the tympanic membrane in the ear of an animal or a human.

As used herein, the term "tissue" refers to an aggregation of similarly specialized cells united in the performance of a particular function.

As used herein, the terms "polynucleotide" and "nucleic acid" may be used interchangeably and refer to nucleotide sequences comprising deoxyribonucleic acid (DNA), and ribonucleic acid (RNA). The terms are to be understood to include, as equivalents, analogs of either RNA or DNA made from nucleotide analogs. Throughout this application, mRNA sequences are set forth as representing the corresponding genes.

"Oligonucleotide" and "oligomer" are used interchangeably and refer to a deoxyribonucleotide or ribonucleotide sequence from about 2 to about 50 nucleotides. Each DNA or RNA nucleotide may be independently natural or synthetic, and or modified or unmodified. Modifications include changes to the sugar moiety, the base moiety and or the linkages between nucleotides in the oligonucleotide. The compounds of the present invention encompass molecules comprising deoxyribonucleotides, ribonucleotides, modified deoxyribonucleotides, modified ribonucleotides, unconventional moieties and combinations thereof. Oligonucleotide is meant to encompass single stranded molecules including antisense and shRNA, and double-stranded molecules including double-stranded RNA (dsRNA), siNA, siRNA and miRNA.

Substantially complementary refers to complementarity of greater than about 84%, to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly substantially identical refers to identity of greater than about 84%, to another sequence. In some preferred embodiments, the sense strand and the antisense strand are fully complementary (100%). In some embodiments, the antisense strand is fully complementary (100%) to the target mRNA. In some embodiments, the sense antisense strand comprises a mismatch to the target mRNA. For example, an antisense strand with an A, C or G in the first position of the antisense strand is generated with a "U" in the first position (5'), thereby generating a mismatch between the antisense strand and the target mRNA.

"Nucleotide" is meant to encompass deoxyribonucleotides and ribonucleotides, which may be natural or synthetic, and or modified or unmodified. Modifications include changes to the sugar moiety, the base moiety and or the linkages between ribonucleotides in the oligoribonucleotide. As used herein, the term "ribonucleotide" encompasses natural and synthetic, unmodified and modified ribonucleotides. Modifications include changes to the sugar moiety, to the base moiety and/or to the linkages between ribonucleotides in the oligonucleotide.

The nucleotides can be selected from naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halo uracil, 5-halo cytosine, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine. In some embodiments one or more nucleotides in an oligomer is substituted with inosine.

In some embodiments of the present invention the inhibitory oligonucleotide compound comprises unmodified and modified nucleotides and/or unconventional moieties. The compound comprises at least one modified nucleotide selected from the group consisting of a sugar modification, a base modification and an internucleotide linkage modification and may contain DNA, and modified nucleotides such as LNA (locked nucleic acid), ENA (ethylene-bridged nucleic acid), PNA (peptide nucleic acid), arabinoside, phosphonocarboxylate or phosphinocarboxylate nucleotide (PACE nucleotide), mirror nucleotide, or nucleotides with a 6 carbon sugar.

All analogs of, or modifications to, a nucleotide/oligonucleotide are employed with the present invention, provided that said analog or modification does not substantially adversely affect the function of the nucleotide/oligonucleotide. Acceptable modifications include modifications of the sugar moiety, modifications of the base moiety, modifications in the internucleotide linkages and combinations thereof.

A sugar modification includes a modification on the 2' moiety of the sugar residue and encompasses amino, fluoro, alkoxy e.g. methoxy, alkyl, amino, fluoro, chloro, bromo, CN, CF, imidazole, carboxylate, thioate, $C_1$ to $C_{10}$ lower alkyl, substituted lower alkyl, alkaryl or aralkyl, $OCF_3$, OCN; O-, S-, or N-alkyl; O-, S, or N-alkenyl; $SOCH_3$; $SO_2CH_3$; $ONO_2$; $NO_2$, $N_3$; heterocycloalkyl; heterocycloalkaryl; aminoalkylamino; polyalkylamino or substituted silyl, as, among others, described in European patents EP 0 586 520 B1 or EP 0 618 925 B1.

In one embodiment the double-stranded RNA compound comprises at least one ribonucleotide comprising a 2' modification on the sugar moiety ("2' sugar modification"). In certain embodiments the compound comprises 2'O-alkyl or 2'-fluoro or 2'O-allyl or any other 2' modification, optionally on alternate positions. Other stabilizing modifications are also possible (e.g. terminal modifications). In some embodiments a preferred 2'O-alkyl is 2'O-methyl (methoxy) sugar modification.

In some embodiments the backbone of the oligonucleotides is modified and comprises phosphate-D-ribose entities but may also contain thiophosphate-D-ribose entities, triester, thioate, 2'-5' bridged backbone (also may be referred to as 5'-2'), PACE and the like.

As used herein, the terms "non-pairing nucleotide analog" means a nucleotide analog which comprises a non-base pairing moiety including but not limited to: 6 des amino adenosine (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, N3-Me dC. In some embodiments the non-base pairing nucleotide analog is a ribonucleotide. In other embodiments it is a deoxyribonucleotide. In addition, analogues of polynucleotides may be prepared wherein the structure of one or more nucleotide is fundamentally altered and better suited as therapeutic or experimental reagents. An example of a nucleotide analogue is a peptide nucleic acid (PNA) wherein the deoxyribose (or ribose) phosphate backbone in DNA (or RNA) is replaced with a polyamide backbone which is similar to that found in peptides. PNA analogues have been shown to be resistant to enzymatic degradation and to have enhanced stability in vivo and in vitro. Other modifications useful in synthesizing oligonucleotides include polymer backbones, cyclic backbones, acyclic backbones, thiophosphate-D-ribose backbones, triester backbones, thioate backbones, 2'-5' linked backbone (also known as 2'5' nucleotides, or 2'5' ribonucleotides [with 3'OH]), artificial nucleic acids, morpholino nucleic acids, glycol nucleic acid (GNA), threose nucleic acid (TNA), arabinoside, and mirror nucleoside (for example, beta-L-deoxyribonucleoside instead of beta-D-deoxyribonucleoside). Examples of siRNA compounds comprising LNA nucleotides are disclosed in Elmen et al., (NAR 2005, 33(1):439-447).

In some embodiments the double-stranded RNA compounds are synthesized using one or more inverted nucleotides, for example inverted thymidine or inverted adenine (see, for example, Takei, et al., 2002, JBC 277(26):23800-06).

Other modifications include terminal modifications on the 5' and/or 3' part of the oligonucleotides and are also known as capping moieties. Such terminal modifications are selected from a nucleotide, a modified nucleotide, a lipid, a peptide, a sugar and inverted abasic moiety.

What is sometimes referred to in the present invention as an "abasic nucleotide" or "abasic nucleotide analog" is more properly referred to as a pseudo-nucleotide or an unconventional moiety. A nucleotide is a monomeric unit of nucleic acid, consisting of a ribose or deoxyribose sugar, a phosphate, and a base (adenine, guanine, thymine, or cytosine in DNA; adenine, guanine, uracil, or cytosine in RNA). A modified nucleotide comprises a modification in one or more of the sugar, phosphate and or base. The abasic pseudo-nucleotide lacks a base, and thus is not strictly a nucleotide.

The term "capping moiety" as used herein ("z''") includes abasic ribose moiety, abasic deoxyribose moiety, modified abasic ribose and abasic deoxyribose moieties including 2'O alkyl modifications; inverted abasic ribose and abasic deoxyribose moieties and modifications thereof; C6-imino-Pi; a mirror nucleotide including L-DNA and L-RNA; 5'O-Me nucleotide; and nucleotide analogs including 4',5'-methylene nucleotide; 1-(β-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non bridging methylphosphonate and 5'-mercapto moieties.

Certain preferred capping moieties are abasic ribose or abasic deoxyribose moieties; inverted abasic ribose or abasic deoxyribose moieties; C6-amino-Pi; a mirror nucleotide including L-DNA and L-RNA. Another preferred capping moiety is a C3 non-nucleotide moiety derived from propanediol The term "unconventional moiety" as used herein refers to abasic ribose moiety, an abasic deoxyribose moiety, a deoxyribonucleotide, a modified deoxyribonucleotide, a mirror nucleotide, a non-base pairing nucleotide analog and a nucleotide linked to an adjacent nucleotide by a 2'-5' internucleotide phosphate bond; bridged nucleic acids including LNA and ethylene bridged nucleic acids.

In some embodiments of the present invention a preferred unconventional moiety is an abasic ribose moiety, an abasic deoxyribose moiety, a deoxyribonucleotide, a mirror nucleotide, and a nucleotide linked to an adjacent nucleotide by a 2'-5' internucleotide phosphate bond.

Abasic deoxyribose moiety includes for example abasic deoxyribose-3'-phosphate; 1,2-dideoxy-D-ribofuranose-3-phosphate; 1,4-anhydro-2-deoxy-D-ribitol-3-phosphate. Inverted abasic deoxyribose moiety includes inverted deoxyriboabasic; 3', 5' inverted deoxyabasic 5'-phosphate.

A "mirror nucleotide" is a nucleotide with reversed chirality to the naturally occurring or commonly employed nucleotide, i.e., a mirror image (L-nucleotide) of the naturally occurring (D-nucleotide), also referred to as L-RNA in the case of a mirror ribonucleotide, and "spiegelmer". The nucleotide can be a ribonucleotide or a deoxyribonucleotide and my further comprise at least one sugar, base and or backbone modification. See U.S. Pat. No. 6,586,238. Also, U.S. Pat. No. 6,602,858 discloses nucleic acid catalysts comprising at least one L-nucleotide substitution. Mirror nucleotide includes for example L-DNA (L-deoxyriboadenosine-3'-phosphate (mirror dA); L-deoxyribocytidine-3'-phosphate (mirror dC); L-deoxyriboguanosine-3'-phosphate (mirror dG); L-deoxyribothymidine-3'-phosphate (mirror image dT)) and L-RNA (L-riboadenosine-3'-phosphate (mirror rA); L-ribocytidine-3'-phosphate (mirror rC); L-riboguanosine-3'-phosphate (mirror rG); L-ribouracil-3'-phosphate (mirror rU).

Modified deoxyribonucleotide includes, for example 5'OMe DNA (5-methyl-deoxyriboguanosine-3'-phosphate) which may be useful as a nucleotide in the 5' terminal position (position number 1); PACE (deoxyriboadenine 3' phosphonoacetate, deoxyribocytidine 3' phosphonoacetate, deoxyriboguanosine 3' phosphonoacetate, deoxyribothymidine 3' phosphonoacetate).

Bridged nucleic acids include LNA (2'-O, 4'-C-methylene bridged Nucleic Acid adenosine 3' monophosphate, 2'-O,4'-C-methylene bridged Nucleic Acid 5-methyl-cytidine 3' monophosphate, 2'-O,4'-C-methylene bridged Nucleic Acid guanosine 3' monophosphate, 5-methyl-uridine (or thymidine) 3' monophosphate); and ENA (2'-O,4'-C-ethylene bridged Nucleic Acid adenosine 3' monophosphate, 2'-O,4'-C-ethylene bridged Nucleic Acid 5-methyl-cytidine 3' monophosphate, 2'-O,4'-C-ethylene bridged Nucleic Acid guanosine 3' monophosphate, 5-methyl-uridine (or thymidine) 3' monophosphate). According to one aspect the present invention provides inhibitory oligonucleotide compounds comprising unmodified and modified nucleotides. The compound comprises at least one modified nucleotide selected from the group consisting of a sugar modification, a base modification and an internucleotide linkage modification and may contain DNA, and modified nucleotides such as LNA (locked nucleic acid) including ENA (ethylene-bridged nucleic acid; PNA (peptide nucleic acid); arabinoside; PACE (phosphonoacetate and derivatives thereof), mirror nucleotide, or nucleotides with a six-carbon sugar.

Any of the modifications disclosed herein can be employed in the preparation of the oligonucleotides which are incorporated into the compositions of the present invention. Preferred modification schemes are disclosed, for examples, in PCT Publication Nos. WO 2006/023544, WO 2010/048352, WO2009/116037, WO 2009/147684, WO 2011/066475, WO 2011/084193, all assigned to the assignee of the instant invention.

Exemplary nucleic acid sequence of Caspase2 (human CASP2) mRNA are set forth in FIGS. 1A-1C, for example as listed as SEQ ID NO: 1-3. One of ordinary skill in the art would understand that a given sequence may change over time and to incorporate any changes needed in the nucleic acid molecules herein accordingly. The methods disclosed herein further encompass the use of dsRNA molecules that down regulate expression of NOX3, CAPNS1 (Calpain S1) and RHOA.

RNA Interference and siNA Nucleic Acid Molecules

RNA interference refers to the process of sequence-specific post-transcriptional gene silencing in animals mediated by short interfering RNAs (siRNAs) (Zamore et al., 2000, Cell, 101, 25-33; Fire et al., 1998, Nature, 391, 806; Hamilton et al., 1999, Science, 286, 950-951; Lin et al., 1999, Nature, 402, 128-129; Sharp, 1999, Genes & Dev., 13:139-141; and Strauss, 1999, Science, 286, 886). The corresponding process in plants (Heifetz et al., International PCT Publication No. WO 99/61631) is often referred to as post-transcriptional gene silencing (PTGS) or RNA silencing. The process of post-transcriptional gene silencing is thought to be an evolutionarily-conserved cellular defense mechanism used to prevent the expression of foreign genes (Fire et al., 1999, Trends Genet., 15, 358). Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA. The presence of dsRNA in cells triggers the RNAi response through a mechanism that has yet to be fully characterized. This mechanism appears to be different from other known mechanisms involving double-stranded RNA-specific ribonucleases, such as the interferon response that results from dsRNA-mediated activation of protein kinase PKR and 2',5'-oligoadenylate synthetase resulting in non-specific cleavage of mRNA by ribonuclease L (see for example U.S. Pat. Nos. 6,107,094; 5,898,031; Clemens et al., 1997, J. Interferon & Cytokine Res., 17, 503-524; Adah et al., 2001, Curr. Med. Chem., 8, 1189).

The presence of long dsRNAs in cells stimulates the activity of a ribonuclease III enzyme referred to as dicer (Bass, 2000, Cell, 101, 235; Zamore et al., 2000, Cell, 101, 25-33; Hammond et al., 2000, Nature, 404, 293). Dicer is involved in the processing of the dsRNA into short pieces of dsRNA known as short interfering RNAs (siRNAs) (Zamore et al., 2000, Cell, 101, 25-33; Bass, 2000, Cell, 101, 235; Berstein et al., 2001, Nature, 409, 363). Short interfering RNAs derived from dicer activity are typically about 21 to about 23 nucleotides in length and include about 19 base pair duplexes (Zamore et al., 2000, Cell, 101, 25-33; Elbashir et al., 2001, Genes Dev., 15, 188). Dicer has also been implicated in the excision of 21- and 22-nucleotide small temporal RNAs (stRNAs) from precursor RNA of conserved structure that are implicated in translational control (Hutvagner et al., 2001, Science, 293, 834). The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex (Elbashir et al., 2001, Genes Dev., 15, 188).

RNAi has been studied in a variety of systems. Fire et al., (1998, Nature, 391, 806) were the first to observe RNAi in *C. elegans*. Bahramian and Zarbl, (1999, Molecular and Cellular Biology, 19, 274-283) and Wianny and Goetz, (1999, Nature Cell Biol., 2, 70) describe RNAi mediated by dsRNA in mammalian systems. Hammond et al., (2000, Nature, 404, 293) describe RNAi in *Drosophila* cells transfected with dsRNA. Elbashir et al., (2001, Nature, 411, 494) and Tuschl et al., (PCT Publication No. WO 01/75164) describe RNAi induced by introduction of duplexes of synthetic 21-nucleotide RNAs in cultured mammalian cells including human embryonic kidney and HeLa cells. Studies in *Drosophila* embryonic lysates (Elbashir et al., 2001, EMBO J., 20, 6877) and Tuschl et al., (PCT Publication No. WO 01/75164) has revealed certain requirements for siRNA length, structure, chemical composition, and sequence that are essential to mediate efficient RNAi activity.

Nucleic acid molecules (for example having structural features as disclosed herein) may inhibit or down regulate gene expression or viral replication by mediating RNA interference "RNAi" or gene silencing in a sequence-specific manner; see e.g., Zamore et al., 2000, Cell, 101, 25-33; Bass, 2001, Nature, 411, 428-429; Elbashir et al., 2001, Nature, 411, 494-498; and Kreutzer et al., PCT Publication No. WO 00/44895; Zernicka-Goetz et al., PCT Publication No. WO 01/36646; Fire, PCT Publication No. WO 99/32619; Plaetinck et al., PCT Publication No. WO 00/01846; Mello and Fire, PCT Publication No. WO 01/29058; Deschamps-Depaillette, PCT Publication No. WO 99/07409; and Li et al., PCT Publication No. WO 00/44914; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237; Hutvagner and Zamore, 2002, Science, 297, 2056-60; McManus et al., 2002, RNA, 8, 842-850; Reinhart et al., 2002, Gene & Dev., 16, 1616-1626; and Reinhart & Bartel, 2002, Science, 297, 1831).

An siNA nucleic acid molecule can be assembled from two separate polynucleotide strands, where one strand is the sense strand and the other is the antisense strand in which the antisense and sense strands are self-complementary (i.e. each strand includes nucleotide sequence that is complementary to nucleotide sequence in the other strand); such as where the antisense strand and sense strand form a duplex or double-stranded structure having any length and structure as described herein for nucleic acid molecules as provided, for example wherein the double-stranded region (duplex region) is about 15 to about 49 (e.g., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 base pairs); the antisense strand includes nucleotide sequence that is complementary to nucleotide sequence in a target nucleic acid molecule (i.e., mRNA) or a portion thereof and the sense strand includes nucleotide sequence corresponding to the target nucleic acid sequence or a portion thereof (e.g., about 17 to about 49 or more nucleotides of the nucleic acid molecules herein are complementary to the target nucleic acid or a portion thereof).

In certain aspects and embodiments a nucleic acid molecule (e.g., a siNA molecule) provided herein may be a "RISC length" molecule or may be a Dicer substrate as described in more detail below. Longer molecules such as pre-miRNA can also work in RISC.

A siNA nucleic acid molecule may include separate sense and antisense sequences or regions, where the sense and antisense regions are covalently linked by nucleotide or non-nucleotide linkers molecules as is known in the art, or are alternately non-covalently linked by ionic interactions, hydrogen bonding, van der Waals interactions, hydrophobic interactions, and/or stacking interactions. Nucleic acid molecules may include a nucleotide sequence that is complementary to nucleotide sequence of a target gene. Nucleic acid molecules may interact with nucleotide sequence of a target gene in a manner that causes inhibition of expression of the target gene.

Alternatively, a siNA nucleic acid molecule is assembled from a single polynucleotide, where the self-complementary sense and antisense regions of the nucleic acid molecules are linked by means of a nucleic acid based or non-nucleic acid-based linker(s), i.e., the antisense strand and the sense strand are part of one single polynucleotide that having an antisense region and sense region that fold to form a duplex region (for example to form a "hairpin" structure as is well known in the art). Such siNA nucleic acid molecules can be a polynucleotide with a duplex, asymmetric duplex, hairpin or asymmetric hairpin secondary structure, having self-complementary sense and antisense regions, wherein the antisense region includes nucleotide sequence that is complementary to nucleotide sequence in a separate target nucleic acid molecule or a portion thereof and the sense region having nucleotide sequence corresponding to the target nucleic acid sequence (e.g., a sequence of mRNA). Such siNA nucleic acid molecules can be a circular single-stranded polynucleotide having two or more loop structures and a stem comprising self-complementary sense and antisense regions, wherein the antisense region includes nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active nucleic acid molecule capable of mediating RNAi.

The following nomenclature is often used in the art to describe lengths and overhangs of siNA molecules and may be used throughout the specification and Examples. Names given to duplexes indicate the length of the oligomers and the presence or absence of overhangs. For example, a "21+2" duplex contains two nucleic acid strands both of which are 21 nucleotides in length, also termed a 21-mer siRNA duplex or a 21-mer nucleic acid and having a 2 nucleotides 3'-overhang. A "21−2" design refers to a 21-mer nucleic acid duplex with a 2 nucleotides 5'-overhang. A 21−0 design is a 21-mer nucleic acid duplex with no overhangs (blunt). A "21+2UU" is a 21-mer duplex with 2-nucleotides 3'-overhang and the terminal 2 nucleotides at the 3'-ends are both U residues (which may result in mismatch with target sequence). The aforementioned nomenclature can be applied to siNA molecules of various lengths of strands, duplexes and overhangs (such as 19−0, 21+2, 27+2, and the like). In an alternative but similar nomenclature, a "25/27" is an asymmetric duplex having a 25 base sense strand and a 27 base antisense strand with a 2-nucleotides 3'-overhang. A "27/25" is an asymmetric duplex having a 27 base sense strand and a 25 base antisense strand.

Chemical Modifications

In certain aspects and embodiments, nucleic acid molecules (e.g., dsRNA including siNA molecules) as provided herein include one or more modifications (or chemical modifications), including the presence of one or more unconventional moieties. In certain embodiments, such modifications include any changes to a nucleic acid molecule or polynucleotide that would make the molecule different than a standard ribonucleotide or RNA molecule (i.e., that includes standard adenine, cytosine, uracil, or guanine moieties); which may be referred to as an "unmodified" ribonucleotide or unmodified ribonucleic acid. Traditional DNA bases and polynucleotides having a 2'-deoxy sugar represented by adenine, cytosine, thymine, or guanine moieties may be referred to as an "unmodified deoxyribonucleotide" or "unmodified deoxyribonucleic acid"; accordingly, the term "unmodified nucleotide" or "unmodified nucleic acid" as used herein refers to an "unmodified ribonucleotide" or "unmodified ribonucleic acid" unless there is a clear indication to the contrary. Such modifications can be in the nucleotide sugar, nucleotide base, nucleotide phosphate group, and/or the phosphate backbone of a polynucleotide and include enantiomers of RNA and DNA.

In certain embodiments modifications as disclosed herein may be used to increase RNAi activity of a molecule and/or to increase the in vivo stability of the molecules, particularly the stability in serum, and/or to increase bioavailability of the molecules. Non-limiting examples of modifications include without limitation internucleotide or internucleoside linkages; deoxyribonucleotides or dideoxyribonucleotides at any position and strand of the nucleic acid molecule; nucleic acid (e.g., ribonucleic acid) with a modification at the 2'-position preferably selected from an amino, fluoro, methoxy, alkoxy and alkyl; 2'-deoxyribonucleotides, 2'-O-methyl ribonucleotides, 2'-deoxy-2'-fluoro ribonucleotides, "universal base" nucleotides, "acyclic" nucleotides, 5-C-methyl nucleotides, biotin group, and terminal glyceryl and/or inverted deoxy abasic residue incorporation, sterically hindered molecules, such as fluorescent molecules and the like. Other nucleotides modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidi-ne (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). Further details on various modifications are described in more detail below.

Modified nucleotides include those having a Northern conformation (e.g., Northern pseudorotation cycle, see for example Saenger, Principles of Nucleic Acid Structure, Springer-Verlag ed., 1984). Non-limiting examples of nucleotides having a northern configuration include locked nucleic acid (LNA) nucleotides (e.g., 2'-O, 4'-C-methylene-(D-ribofuranosyl) nucleotides); 2'-methoxyethoxy (MOE) nucleotides; 2'-methyl-thio-ethyl, 2'-deoxy-2'-fluoro nucleotides, 2'-deoxy-2'-chloro nucleotides, 2'-azido nucleotides, and 2'-β-methyl nucleotides. Locked nucleic acids, or LNAs are described, for example, in Elman et al., 2005; Kurreck et al., 2002; Crinelli et al., 2002; Braasch and Corey, 2001; Bondensgaard et al., 2000; Wahlestedt et al., 2000; and Patent Publication Nos. WO 00/47599, WO 99/14226, and WO 98/39352 and WO 2004/083430. In one embodiment, an LNA is incorporated at the 5' terminus of the sense strand.

Chemical modifications also include unlocked nucleic acids, or UNAs, which are non-nucleotide, acyclic analogues, in which the C2'-C3' bond is not present (although UNAs are not truly nucleotides, they are expressly included in the scope of "modified" nucleotides or modified nucleic acids as contemplated herein). In particular embodiments, nucleic acid molecules with an overhang may be modified to have UNAs at the overhang positions (i.e., 2 nucleotide overhand). In other embodiments, UNAs are included at the 3'- or 5'-ends. A UNA may be located anywhere along a nucleic acid strand, i.e. at position 7. Nucleic acid molecules may contain one or more than UNA. Exemplary UNAs are disclosed in Nucleic Acids Symposium Series No. 52 p. 133-134 (2008). In certain embodiments a nucleic acid molecule (e.g., a siNA molecule) as described herein include one or more UNAs; or one UNA. In some embodiments, a nucleic acid molecule (e.g., a siNA molecule) as described herein that has a 3'-overhang include one or two UNAs in the 3' overhang. In some embodiments a nucleic acid molecule (e.g., a siNA molecule) as described herein includes a UNA (for example one UNA) in the antisense strand; for example in position 6 or position 7 of the antisense strand. Chemical modifications also include non-pairing nucleotide analogs, for example as disclosed herein. Chemical modifications further include unconventional moieties as disclosed herein.

Chemical modifications also include terminal modifications on the 5' and/or 3' part of the oligonucleotides and are also known as capping moieties. Such terminal modifications are selected from a nucleotide, a modified nucleotide, a lipid, a peptide, and a sugar.

Chemical modifications also include six membered "six membered ring nucleotide analogs." Examples of six-membered ring nucleotide analogs are disclosed in Allart, et al (Nucleosides & Nucleotides, 1998, 17:1523-1526; and Perez-Perez, et al., 1996, Bioorg. and Medicinal Chem Letters 6:1457-1460) Oligonucleotides including 6-membered ring nucleotide analogs including hexitol and altritol nucleotide monomers are disclosed in patent application publication No. WO 2006/047842.

Chemical modifications also include "mirror" nucleotides, which have a reversed chirality as compared to normal naturally occurring nucleotide; that is a mirror nucleotide may be an "L-nucleotide" analogue of naturally occurring D-nucleotide (see U.S. Pat. No. 6,602,858). Mirror nucleotides may further include at least one sugar or base modification and/or a backbone modification, for example, as described herein, such as a phosphorothioate or phosphonate moiety. U.S. Pat. No. 6,602,858 discloses nucleic acid catalysts including at least one L-nucleotide substitution. Mirror nucleotides include for example L-DNA (L-deoxyriboadenosine-3'-phosphate (mirror dA); L-deoxyribocytidine-3'-phosphate (mirror dC); L-deoxyriboguanosine-3'-phosphate (mirror dG); L-deoxyribothymidine-3'-phosphate (mirror image dT)) and L-RNA (L-riboadenosine-3'-phosphate (mirror rA); L-ribocytidine-3'-phosphate (mirror rC); L-riboguanosine-3'-phosphate (mirror rG); L-ribouracil-3'-phosphate (mirror dU).

In some embodiments, modified ribonucleotides include modified deoxyribonucleotides, for example 5'OMe DNA (5-methyl-deoxyriboguanosine-3'-phosphate) which may be useful as a nucleotide in the 5' terminal position (position number 1); PACE (deoxyriboadenine 3' phosphonoacetate, deoxyribocytidine 3' phosphonoacetate, deoxyriboguanosine 3' phosphonoacetate, deoxyribothymidine 3' phosphonoacetate.

Modifications may be present in one or more strands of a nucleic acid molecule disclosed herein, e.g., in the sense strand, the antisense strand, or both strands. In certain embodiments, the antisense strand may include modifications and the sense strand my only include unmodified RNA.

Nucleobases

Nucleobases of the nucleic acid disclosed herein may include unmodified ribonucleotides (purines and pyrimidines) such as adenine, guanine, cytosine, uridine. The nucleobases in one or both strands can be modified with natural and synthetic nucleobases such as thymine, xanthine, hypoxanthine, inosine, 2-aminoadenine, 6-methyl and other alkyl derivatives of adenine and guanine, any "universal base" nucleotides; 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 8-halo, amino, thiol, thioalkyl, hydroxyl and other 8-substituted adenines and guanines, 5-trifluoromethyl and other 5-substituted uracils and cytosines, 7-methylguanine, deazapurines, heterocyclic substituted analogs of purines and pyrimidines, e.g., aminoethyoxy phenoxazine, derivatives of purines and pyrimidines (e.g., 1-alkyl-, 1-alkenyl-, heteroaromatic- and 1-alkynyl derivatives) and tautomers thereof, 8-oxo-$N^6$-methyladenine, 7-diazaxanthine, 5-methylcytosine, 5-methyluracil, 5-(1-propynyl)uracil, 5-(1-propynyl)cytosine and 4,4-ethanocytosine). Other examples of suitable bases include non-purinyl and non-pyrimidinyl bases such as 2-aminopyridine and triazines.

Sugar Moieties

Sugar moieties in nucleic acid disclosed herein may include 2'-hydroxyl-pentofuranosyl sugar moiety without any modification. Alternatively, sugar moieties can be modified such as, 2'-deoxy-pentofuranosyl sugar moiety, D-ribose, hexose, modification at the 2' position of the pentofuranosyl sugar moiety such as 2'-O-alkyl (including 2'-O-methyl and 2'-O-ethyl), i.e., 2'-alkoxy, 2'-amino, 2'-O-allyl, 2'-S-alkyl, 2'-halogen (including 2'-fluoro, chloro, and bromo), 2'-methoxyethoxy, 2'-O-methoxyethyl, 2'-O-2-methoxyethyl, 2'-allyloxy ($—OCH_2CH═CH_2$), 2'-propargyl, 2'-propyl, ethynyl, propenyl, CF, cyano, imidazole, carboxylate, thioate, $C_1$ to $C_{10}$ lower alkyl, substituted lower alkyl, alkaryl or aralkyl, $OCF_3$, OCN, O-, S-, or N-alkyl; O-, S, or N-alkenyl; $SOCH_3$; $SO_2CH_3$; $ONO_2$; $NO_2$, $N_3$; heterozycloalkyl; heterozycloalkaryl; aminoalkylamino; polyalkylamino or substituted silyl, as, among others, for example as described in European patents EP 0 586 520 B1 or EP 0 618 925 B1.

Alkyl group includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls may have from 3-8 carbon atoms in their ring structure, and more preferably have 5 or 6 carbons in the ring structure. The term $C_1$-$C_6$ includes alkyl groups containing 1 to 6 carbon atoms. The alkyl group can be substituted alkyl group such as alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Alkoxy group includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

In some embodiments, the pentafuronosyl ring may be replaced with acyclic derivatives lacking the C2'-C3'-bond of the pentafuronosyl ring. For example, acyclonucleotides may substitute a 2-hydroxyethoxymethyl group for-the 2'-deoxyribofuranosyl sugar normally present in dNMPs.

Halogens include fluorine, bromine, chlorine, iodine.

Backbone

The nucleoside subunits of the nucleic acid disclosed herein may be linked to each other by phosphodiester bond. The phosphodiester bond may be optionally substituted with other linkages. For example, phosphorothioate, thiophosphate-D-ribose entities, triester, thioate, 2'-5' bridged backbone (may also be referred to as 5'-2'), PACE, 3'-(or -5') deoxy-3'-(or -5')thio-phosphorothioate, phosphorodithioate, phosphoroselenates, 3'-(or -5')deoxy phosphinates, borano phosphates, 3'-(or -5')deoxy-3'-(or 5'-)amino phosphoramidates, hydrogen phosphonates, phosphonates, borano phosphate esters, phosphoramidates, alkyl or aryl phosphonates and phosphotriester modifications such as alkylphosphotriesters, phosphotriester phosphorus linkages, 5'-ethoxyphosphodiester, P-alkyloxyphosphotriester, methylphosphonate, and nonphosphorus containing linkages for example, carbonate, carbamate, silyl, sulfur, sulfonate, sulfonamide, formacetal, thioformacetyl, oxime, methyleneimino, methylenemethylimino, methylenehydrazo, methylenedimethylhydrazo and methyleneoxymethylimino linkages.

Nucleic acid molecules disclosed herein may include a peptide nucleic acid (PNA) backbone. The PNA backbone is includes repeating N-(2-aminoethyl)-glycine units linked by peptide bonds. The various bases such as purine, pyrimidine, natural and synthetic bases are linked to the backbone by methylene carbonyl bonds.

Terminal Phosphates

Modifications can be made at terminal phosphate groups. Non-limiting examples of different stabilization chemistries can be used, e.g., to stabilize the 3'-end of nucleic acid sequences, including (1) [3-3']-inverted deoxyribose; (2) deoxyribonucleotide; (3) [5'-3']-3'-deoxyribonucleotide; (4) [5'-3']-ribonucleotide; (5) [5'-3']-3'-O-methyl ribonucleotide; (6) 3'-glyceryl; (7) [3'-5']-3'-deoxyribonucleotide; (8) [3'-3']-deoxyribonucleotide; (9) [5'-2']-deoxyribonucleotide; and (10) [5-3']-dideoxyribonucleotide. In addition to unmodified backbone chemistries can be combined with one or more different backbone modifications described herein.

Exemplary chemically modified terminal phosphate groups include those shown below:

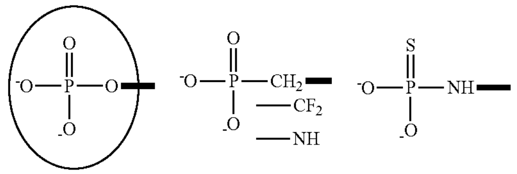

-continued

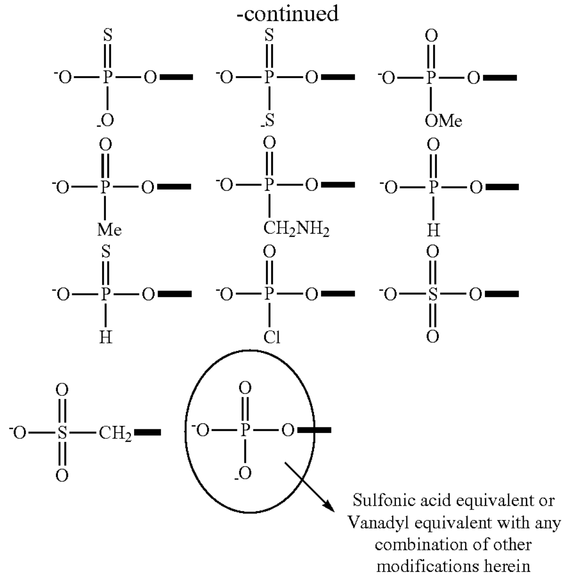

In one aspect, provided are double-stranded nucleic acid molecules for use in neuroprotection of neurons in the ear of a subject having the structure (A1):

```
(A1)
(antisense strand)
5' (N)x—Z 3'

(sense strand)
3' Z'-(N')y—z" 5'
```

wherein each of N and N' is a nucleotide which may be unmodified or modified, or an unconventional moiety;

wherein each of (N)x and (N')y is an oligonucleotide in which each consecutive N or N' is joined to the next N or N' by a covalent bond; wherein each of Z and Z' is independently present or absent, but if present independently includes 1-5 consecutive nucleotides or non-nucleotide moieties or a combination thereof covalently attached at the 3' terminus of the strand in which it is present;

wherein z" may be present or absent, but if present is a capping moiety covalently attached at the 5' terminus of (N') y; each of x and y is independently an integer from 18 to 40;

wherein the sequence of (N')y has complementarity to the sequence of (N)x; and wherein (N)x includes an antisense sequence to the target mRNA, wherein the target mRNA comprises a sequence set forth in any one of SEQ ID NO:1-3, SEQ ID NO:4, SEQ ID NO:5-6 or SEQ ID NO:7.

In some embodiments x=y and each of x and y is 19, 20, 21, 22 or 23. In various embodiments x=y=19. In some embodiments the antisense and sense strands form a duplex by base pairing. In some embodiments (N)x and $(N')_y$ are oligonucleotide pairs provided in PCT Patent Publication Nos. WO 2008/050329, WO 2009/044392, WO 2008/106102, WO 2009/001359, WO/2009/090639 incorporated herein by reference in their entirety.

In some embodiments x=y and each of x and y is 19, 20, 21, 22 or 23. In various embodiments x=y=19. In some embodiments the antisense and sense strands form a duplex by base pairing According to one embodiment provided are modified nucleic acid molecules for use in neuroprotection of neurons in the ear of a subject having a structure (A2) set forth below:

```
(A2)
(antisense strand)
5' N1-(N)x-Z 3'

(sense strand)
3' Z'-N2-(N')y—z" 5'
```

wherein each of N2, N and N' is independently an unmodified or modified nucleotide, or an unconventional moiety;

wherein each of (N)x and (N')y is an oligonucleotide in which each consecutive N or N' is joined to the adjacent N or N' by a covalent bond;

wherein each of x and y is independently an integer of from 17 to 39;

wherein the sequence of $(N')_y$ has complementarity to the sequence of (N)x and (N)x has complementarity to a consecutive sequence in a target mRNA;

wherein N1 is covalently bound to (N)x and is mismatched to the target mRNA, wherein the target mRNA is set forth in any one of SEQ ID NO:1-3, SEQ ID NO:4, SEQ ID NO:5-6 or SEQ ID NO:7;

wherein N1 is a moiety selected from the group consisting of uridine, modified uridine, ribothymidine, modified ribothymidine, deoxyribothymidine, modified deoxyribothymidine, riboadenine, modified riboadenine, deoxyriboadenine or modified deoxyriboadenine;

wherein N1 and N2 form a base pair;

wherein each of Z and Z' is independently present or absent, but if present is independently 1-5 consecutive nucleotides or non-nucleotide moieties or a combination thereof covalently attached at the 3' terminus of the strand in which it is present; and wherein z" may be present or absent, but if present is a capping moiety covalently attached at the 5' terminus of (N')y.

In some embodiments the covalent bond joining each consecutive N or N' is a phosphodiester bond.

In some embodiments Z and Z' are absent. In other embodiments one of Z or Z' is present and comprises non-nucleotide overhang moieties as disclosed in PCT patent publication no. WO/2011/085056, incorporated herein by reference in its entirety.

In specific embodiments of Structure A1 x=y=19 and Z comprises at least one C3 alkyl overhang. In specific embodiments of Structure A2 x=y=18 and Z comprises at least one C3 alkyl overhang. In some embodiments the C3-C3 overhang is covalently attached to the 3' terminus of (N)x or (N')y via a covalent linkage, preferably a phosphodiester linkage. In some embodiments the linkage between a first C3 and a second C3 is a phosphodiester linkage. In some embodiments the 3' non-nucleotide overhang is C3Pi-C3Pi. In some embodiments the 3' non-nucleotide overhang is C3Pi-C3Ps. In some embodiments the 3' non-nucleotide overhang is C3Pi-C3OH(OH is hydroxy). In some embodiments the 3' non-nucleotide overhang is C3Pi-C3OH.

In various embodiments the alkyl moiety comprises an alkyl derivative including a C3 alkyl, C4 alkyl, C5 alky or C6 alkyl moiety comprising a terminal hydroxyl, a terminal amino, or terminal phosphate group. In some embodiments the alkyl moiety is a C3 alkyl or C3 alkyl derivative moiety. In some embodiments the C3 alkyl moiety comprises propanol, propylphosphate, propylphosphorothioate or a combination thereof. The C3 alkyl moiety is covalently linked to the 3' terminus of (N')y and/or the 3' terminus of (N)x via a phosphodiester bond. In some embodiments the alkyl moiety comprises propanol, propyl phosphate or propyl phosphorothioate. In some embodiments each of Z and Z' is independently selected from propanol, propyl phosphate propyl phosphorothioate, combinations thereof or multiples thereof in particular 2 or 3 covalently linked propanol, propyl phosphate, propyl phosphorothioate or combinations thereof. In some embodiments each of Z and Z' is independently selected from propyl phosphate, propyl phosphorothioate, propyl phospho-propanol; propyl phospho-propyl phosphorothioate; propylphospho-propyl phosphate; (propyl phosphate)3, (propyl phosphate)2-propanol, (propyl phosphate)2-propyl phosphorothioate. Any propane or propanol conjugated moiety can be included in Z or Z'.

The structures of exemplary 3' terminal non-nucleotide moieties are as follows:

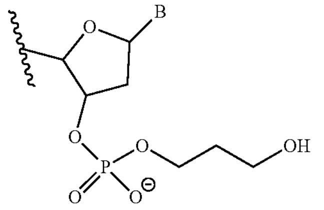

3′ terminus-C3-OH

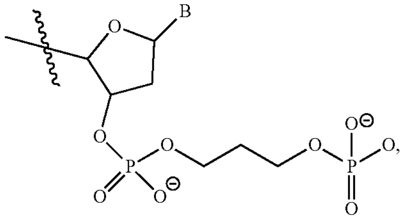

3′ terminus-C3Pi

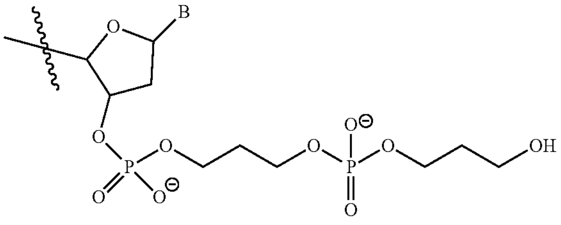

3′ terminus-C3Pi-C3OH

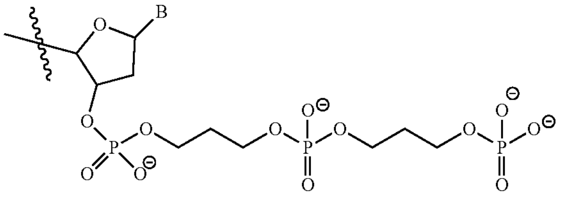

3′ terminus-C3Pi-C3Pi

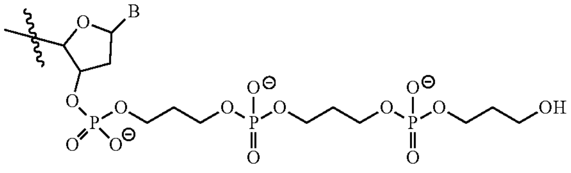

3′ terminus-C3Pi-C3Pi-C3OH

In some embodiments the 5' terminal nucleotide of the antisense strand (position 1 of the antisense strand) is mismatched to the target mRNA. In some embodiments the 5' terminal nucleotide of the antisense strand is a modified riboadenosine or a modified ribouridine.

In some embodiments each of (N)), and $(N')_y$ is independently phosphorylated or non-phosphorylated at the 3' and 5' termini.

Unless otherwise indicated, in preferred embodiments of the structures discussed herein the covalent bond between each consecutive N and N' is a phosphodiester bond.

A covalent bond refers to an internucleotide linkage linking one nucleotide monomer to an adjacent nucleotide monomer. A covalent bond includes for example, a phosphodiester bond, a phosphorothioate bond, a P-alkoxy bond, a P-carboxy bond and the like. The normal internucleoside linkage of RNA and DNA is a 3' to 5' phosphodiester linkage. In certain preferred embodiments a covalent bond is a phosphodiester bond. Covalent bond encompasses non-phosphorous-containing internucleoside linkages, such as those disclosed in WO 2004/041924 inter alia. Unless otherwise indicated, in preferred embodiments of the structures discussed herein the covalent bond between each consecutive N and N' is a phosphodiester bond.

For all of the structures above, in some embodiments the oligonucleotide sequence of (N)x is fully complementary to the oligonucleotide sequence of (N')y. In other embodiments (N)x and (N')y are substantially complementary. In certain embodiments (N)x is fully complementary to 18-40 consecutive nucleotides in a target mRNA. In other embodiments (N)x is substantially complementary to 18-40 consecutive nucleotides in a target mRNA.

In some embodiments, neither (N)x nor (N')y are phosphorylated at the 3' and 5' termini. In other embodiments either or both (N)x and (N')y are phosphorylated at the 3' termini (3' Pi). In yet another embodiment, either or both (N)x and (N')y are phosphorylated at the 3' termini with non-cleavable phosphate groups. In yet another embodiment, either or both (N)x and (N')y are phosphorylated at the terminal 2' termini position using cleavable or non-cleavable phosphate groups. Further, the inhibitory nucleic acid molecules of the present invention may comprise one or more gaps and/or one or more nicks and/or one or more mismatches. Without wishing to be bound by theory, gaps, nicks and mismatches have the advantage of partially destabilizing the nucleic acid/siRNA, so that it may be more easily processed by endogenous cellular machinery such as DICER, DROSHA or RISC into its inhibitory components.

Synthesis of Double-Stranded RNA Compounds

The double-stranded RNA compounds useful in preparation of the pharmaceutical compositions of present invention are synthesized by any of the methods that are well known in the art for synthesis of ribonucleic (or deoxyribonucleic) oligonucleotides. Such synthesis is, among others, described in Beaucage and Iyer, *Tetrahedron* 1992; 48:2223-2311; Beaucage and Iyer, *Tetrahedron* 1993; 49: 6123-6194 and Caruthers, et. al., Methods Enzymol. 1987; 154: 287-313; the synthesis of thioates is, among others, described in Eckstein, Ann. Rev. Biochem. 1985; 54: 367-402, the synthesis of RNA molecules is described in Sproat, in Humana Press 2005 edited by Herdewijn P.; Kap. 2: 17-31 and respective downstream processes are, among others, described in Pingoud et al., in IRL Press 1989 edited by Oliver R. W. A.; Kap. 7: 183-208.

Other synthetic procedures are known in the art, e.g. the procedures described in Usman et al., 1987, J. Am. Chem. Soc., 109, 7845; Scaringe et al., 1990, NAR., 18, 5433; Wincott et al., 1995, NAR. 23, 2677-2684; and Wincott et al., 1997, Methods Mol. Bio., 74, 59, may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired.

The oligonucleotides useful in preparation of the pharmaceutical compositions of the present invention can be synthesized separately and joined together post-synthetically, for example, by ligation (Moore et al., 1992, Science 256, 9923; Draper et al., Patent Publication No. WO 93/23569; Shabarova et al., 1991, NAR 19, 4247; Bellon et al., 1997, Nucleosides & Nucleotides, 16, 951; Bellon et al., 1997, Bioconjugate Chem. 8, 204), or by hybridization following synthesis and/or deprotection.

It is noted that a commercially available machine (available, inter alia, from Applied Biosystems) can be used; the oligonucleotides are prepared according to the sequences disclosed herein. Overlapping pairs of chemically synthesized fragments can be ligated using methods well known in the art (e.g., see U.S. Pat. No. 6,121,426). The strands are synthesized separately and then are annealed to each other in the tube. Then, the double-stranded siRNAs are separated from the single-stranded oligonucleotides that were not annealed (e.g. because of the excess of one of them) by HPLC. In relation to the siRNAs or siRNA fragments of the present invention, two or more such sequences can be synthesized and linked together for use in the present invention.

The double-stranded RNA compounds useful in preparation of the pharmaceutical compositions of the invention can also be synthesized via tandem synthesis methodology, as described for example in US Patent Publication No. US 2004/0019001, wherein both siRNA strands are synthesized as a single contiguous oligonucleotide fragment or strand separated by a cleavable linker which is subsequently cleaved to provide separate siRNA fragments or strands that hybridize and permit purification of the siRNA duplex. The linker is selected from a polynucleotide linker or a non-nucleotide linker.

The compositions of the present invention preferably comprise two or more oligonucleotides, these oligos may be synthesized separately and either mixed together or (covalently or non-covalently) joined together post-synthesis, or synthesized together according to the processes detailed above.

Pharmaceutical Compositions

While it is possible for the oligonucleotide compounds of the present invention to be administered as the raw chemical, it is preferable to present them as a pharmaceutical composition. In some embodiments the oligoribonucleotide compounds are produced by endogenous intracellular complexes.

Pharmaceutical compositions disclosed herein are prepared using any chemically modified or non-modified double-stranded RNA oligonucleotide compound. siRNA which are Dicer substrates or asymmetric siRNA may be used with the invention. Double-stranded RNA oligonucleotide compounds used in the present invention encompass any pharmaceutically acceptable salts, esters, or salts of such esters, or any other compound which, upon administration to an mammal, including a human, is capable of treating diseases, disorders and injury of the ear. The term "pharmaceutically acceptable salts" refers to physiologically and pharmaceutically acceptable salts, i.e., salts that retain the desired biological activity of the parent compound and do not impart undesired toxicological effects thereto. In some embodiments pharmaceutical compositions of the invention are prepared using double-stranded RNA compounds that are chemically and or structurally modified according to one of the following modifications set forth in Structures disclosed herein or as tandem siRNA or RNAstar (see WO 2007/091269). Certain preferred molecules are chemically synthesized and modified dsRNA molecules that target CASP2, NOX3, CAPNS1 or RHOA. A certain preferred molecule is a dsRNA utilizing the CASP2_4 oligonucleotide sequence.

The invention further provides a pharmaceutical composition comprising one or more inhibitory oligonucleotide compounds; a permeability enhancer and a pharmaceutically acceptable vehicle or carrier. In some embodiments the composition comprises a mixture of two or more different oligonucleotides/siRNA compounds.

The compounds can be administered orally, subcutaneously or parenterally including intravenous, intraarterial, intramuscular, intraperitoneally, intranasal, transtympanic, as well as intrathecal and infusion techniques. Implants of the compounds are also useful. The preferable administration mode is transtympanic. Liquid forms may be prepared for injection, the term including subcutaneous, transdermal, intravenous, intramuscular, intrathecal, transtympanic injection and other parental routes of administration. The liquid compositions include aqueous solutions, with and without organic co-solvents, aqueous or oil suspensions, emulsions with edible oils, as well as similar pharmaceutical vehicles. In one embodiment, the administration comprises intravenous administration. In preferred embodiments the administration comprises topical administration, in particular topical administration to the ear canal, topical administration to the tympanic membrane, or a combination thereof. In some embodiments the compounds of the present application are applied to the tympanic membrane as an eardrop. In some preferred embodiments the dsRNA molecules are administered by transtympanic injection or by eardrops.

In various embodiments, particularly embodiments in which the pharmaceutical compositions of the invention are administered topically, the pharmaceutical compositions further comprise a permeability enhancer, also known as penetration enhancer. In various embodiments the penetration enhancer is selected from any compound or any combination of two ore more compounds that enhance the penetration of a therapeutic oligonucleotide through the skin and/or the tympanic membrane in the ear of a subject suffering from or at risk of a disease, a disorder or an injury of the inner ear, preferably Ménière's disease. In some embodiments the penetration/permeability enhancer is selected from, without being limited to, polyethylene glycol (PEG), glycerol (glycerin), maltitol, sorbitol etc.; diethylene glycol monoethyl ether, azone, benzalkonium chloride (ADBAC), cetylperidium chloride, cetylmethylammonium bromide, dextran sulfate, lauric acid, menthol, methoxysalicylate, oleic acid, phosphatidylcholine, polyoxyethylene, polysorbate 80, sodium glycholate, sodium lauryl sulfate, sodium salicylate, sodium taurocholate, sodium taurodeoxycholate, sulfoxides, sodium deoxycholate, sodium glycodeoxycholate, sodium taurocholate and surfactants such as sodium lauryl sulfate, laureth-9, cetylpyridinium chloride and polyoxyethylene monoalkyl ethers, benzoic acids, such as sodium salicylate and methoxy salicylate, fatty acids, such as lauric acid, oleic acid, undecanoic acid and methyl oleate, fatty alcohols, such as octanol and nonanol, laurocapram, cyclodextrins, thymol, limonene, urea, chitosan and other natural and synthetic polymers.

In certain embodiments the permeability enhancer is a polyol. In some embodiments the oligonucleotide is in admixture with a polyol. Suitable polyols for inclusion in the solutions of the invention include glycerol and sugar alcohols such as sorbitol, mannitol or xylitol, polyethylene glycol and derivatives thereof.

In some embodiments the pharmaceutical compositions of the present invention also include one or more of various other pharmaceutically acceptable ingredients, such as, without being limited to, one ore more of buffering agent, preservative, surfactant, carrier, solvent, diluent, co-solvent, viscosity building/enhancing agent, excipient, adjuvant and vehicle. In certain embodiments accepted preservatives such as benzalkonium chloride and disodium edetate (EDTA) are included in the compositions of the invention in concentrations sufficient for effective antimicrobial action, about 0.0001 to 0.1%, based on the weight of the composition.

According to one embodiment, the polyol is glycerol. In various embodiments, glycerol is present at a final concentration of about 0.1% to about 35%; about 1% to about 30%; about 5% to about 25%, preferably about 10% to about 20% by volume of the pharmaceutical composition. In some embodiments, the final concentration of glycerol in the pharmaceutical composition is about 2%, 2.5%, 5%, 10%, 12.5%, 15%, 17.5%, 20%, 22.5%, 25%, 27.5% or about 30% by volume of the pharmaceutical composition. In one embodiment, the final concentration of glycerol in the pharmaceutical composition is about 2% by volume of the pharmaceutical composition. In another embodiment, the final concentration of glycerol in the pharmaceutical composition is about 5% or about 10% by volume of the pharmaceutical composition. In yet another embodiment, the final concentration of glycerol in the pharmaceutical composition is about 20% by volume of the pharmaceutical composition. In some embodiments the pharmaceutical composition is brought to about the subject's body temperature, which is about 30° C. to about 38° C., prior to application. Certain methods for treating otic disorders are disclosed in PCT patent publication no. WO 2011/072091, incorporated herein by reference in its entirety.

In various embodiments the oligonucleotide compositions are formulated for topical administration by any suitable mode of administration. Suitable modes of administration of the pharmaceutical compositions of the invention include invasive and non-invasive modes of administration, such as without being limited to, instillation (for example, of an ear drop solution), injection (of injectable formulation), deposition (of solid or semi-solid formulation, e.g. ointment, gel), infusion or spraying. In certain embodiments, the compositions of the present invention are administered topically. Delivery can be effected by any mean (e.g. drops, spray), using any effective instrument for placing the composition inside the inner ear or for injecting the composition (e.g. through the tympanic membrane).

The present invention also provides for a process for preparing a pharmaceutical composition of the invention, in accordance with formulation techniques known to those skilled in the art. In some embodiments the process for preparing a pharmaceutical composition of the invention comprises combining, in any suitable order, a therapeutically effective amount of at least one oligonucleotide compound, one or more permeability enhancer and at least one pharmaceutically acceptable excipient or carrier, or mixtures thereof, such a composition preferably having extended chemical and/or physical stability as described herein. In some embodiments the process for preparing a pharmaceutical composition of the invention, comprises combining, in any suitable order, a therapeutically effective amount of at least one oligonucleotide compound, one or more permeability enhancer, at least one pharmaceutically acceptable excipient or carrier, or mixtures thereof and an antibacterial agent and/or preservative. In some embodiments, the pharmaceutical composition includes a pharmacologically acceptable surfactant to assist in dissolving the double-stranded RNA compound. In certain embodiments, a pharmaceutical composition of the invention further comprises an additional therapeutically active agent, such compositions being useful in combination therapies as described herein. In some embodiments of the invention the additional pharmaceutically active agent, is selected from, without being limited to, such as non-steroidal anti-inflammatory drugs, corticosteroids, antifungal, antibiotics, and the like.

In another aspect, the present invention provides a pharmaceutical composition according to the present invention for treating Ménière's disease, for attenuating one or more of the symptoms selected from the group consisting of tinnitus, EHL, episodic vertigo and hearing loss; for attenuating progressive hearing loss, for providing neuroprotection of spiral ganglion cells, for affording neuroprotection of vestibular ganglion cells, for preventing apoptotic cell death in spiral ganglion cells and for preventing apoptotic cell death in vestibular ganglion cells.

Compositions for improved delivery of the molecules disclosed herein include conjugation of double-stranded RNA molecules to a targeting molecule. The conjugate is usually formed through a covalent attachment of the targeting molecule to the sense strand of the double-stranded RNA, so as not to disrupt silencing activity. Potential targeting molecules useful in the present invention include proteins, peptides and aptamers, as well as natural compounds, such as e.g. cholesterol. For targeting antibodies, conjugation to a protamine fusion protein has been used (see for example: Song et al., Antibody mediated in vivo delivery of small interfering RNAs via cell-surface receptors, Nat. Biotechnol. 2005. 23(6):709-17).

Also provided are kits, containers and formulations that include a nucleic acid molecule (e.g., an siNA molecule) as provided herein for reducing expression of CASP2, NOX3, CAPNS1 for administering or distributing the nucleic acid molecule to a patient. A kit may include at least one container and at least one label. Suitable containers include, for example, bottles, vials, syringes, and test tubes. The containers can be formed from a variety of materials such as glass, metal or plastic. Kits may further include associated indications and/or directions; reagents and other compositions or tools used for such purpose can also be included.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be a nucleic acid molecule capable of specifically binding and/or modulating the function of CASP2, NOX3, CAPNS1.

A kit may further include a second container that includes a pharmaceutically-acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

The units dosage ampoules or multidose containers, in which the nucleic acid molecules are packaged prior to use, may include an hermetically sealed container enclosing an amount of dsRNA or solution containing a dsRNA suitable for a pharmaceutically effective dose thereof, or multiples of an effective dose. The dsRNA is packaged as a sterile formulation, and the hermetically sealed container is designed to preserve sterility of the formulation until use.

The container in which the dsRNA including a sequence encoding a cellular immune response element or fragment thereof may include a package that is labeled, and the label may bear a notice in the form prescribed by a governmental agency, for example the Food and Drug Administration, which notice is reflective of approval by the agency under Federal law, of the manufacture, use, or sale of the polynucleotide material therein for human administration.

Federal law requires that the use of pharmaceutical compositions in the therapy of humans be approved by an agency of the Federal government. In the United States, enforcement is the responsibility of the Food and Drug Administration, which issues appropriate regulations for securing such approval, detailed in 21 U.S.C. §301-392. Regulation for biologic material, including products made from the tissues of animals is provided under 42 U.S.C. §262. Similar approval is required by most foreign countries. Regulations vary from country to country, but individual procedures are well known to those in the art and the compositions and methods provided herein preferably comply accordingly.

Administration

The methods disclosed herein include administration and dosing of molecules in accordance with good medical practice, taking into account the clinical condition of the individual patient, the disease to be treated, the site and method of administration, scheduling of administration, patient age, sex, body weight and other factors known to medical practitioners.

A "therapeutically effective dose" or a "therapeutic effective amount" refers to an amount of a pharmaceutical compound or composition which is effective to achieve an improvement in a subject or his physiological systems including, but not limited to, improved survival rate, more rapid recovery, suppressed progress of the disease, or improvement or elimination of symptoms, and other indicators as are selected as appropriate determining measures by those skilled in the art.

A "therapeutically effective dose" or a "therapeutic effective amount" for purposes herein is thus determined by such considerations as are known in the art. The dose must be effective to achieve improvement including but not limited to improved survival rate or more rapid recovery, or improvement or elimination of symptoms and other indicators as are selected as appropriate measures by those skilled in the art. The pharmaceutical compositions of the invention are administered in a single dose or in multiple doses.

Dosage is determined, inter alia, by the activity of the oligonucleotide, the indication and the severity of the disorder and comprises administering a dose of about 0.1 ng to about 10 mg, about 1 ng to about 1 mg, or about 10 ng to about 1 mg, total oligonucleotide in pharmaceutically acceptable excipient or carrier. The concentration of double-stranded RNA compound in the composition is between 0.1 mg/ml to 100 mg/ml, preferably between 1 mg/ml to 100 mg/ml, and more preferably between 5 mg/ml to 20 mg/ml.

In some embodiments the active dose of oligonucleotide compound for humans is in the range of from 1 ng/kg to about 20-100 mg/kg body weight per day, preferably about 0.01 mg to about 2-10 mg/kg body weight per day, in a regimen of a single dose or multiple doses administered in one dose per day or twice or three or more times per day for a period of 1-4 weeks or longer, or even for the life of the subject.

The pharmaceutical compositions of the present invention are administered to the subject by any suitable mode of administration. Suitable modes of administration of the oligonucleotide compositions of the invention include invasive and non-invasive mode of administration, such as without being limited to, instillation (of ear drops), injection, deposition, or spraying into the ear. In certain embodiments, the compositions of the present invention are administered topically into the ear canal as ear drops or injected through a cannula into the ear canal or injected through the tympanic membrane (transtympanic injection). In many cases, the mode of administration may depend on many factors, including without being limited to, the affected ear the nature and severity of the disease or condition or injury being treated, as well as other clinical conditions of the individual subject.

In various embodiments the pharmaceutical compositions of the invention are delivered in an amount effective to provide a protective or therapeutic effect. Examples of protective or therapeutic effects include inhibition of target protein expression or knockdown of at least one target gene. In certain embodiments inhibiting expression of at least one target gene confers upon the cells and/or tissues of neuroprotective properties.

Accordingly, the pharmaceutical compositions of the invention are administered in any form that allows the active ingredient(s) (i.e. at least one oligonucleotide compound) to prevent, suppress, ameliorate, or otherwise treat the diseases and conditions disclosed herein. By way of non-limiting example, the pharmaceutical compositions can be formulated as a cream, foam, paste, ointment, emulsion, liquid solution, gel, spray, suspension, microemulsion, microspheres, microcapsules, nanospheres, nanoparticles, lipid vesicles, liposomes, polymeric vesicles, patches, biological inserts, aerosol, polymeric or polymeric-like material and/or any other form known in the art, including any form suitable for known or novel pharmaceutical delivery systems or devices, such as a removable and/or absorbable, dissolvable, and/or degradable implant. Sterile liquid pharmaceutical compositions, solutions or suspensions can be utilized invasively, for example, by intravitreal or transtympanic injection; or topically, e.g. by ear drop, ear foam, spray, gel, cream, or ointment. The liquid compositions include aqueous solutions, with and without organic co-solvents, aqueous or oil suspensions, emulsions e.g. with edible oils, as well as similar pharmaceutical vehicles.

Ear Diseases and Disorders

Disclosed herein are methods and kits useful for neuroprotection of neurons in the ear of a subject. The methods and kits are useful in providing neuroprotection of spiral ganglia thereby attenuating or preventing cochlear functions including progressive hearing loss and tinnitus. Neurons may be protected from various insults including injury or damage caused by trauma, ischemia, a chemical agent (e.g. an ototoxin), an infectious agent, an immunologic reaction or a nutritional imbalance. In some embodiments provided herein is a method for reducing the loss of neuron cells in a spiral ganglion and/or a vestibular ganglion of a subject suffering from a disease associated with pathological abnormalities or changes in the tissues of the auditory system and/or vestibular system, comprising administering to the subject's ear a dose of a double-stranded RNA (dsRNA) compound which down regulates expression of a CASP2 gene, a NOX3 gene, a CAPNS1 gene or RHOA gene so as to thereby provide neuroprotection to the spiral ganglion cells and/or the vestibular ganglion cells in the subject's ear. In some embodiments said administering results in at least 10% decrease in death of nerve cells in a population of nerve cells as compared to a control population of nerve cells. In various embodiments the abnormalities or changes are particularly associated with pathological abnormalities/changes of the tissues of the auditory organ and/or pathological abnormalities/changes of the tissues of the vestibular organs, such changes being for example, neuronal degradation or neuronal cell death. In some embodiments the dsRNA compound down regulates the CASP2 gene and comprises a sense strand with a nucleotide sequence set forth in SEQ ID NO:8 and an antisense strand with a nucleotide sequence set forth in SEQ ID NO:9, preferably a sense strand forth in SEQ ID NO:24 or 26 and an antisense strand set forth in SEQ ID NO:25 or 27.

In some embodiments the methods disclosed herein include the preventing, treating or alleviating the effects of an otic disease associated with pathological abnormalities/changes in the tissues of the auditory system and/or vestibular system in a subject, comprising administering to the subject's ear a dose of a double-stranded RNA (dsRNA) compound which down regulates expression of a CASP2 gene, a NOX3 gene, a CAPNS1 gene or RHOA gene, so as to thereby provide neuroprotection to the spiral ganglion cells and/or the vestibular ganglion cells in the subject's ear. In some embodiments said administering results in at least 10% decrease in death of nerve cells in a population of nerve cells as compared to a control population of nerve cells. In various embodiments the abnormalities or changes are particularly associated with pathological abnormalities/changes of the tissues of the auditory organ and/or pathological abnormalities/changes of the tissues of the vestibular organs, such changes being for example, neuronal degradation or neuronal cell death. In some embodiments the dsRNA compound down regulates the CASP2 gene and comprises a sense strand with a nucleotide sequence set forth in SEQ ID NO:8 and an antisense strand with a nucleotide sequence set forth in SEQ ID NO:9, preferably a sense strand set forth in SEQ ID NO:24 or 26 and an antisense strand set forth in SEQ ID NO:25 or 27.

By "ototoxin" in the context disclosed herein is meant a substance that through its chemical action injures, impairs or inhibits the activity of the neurons related to hearing or balance, which in turn impairs hearing and/or balance. Ototoxins include therapeutic drugs including antineoplastic agents, salicylates, loop-diuretics, quinines, and aminoglycoside antibiotics, contaminants in foods or medicinals, and environmental or industrial pollutants.

Accordingly, in one aspect provided are methods and kits for providing neuroprotection to a neuron in the ear of a subject, thereby to prevent, reduce, or treat a hearing impairment, disorder or imbalance, for example an ototoxin-induced hearing impairment, disorder or imbalance, by administering to the subject a dsRNA as disclosed herein.

Ototoxic aminoglycoside antibiotics include but are not limited to neomycin, paromomycin, ribostamycin, lividomycin, kanamycin, amikacin, tobramycin, viomycin, gentamicin, sisomicin, netilmicin, streptomycin, dibekacin, fortimicin, and dihydrostreptomycin, or combinations thereof. Particular antibiotics include neomycin B, kanamycin A, kanamycin B, gentamicin C1, gentamicin C1a, and gentamicin C2, and the like that are known to have serious toxicity, particularly ototoxicity and nephrotoxicity, which reduce the usefulness of such antimicrobial agents.

Ototoxicity is also a serious dose-limiting side-effect for anti-cancer agents. Ototoxic neoplastic agents include but are not limited to vincristine, vinblastine, cisplatin and cisplatin-like compounds and taxol and taxol-like compounds. Cisplatin-like compounds include carboplatin (Paraplatin®), tetraplatin, oxaliplatin, aroplatin and transplatin inter alia and are platinum based chemotherapeutics.

Diuretics with known ototoxic side-effect, particularly "loop" diuretics include, without being limited to, furosemide, ethacrylic acid, and mercurials.

Ototoxic quinines include but are not limited to synthetic substitutes of quinine that are typically used in the treatment of malaria. In some embodiments the hearing disorder is side-effect of inhibitors of type 5 phosphodiesterase (PDE-5), including sildenafil (Viagra®), vardenafil (Levitra®) and tadalafil (Clalis).

Salicylates, such as aspirin, have ototoxic side effects including tinnitus ("ringing in the ears") and temporary hearing loss. Moreover, if the drug is used at high doses for a prolonged time, the hearing impairment can become persistent and irreversible.

Further disclosed herein are methods and kits useful in providing neuroprotection to neurons of the ear wherein the neurons are damaged by mechanical or physical trauma.

In various embodiments provided herein is a method for neuroprotection of a vestibular ganglion in the ear of a subject. The methods and kits are useful in providing neuroprotection of vestibular ganglia, thereby attenuating or preventing vestibular functions including but not limited to nausea, loss of balance or vertigo. The vestibular sensory system in most mammals, including humans, contributes to balance, and to a sense of spatial orientation and stability.

Ménière's Disease

Ménière's disease, also known as idiopathic endolymphatic hydrops (ELH), is a disorder of the inner ear resulting in vertigo and tinnitus, and eventual neuronal damage leading to hearing loss. The cause of Ménière's disease remains unclear. It is characterized cochleovestibular dysfunction and by endolymphatic hydrops (post-mortem examination). The primary signs and symptoms of Ménière's disease are:

a) Episodic vertigo. Episodes of vertigo typically occur without warning and usually last from about 20 minutes to two hours or more, up to 24 hours. Severe vertigo can cause nausea and vomiting.
b) Hearing loss. Hearing loss in Ménière's disease may fluctuate, particularly early in the course of the disease. Eventually, most people experience some degree of permanent hearing loss. Hearing loss can be unilateral or bilateral.
c) Tinnitus. Tinnitus is the perception of a ringing, buzzing, roaring, whistling or hissing sound in your ear. With Ménière's disease, tinnitus is often low-pitched.
d) Aural fullness. Aural fullness is the feeling of fullness or pressure in the ear.

Without wishing to be bound to theory it is generally accepted that cochlear hair cells and vestibular hair cells die in Ménière's patients, thereby cause hearing loss. Hair cells are the sensory receptors located within the inner ear. Auditory hair cells are located in the organ of Corti of the cochlea and are involved in detecting sounds and converting sound into electrical signals that are sent via nerve fibers to the brain. Vestibular hair cells are located in the vestibular (balance) organs of the inner ear (utricle, saccule, ampullae). They detect changes in head position and send signals to the brain to help maintain body posture, eye position and balance. In the absence of auditory or vestibular hair cells, the energy derived from sound waves or gravity is not converted into neural signals, and hearing or balance deficits ensue.

In preferred embodiments the subject being treated is a warm-blooded animal and, in particular a mammal, and preferably a human.

"Treating a subject" refers to administering to the subject a therapeutic substance effective to alleviate or attenuate symptoms associated with a disease or condition, to delay the onset of the disease, to slow disease progression, to lessen the severity or cure the disease, or to prevent the disease from occurring. "Treatment" refers to both therapeutic treatment and prophylactic or preventative measures, wherein the object is to prevent a disorder, to slow the progress of a disease or to reduce the symptoms of a disorder. Those in need of treatment include those already experiencing the disease or condition, those at risk of or prone to having the disease or condition, and those in which the disease or condition is to be prevented. The compositions of the invention are administered before, during or subsequent to the onset of Ménière's disease.

Provided herein is a method for reducing the loss of neuron cells in a spiral ganglion and/or a vestibular ganglion of a subject suffering from a disease associated with pathological abnormalities in the auditory system and/or vestibular system, comprising administering to the subject's ear a dose of a double-stranded RNA (dsRNA) compound which down regulates expression of a CASP2 gene, wherein the gene encodes a mRNA set forth in any one of SEQ ID NO:1-3 so as to thereby provide neuroprotection to the spiral ganglion cells and/or the vestibular ganglion cells in the subject's ear. In preferred embodiments the dsRNA compound comprises a sense strand with a nucleotide sequence set forth in SEQ ID NO:8 and an antisense strand with a nucleotide sequence set forth in SEQ ID NO:9.

Combination Therapy

The methods for treating Ménière's disease and related diseases and disorders as disclosed herein include administering a double-stranded RNA compound directed to CASP2 gene. Further disclosed is combination therapies comprising known treatments for treating a subject suffering from or affected by or susceptible to Ménière's disease, in conjunction with the novel pharmaceutical compositions and therapies described herein are considered part of the current invention.

By "in conjunction with" or "in combination with" is meant that the additional pharmaceutically effective compound is administered prior to, at the same time as, or subsequent to administration of the pharmaceutical compositions of present invention. The individual components of such a combination referred to above, therefore, are administered either sequentially or simultaneously from the same or separate pharmaceutical formulations. A second therapeutic agent is administered by any suitable route, for example, by ocular, otic, oral, buccal, inhalation, sublingual, rectal, vaginal, transurethral, nasal, topical, percutaneous (i.e., transdermal), or parenteral (including intravenous, intramuscular, subcutaneous, and intracoronary) administration.

In some embodiments, molecule disclosed herein and the second therapeutic agent/composition are administered by the same route, either provided in a single composition or as two or more different pharmaceutical compositions. However, in other embodiments, a different route of administration for the novel pharmaceutical compositions of the invention and the second therapeutic composition/agent is either possible or preferred. Persons skilled in the art are aware of the best modes of administration for each therapeutic agent, either alone or in combination.

The invention has been described in an illustrative manner, and it is to be understood that the terminology used is intended to be in the nature of words of description rather than of limitation.

Many modifications and variations of the present invention are possible in light of the above teachings. It is, therefore, to be understood that within the scope of the appended claims, the invention can be practiced otherwise than as specifically described.

Throughout this application, various publications, including United States patents, are referenced by author and year and patents by number. The disclosures of these publications and patents and patent applications in their entireties are hereby incorporated by reference into this application in order to more fully describe the state of the art to which this invention pertains.

The present invention is illustrated in detail below with reference to examples, but is not to be construed as being limited thereto.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

General Methods—Molecular Biology and Immunoassays

Standard molecular biology protocols known in the art not specifically described herein are generally followed essentially as in Sambrook et al., *Molecular cloning: A laboratory manual*, Cold Springs Harbor Laboratory, New-York (1989, 1992), and in Ausubel et al., *Current Protocols in Molecular Biology*, John Wiley and Sons, Baltimore, Md. (1988), and as in Ausubel et al., *Current Protocols in Molecular Biology*, John Wiley and Sons, Baltimore, Md. (1989) and as in Perbal, *A Practical Guide to Molecular Cloning*, John Wiley & Sons, New York (1988), and as in Watson et al., *Recombinant DNA*, Scientific American Books, New York and in Birren et al (eds) *Genome Analysis: A Laboratory Manual Series*, Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out as discussed in *PCR Protocols: A Guide To Methods And Applications*, Academic Press, San Diego, Calif. (1990). In situ PCR in combination with Flow Cytometry (FACS) can be used for detection of cells containing specific DNA and mRNA sequences (Testoni et al., Blood 1996, 87:3822.) Methods of performing qPCR and RT-PCR are well known in the art.

Standard organic synthesis protocols known in the art not specifically described herein are generally followed essentially as in *Organic syntheses*: Vol. 1-79, editors vary, J. Wiley, New York, (1941-2003); Gewert et al., *Organic synthesis workbook*, Wiley-VCH, Weinheim (2000); Smith & March, *Advanced Organic Chemistry*, Wiley-Interscience; 5th edition (2001).

Standard medicinal chemistry methods known in the art not specifically described herein are generally followed essentially as in the series "Comprehensive Medicinal Chemistry", by various authors and editors, published by Pergamon Press.

In general, ELISA is a preferred immunoassay. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, *Molecular Cloning: A Laboratory Manual*, Cold Springs Harbor, N.Y., 1989.

siRNA Activity

The sense and antisense sequences useful in generating active and therapeutically useful dsRNA are generated using a proprietary algorithm or an algorithm known in the art.

In general, about 1.5-2×10$^5$ tested cells (HeLa cells and/or 293T cells for siRNA targeting human genes and NRK52 (normal rat kidney proximal tubule cells) cells and/or NMuMG cells (mouse mammary epithelial cell line) for siRNA targeting the rat/mouse gene) are seeded per well in 6 wells plate (70-80% confluent).

About 24 hours later, cells are transfected with siRNA compounds using the Lipofectamine™ 2000 reagent (Invitrogen) at final concentrations of 5 nM or 20 nM. The cells are incubated at 37° C. in a $CO_2$ incubator for 72 h.

As positive control for transfection PTEN-Cy3 labeled siRNA compounds are used. Various chemically modified siRNA compounds are tested for activity. GFP siRNA compounds are used as negative control for siRNA activity.

At 72 h after transfection cells are harvested and RNA is extracted from cells. Transfection efficiency is tested by fluorescent microscopy.

The percent of inhibition of gene expression using specific preferred siRNA structures is determined using qPCR analysis of the Casp2 gene in cells expressing the endogenous gene.

In general, the siRNAs having specific sequences that are selected for in vitro testing are specific for human and a second species such as non-human primate, rat or rabbit genes.

Serum Stability Experiments

Chemically modified siRNA compounds according to the present invention are tested for duplex stability in human serum, as follows:

siRNA molecules at final concentration of 7 uM are incubated at 37° C. in 100% human serum (Sigma Cat#H4522). (siRNA stock 100 uM diluted in human serum 1:14.29).

5 ul are added to 15 ul 1.5×TBE-loading buffer at different time points (0, min, 1 h, 3 h, 6 h, 8 h, 10 h, 16 h and 24 h). Samples are immediately frozen in liquid nitrogen and were kept at −20° C.

Each sample is loaded onto a non-denaturing 20% acrylamide gel, prepared according to methods known in the art. The oligos are visualized with ethidium bromide under UV light.

Example 1

Expression of CASP2 in the Mouse Inner Ear

The Phex$^{hyp\text{-}Duk}$ genetic murine model mimics the symptoms of Ménière's disease in humans including endolymphatic hydrops (ELH) and progressive hearing loss. This model is detailed in Megerian et al ("A mouse model with postnatal endolymphatic hydrops and hearing loss", Hearing Res 2008; 237(1-2):90-105), hereby incorporated by reference in its entirety. Immediately after birth, the mutant mice spontaneously develop ELH accompanied by vestibular function impairment, followed by apoptosis of neurons in the vestibular and spiral ganglia. Finally, sensory cells in both vestibular and cochlear compartments degenerate and progressive hearing loss and balance deterioration sets in.

Expression of CASP2 in the mouse inner ear was assessed in wild type and Phex$^{hyp\text{-}Duk}$ mice. Casp2 protein level was qualitatively evaluated in 2 individual experiments that included 3-week old, 2-month old and 3-month old wild type and Phex$^{hyp\text{-}Duk}$ mutant male mice. Inner ears of mice were dissected, fixed, embedded in paraffin and sectioned to obtain slides with representation of auditory and vestibular compartments as well as of spiral ganglion. The slides were used for histological evaluation. Three slides per ear were used for in situ hybridization analysis of dsRNA distribution in the inner ear. Casp2 protein expression was assessed by immunohistochemistry of the slides using Casp2 antibody (Santa Cruz, SC-623), and the HRP signals were amplified with Tyramid Amplification System (TSA™, PerkinElmer).

Casp2 positive cells were observed in all samples, specifically staining organ of Corti (OC) in the hair cells, the spiral ganglion (SG), the cochlear nerve and the vestibular sensory epithelium (macula). In addition, in a few samples non-specific staining occurred in the bone lacunae (probably bone marrow) and in blood vessels (endothelial cells). No differences between mutant and wild type were observed in Casp2 precursor protein levels, in the tested ages. Staining results are provided herein below in Table 1.

TABLE 1

CASP2 expression pattern in inner ears of wild type and Phex$^{hyp\text{-}Duk}$ mutant mice.

| | Sample name | Staining pattern |
|---|---|---|
| 1 | 3 wks Phex/Y #S515 | Organ of corti (OC)-hair cells spiral ganglion (SG) and vestibular sensory epithelium (macula) |
| 2 | 3 wks Phex/Y #S517 | OC-hair cells, Reissner's membrane and SG. |
| 3 | 3 wks +/Y #S518 | OC-hair cells, SG and in the vestibular sensory epithelium (macula) |
| 4 | 3 wks +/Y #S519 | OC-hair cells, SG and vestibular sensory epithelium (macula) |
| 5 | 2 Mo Phex/Y #S77 | OC-hair cells, SG and cochlear nerve |
| 6 | 2 Mo +/Y #S79 | OC-hair cells, SG and cochlear nerve |
| 7 | 3 Mo Phex/Y #S100 | OC-hair cells and SG (damage in tissue morphology) |
| 8 | 3 Mo Phex/Y #S99 | OC-hair cells and SG (damage in tissue morphology) |
| 9 | 3 Mo +/Y #S104 | OC-hair cells, SG and vestibular sensory epithelium (macula) |
| 10 | 3 Mo +/Y #S105 | OC-hair cells, SG, vestibular sensory epithelium (macula) and cochlear nerve |

Example 2

Evaluation of siRNA Delivery to Mouse Inner Ear and Efficacy of Four siRNA Molecules in the Phex$^{hyp\text{-}Duk}$/Y Mice, a Model of Ménière's Disease Objective: A mouse model of Ménière's Disease (MD), was used to evaluate safety and potential therapeutic effects of several dsRNA molecules for silencing of four target genes.

The Phex$^{hyp\text{-}Duk}$ genetic murine model mimics the symptoms of Ménière's disease in humans including endolymphatic hydrops (ELH) and progressive hearing loss. This model is detailed in Megerian et al ("A mouse model with postnatal endolymphatic hydrops and hearing loss", Hearing Res 2008; 237(1-2):90-105) hereby incorporated by reference in its entirety.

Assessment of safety and therapeutic effects of the dsRNA in the inner ear were performed by:

Evaluation of Ecog Performance status;

Evaluation of histological sections of the inner ear;

Evaluation of inner ear function (bilateral);

Non-invasive hearing tests;

Auditory-Evoked Brainstem Response (ABR) at Click, 8, 16 and 32 Hz;

Distortion Product Otoacoustic Emissions (DPOAE)—amplitudes at 4, 6, 8, 10, 12, 14, 16, 18 and 20 kHz;

Non-invasive vestibular function tests;

Vestibular evoked myogenic potential.

The study was carried out in two stages:

Study 1. Pilot dsRNA inner ear delivery and safety study in normal wild type mice.

Study 2. Evaluation of the therapeutic effect of dsRNA molecules targeting four different genes in male Phex$^{hyp\text{-}Duk}$/Y mice.

Figure 2:
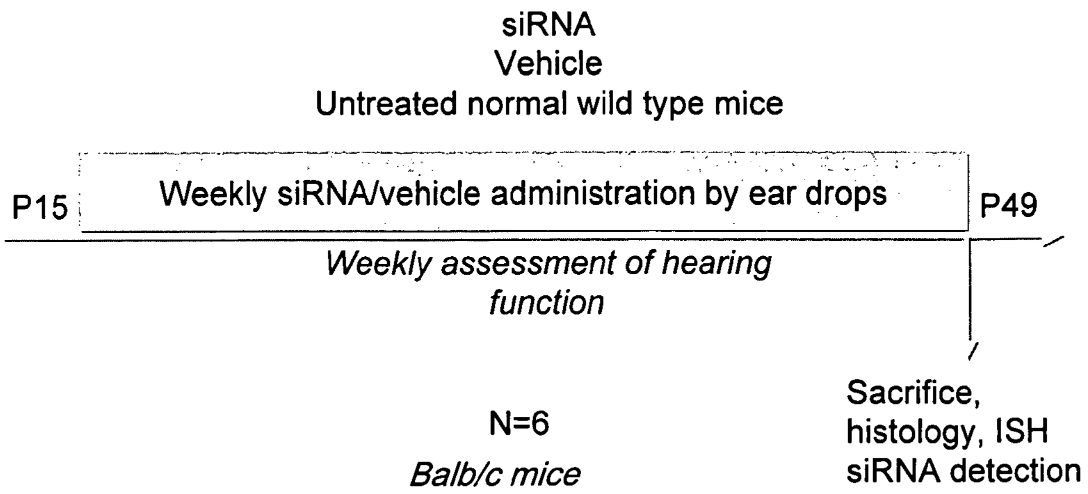
FIG. 2 shows experimental design of safety assessment of siRNA by eardrops delivery. "Px" refers to x days postpartum.

Objectives of Study 1: non-invasive inner ear delivery using eardrops and assessment of safety of multiple dsRNA administrations to the inner ear in mice. Study 1: The study design is shown in Table 2 and in FIG. 2.

TABLE 2

Study 1 design

| Group (n = 3) | Article | Treatment frequency* | Functional tests | Termi-nation |
|---|---|---|---|---|
| 1 | siRNA | P15 | None | P16 |
| 2 | siRNA | P15, P22 | P22 | P23 |
| 3 | siRNA | P15, P22, P29 | P29 | P30 |
| 4 | siRNA | P15, P22, P29, P36 | P36 | P37 |
| 5 | siRNA | P15, P22, P29, P36, P42 | P42 | P43 |
| 6 | siRNA | P15, P22, P29, P36, P42, P49 | P49 | P50 |
| 7 | vehicle | P15, P22, P29, P36, P42, P49 | P49 | P50 |
| 8 | Intact | None | P22, P29, P36, P42, P49 | P50 |

*P = days postnatal, i.e. P15 refers to 15 days postnatal.

dsRNA or vehicle was delivered on a weekly basis to 7 groups of 3 mice each starting from P15. Functional tests were performed on the day before the last administration of test or control article and prior to their administration. Administration of dsRNA molecules requires animal immobilization (anesthesia) for 40-60 minutes. Therefore, optimization of the schedule of functional test performance requiring anesthesia was performed. Functional tests in intact non-treated mice of the same age served as baseline control.

Figure 3:
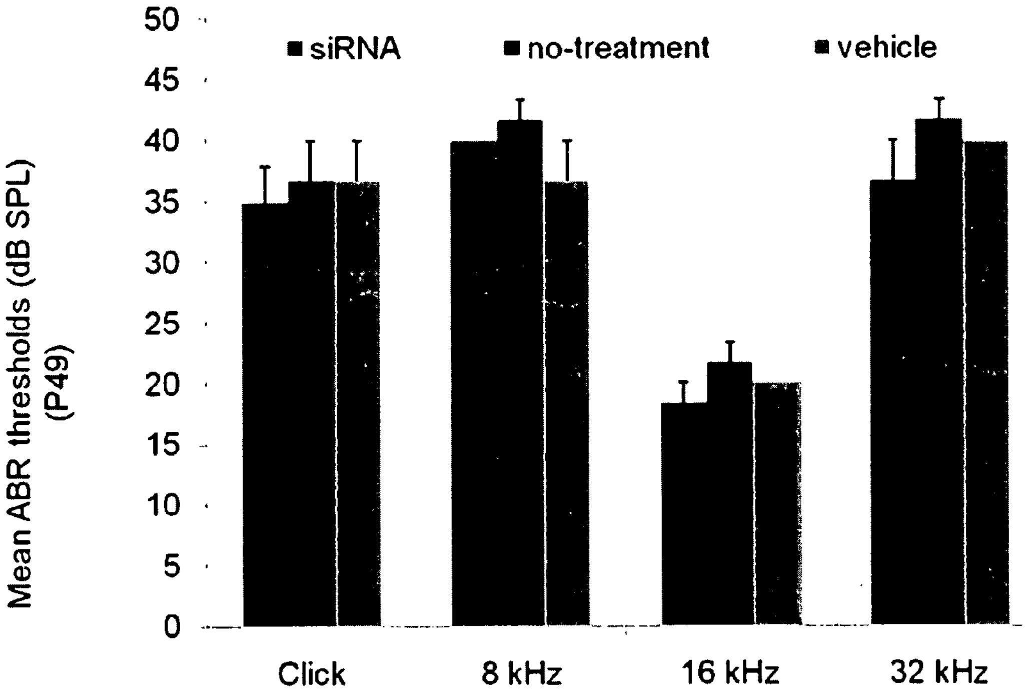
FIG. 3 is a bar graph showing that weekly treatment with dsRNA or vehicle ear drops to the inner ear does not affect hearing function in wild type mice.

FIG. 3 shows that weekly treatment with dsRNA or vehicle ear drops to the inner ear of wild type mice does not affect hearing function, as assessed by ABR thresholds. For each KHz measurement, the results for siRNA treated animals are on the left, untreated animals are in the center and vehicle treated animals are on the right.

Study 2: Pilot evaluation therapeutic effect of four dsRNA molecules targeting four different genes, CASP2, NOX3, CAPNS1 and RHOA, in male Phex$^{hyp\text{-}Duk}$/Y mice Study objectives: Assessment of efficacy of dsRNA test molecules in mouse genetic model of Ménière's disease by using functional and histological evaluation.

Figure 4A:
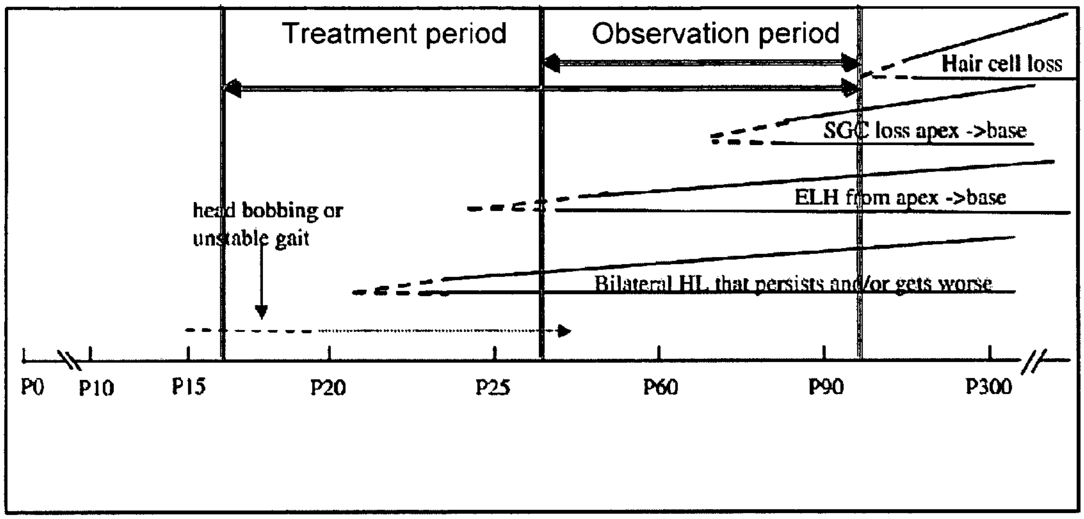
FIGS. 4A and 4B show experimental design to test efficacy of test molecules in preserving hearing function in the murine model of Ménière's disease. (P15, P29, P90-days post partum; siRNA delivery prior to P15 is impossible because ear channel is closed; ABR measurement before P29-30 is technically impossible).
Figure 4B:
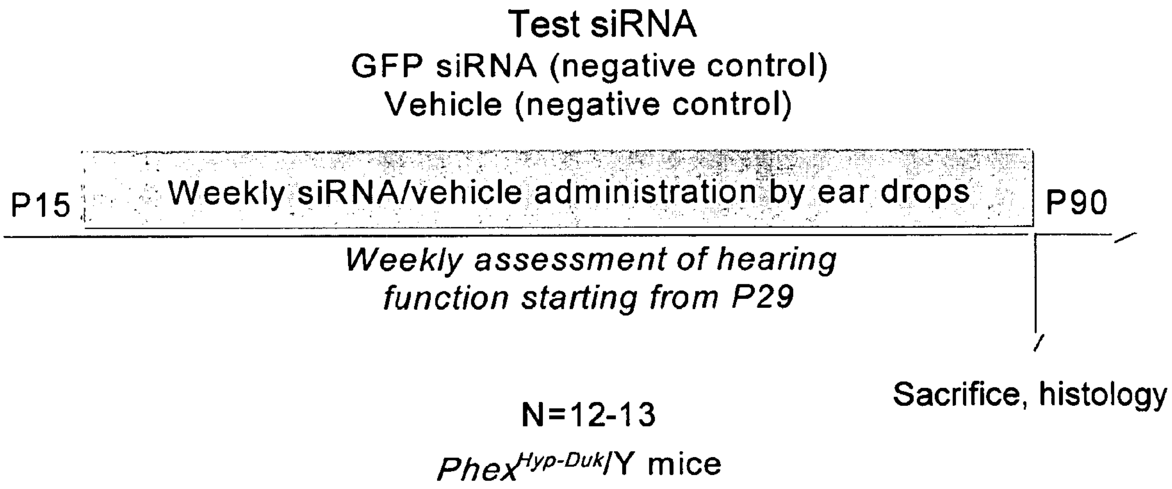

Study 2: The study design is shown in Table 3 and in FIGS. 4A and 4B. FIG. 4A shows the approximate timeline of events in the inner ear of Phex$^{hyp\text{-}Duk}$/Y. Dotted line indicates onset of phenotype, mild hearing loss (HL), signs of endolymphatic hydrops (ELH), spiral ganglion cell (SGC) degeneration, or hair cell degeneration, with some variability among animals in onset, appearance and severity. Solid line that follows dotted lines indicates that the phenotype is established with age. (from Hear Res. 2008 March; 237(1-2): 90-105).

TABLE 3

Study 2 design

| Group (n = 12) | Article | Treatment frequency | Functional tests | Termi-nation |
|---|---|---|---|---|
| 1 | siCASP2 (test 1) | P15, P22, P29, P36. P42, P49, P56, P63, P63, P70, P77, P84 | P29, P36. P42, P49, P56, P63, P63, P70, P77, P84, P90 | P90 |
| 2 | siNOX3 (test 2) | P15, P22, P29, P36. P42, P49, P56, P63, P63, P70, P77, P84 | P29, P36. P42, P49, P56, P63, P63, P70, P77, P84, P90 | P90 |
| 3 | siCAPNS (test 3) | P15, P22, P29, P36. P42, P49, P56, P63, P63, P70, P77, P84 | P29, P36. P42, P49, P56, P63, P63, P70, P77, P84, P90 | P90 |
| 4 | siRHOA (test 4) | P15, P22, P29, P36. P42, P49, P56, P63, P63, P70, P77, P84 | P29, P36. P42, P49, P56, P63, P63, P70, P77, P84, P90 | P90 |
| 5 | siCNL (negative control) | P15, P22, P29, P36. P42, P49, P56, P63, P63, P70, P77, P84 | P29, P36. P42, P49, P56, P63, P63, P70, P77, P84, P90 | P90 |
| 6 | Vehicle (negative control) | P15, P22, P29, P36. P42, P49, P56, P63, P63, P70, P77, P84 | P29, P36. P42, P49, P56, P63, P63, P70, P77, P84, P90 | P90 |
| 7 | Intact (negative control) | none | P29, P36. P42, P49, P56, P63, P63, P70, P77, P84, P90 | P90 |

dsRNA or vehicle was delivered on a weekly basis to 6 groups of 12 mice each starting from P15 and till P63. Functional tests were performed weekly on the day of test or control articles administration and prior to their administration. dsRNA administration requires animal immobilization (anesthesia) for 40-60 minutes optimization of the schedule of functional test performance requiring anesthesia was performed. Functional tests in intact non-treated mice of the same age served as baseline control.

Animals were added to study groups incrementally in the course of colony expansion.

Statistical analyses was performed to compare results of auditory, vestibular and behavioral tests between age-matched treated and control Phex$^{Hyp\text{-}Duk}$/Y mice. P<0.05 was considered a significant difference.

Upon termination, inner ears of mice were dissected, fixed, embedded in paraffin and sectioned to have representation of both auditory and vestibular compartments as well as of spiral ganglion. The slides were used for histological evaluation of inner ear morphology. The CASP2 dsRNA compound (CASP2 siRNA, designated as siCASP2, QPI1007 or 1007) that was used in the preparation of the pharmaceutical composition utilized in this study is a 19-nucleotide blunt-ended duplex having two separate strands, with an antisense strand (AS, guide strand) comprising unmodified ribonucleotides at positions 1, 3, 5, 7, 9, 10, 12, 14, 16 and 18 (capital letters), and 2'OMe sugar modified ribonucleotides at positions 2, 4, 6, 8, 11, 13, 15, 17 and 19 (lower case letters); and a sense strand (SEN, passenger strand) comprising unmodified ribonucleotides and an L-deoxyribonucleotide at position 18 (bold underlined) and an inverted deoxyriboabasic moiety (iB) at the 5' terminus, as depicted:

SEN (SEQ ID NO: 26)

5' iB-GCCAGAAUGUGGAACUCCU 3'

AS (SEQ ID NO: 27)

3' cGgUcUuAcACcUuGaGgA 5'

The NOX3 dsRNA compound (siNOX3_4) is a 19-nucleotide blunt-ended duplex (human, mouse, rat cross-species) having two separate strands, with an antisense strand (AS, guide strand) comprising unmodified ribonucleotides at positions 2, 4, 6, 8 10, 12, 14, 16 and 18 (capital letters), and 2'OMe sugar modified ribonucleotides at positions 1, 3, 5, 7, 9, 11, 13, 15, 17 and 19 (lower case letters); and a sense strand (SS, passenger strand) comprising 2'OMe sugar modified ribonucleotides at positions 2, 4, 6, 8 10, 12, 14, 16 and 18 (lower case letters), and unmodified ribonucleotides at positions 1, 3, 5, 7, 9, 11, 13, 15, 17 and 19 (upper case letters). The 3' terminus of the sense strand and the 3' terminus of the antisense strand are non-phosphorylated.

siNOX3_4

SS (SEQ ID NO: 10)

5' UcCuGgAaCuUcAcAuGaA 3'

AS (SEQ ID NO: 11)

3' aGgAcCuUgAaGuGuAcUu 5'

The CAPNS1 dsRNA compound (siCAPNS1_13) is a 19-nucleotide blunt-ended duplex having two separate strands, with an antisense strand (AS, guide strand) comprising unmodified ribonucleotides at positions 2, 4, 6, 8 10, 12, 14, 16 and 18 (capital letters), and 2'OMe sugar modified ribonucleotides at positions 1, 3, 5, 7, 9, 11, 13, 15, 17 and 19 (lower case letters); and a sense strand (SS, passenger strand) comprising 2'OMe sugar modified ribonucleotides at positions 2, 4, 6, 8 10, 12, 14, 16 and 18 (lower case letters), and unmodified ribonucleotides at positions 1, 3, 5, 7, 9, 11, 13, 15, 17 and 19 (upper case letters);

siCAPNS1_13

SS (SEQ ID NO: 12)

5' GcUaCaGaAcUcAuGaAuA 3'

AS (SEQ ID NO: 13)

3' cGaUgUcUuGaGuAcUuAu 5'

The RHOA dsRNA compound (siRHOA 4) is a 19-nucleotide blunt-ended duplex having two separate strands, with an antisense strand (AS, guide strand) comprising unmodified ribonucleotides at positions 2, 4, 6, 8 10, 12, 14, 16 and 18 (capital letters), and 2'OMe sugar modified ribonucleotides at positions 1, 3, 5, 7, 9, 11, 13, 15, 17 and 19 (lower case letters); and a sense strand (SS, passenger strand) comprising 2'OMe sugar modified ribonucleotides at positions 2, 4, 6, 8 10, 12, 14, 16 and 18 (lower case letters), and unmodified ribonucleotides at positions 1, 3, 5, 7, 9, 11, 13, 15, 17 and 19 (upper case letters);

siRHOA_4

SS (SEQ ID NO: 14)

5' GcCaCuUaAuGuAuGuUaC 3'

AS (SEQ ID NO: 15)

3' cGgUgAaUuAcAuAcAaUg 5'

The EGFP (enhanced green fluorescent protein) control dsRNA compound (siEGFP_5) is a 19-nucleotide blunt-ended duplex having two separate strands, with an antisense strand (AS, guide strand) comprising unmodified ribonucleotides at positions 2, 4, 6, 8 10, 12, 14, 16 and 18 (capital letters), and 2'OMe sugar modified ribonucleotides at positions 1, 3, 5, 7, 9, 11, 13, 15, 17 and 19 (lower case letters); and a sense strand (SS, passenger strand) comprising 2'OMe sugar modified ribonucleotides at positions 2, 4, 6, 8 10, 12, 14, 16 and 18 (lower case letters), and unmodified ribonucleotides at positions 1, 3, 5, 7, 9, 11, 13, 15, 17 and 19 (upper case letters);

siEGFP_5

SS (SEQ ID NO: 16)

5' GgCuAcGuCcAgGaGcGcAcC 3'

AS (SEQ ID NO: 17)

3' cCgAuGcAgGuCcUcGcGuGg 5'

RESULTS AND CONCLUSIONS

Figure 5A:
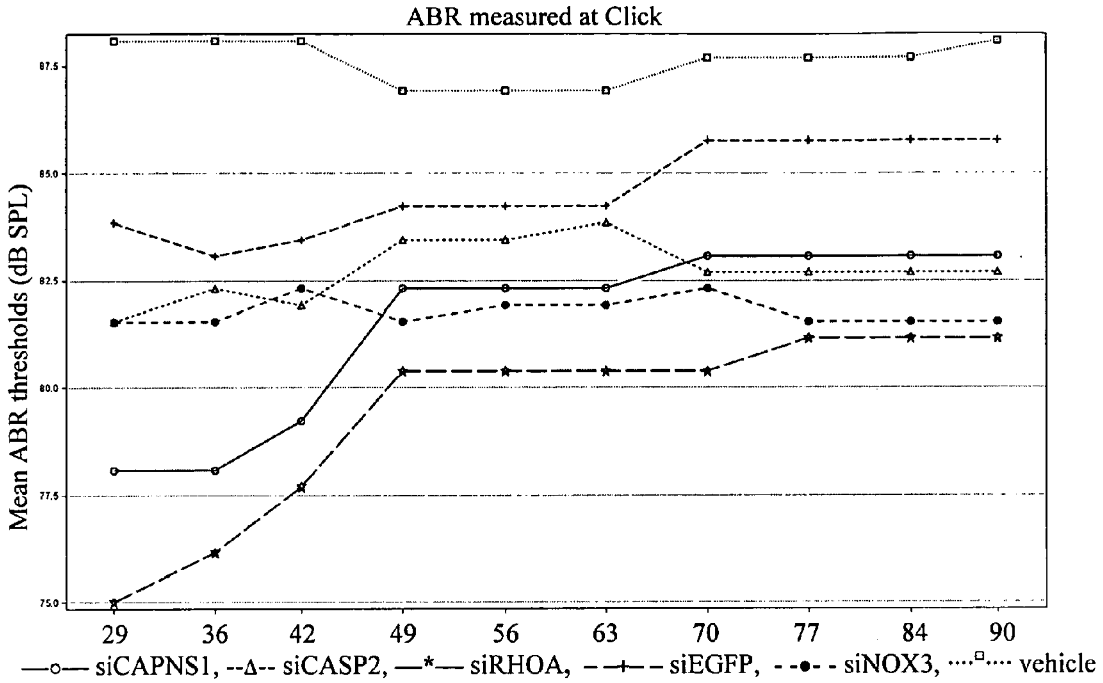
FIGS. 5A-5D show time course analysis of hearing function (ABR) in negative control (vehicle-treated or siEGFP-treated) or siRNA-treated Phex$^{hyp-Duk}$/Y mice. Data on the graphs show Auditory-evoked brainstem response (ABR) thresholds (db) at specified test sound frequency (kHz).
Figure 5B:
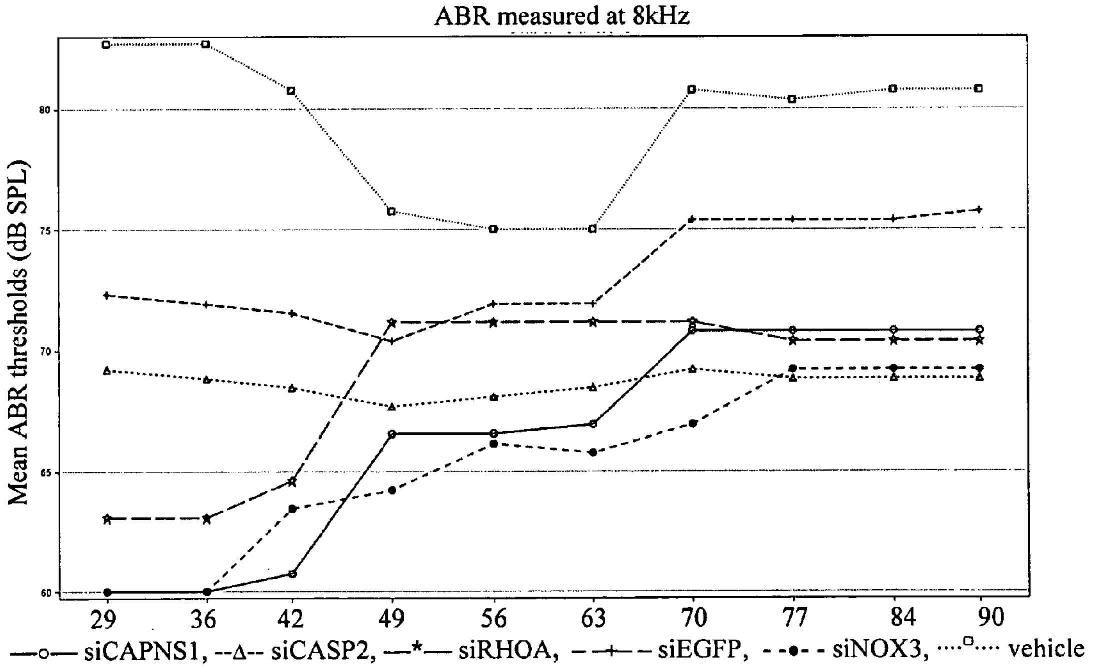
Figure 5C:
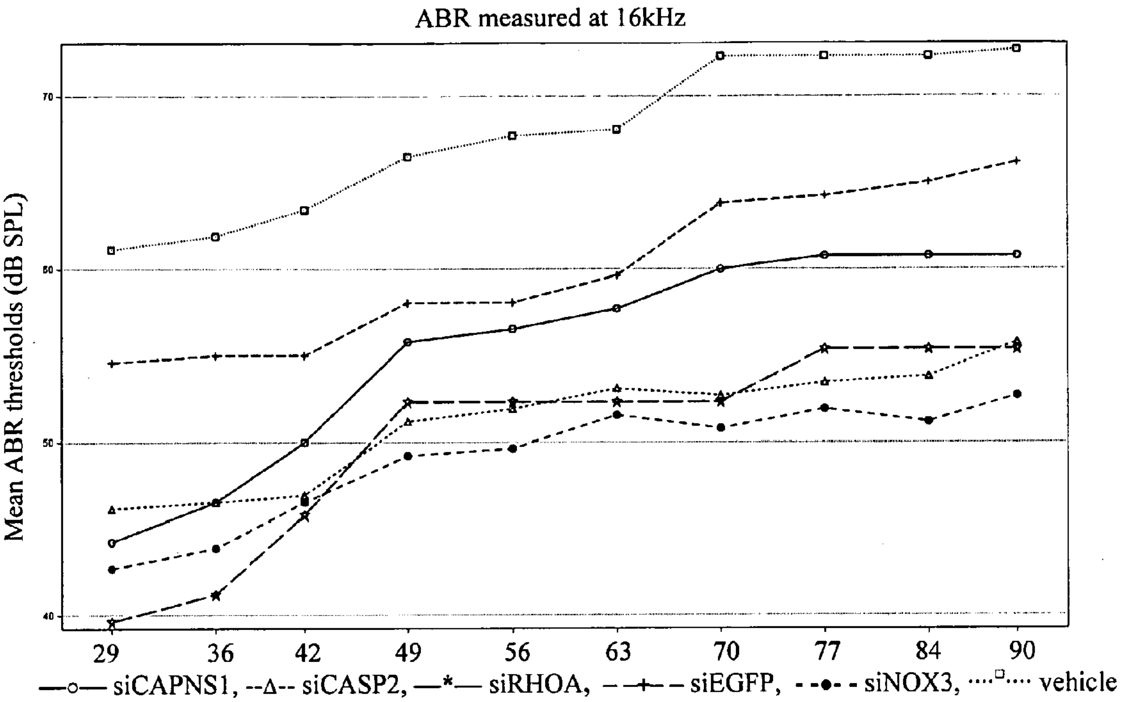
Figure 5D:
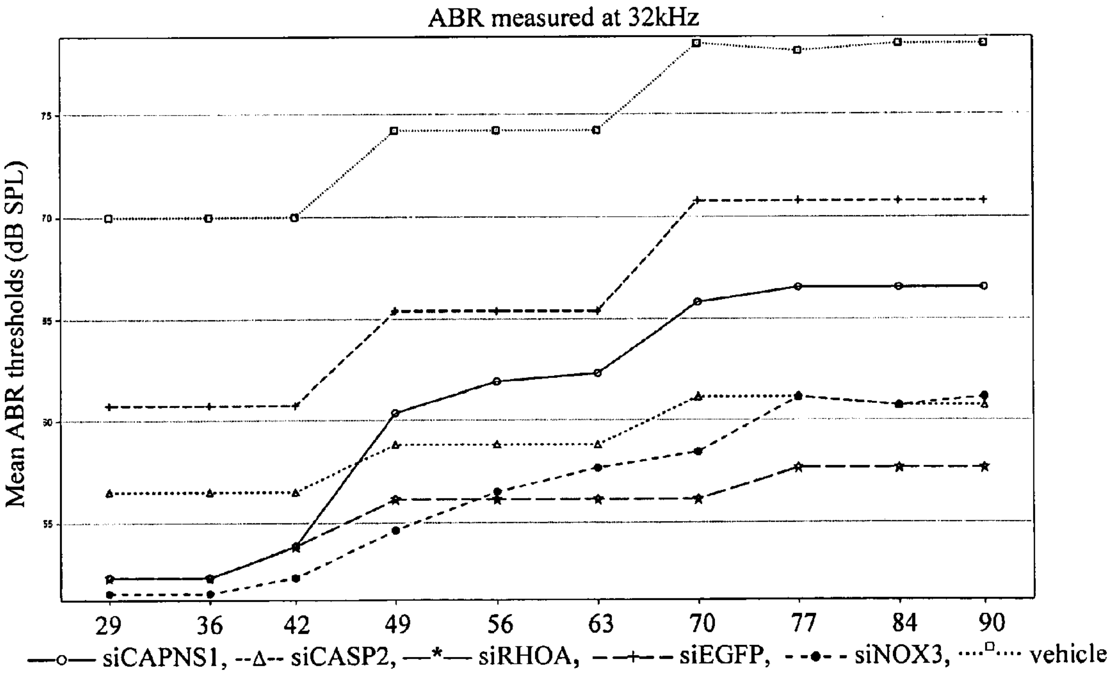
Figure 5E:
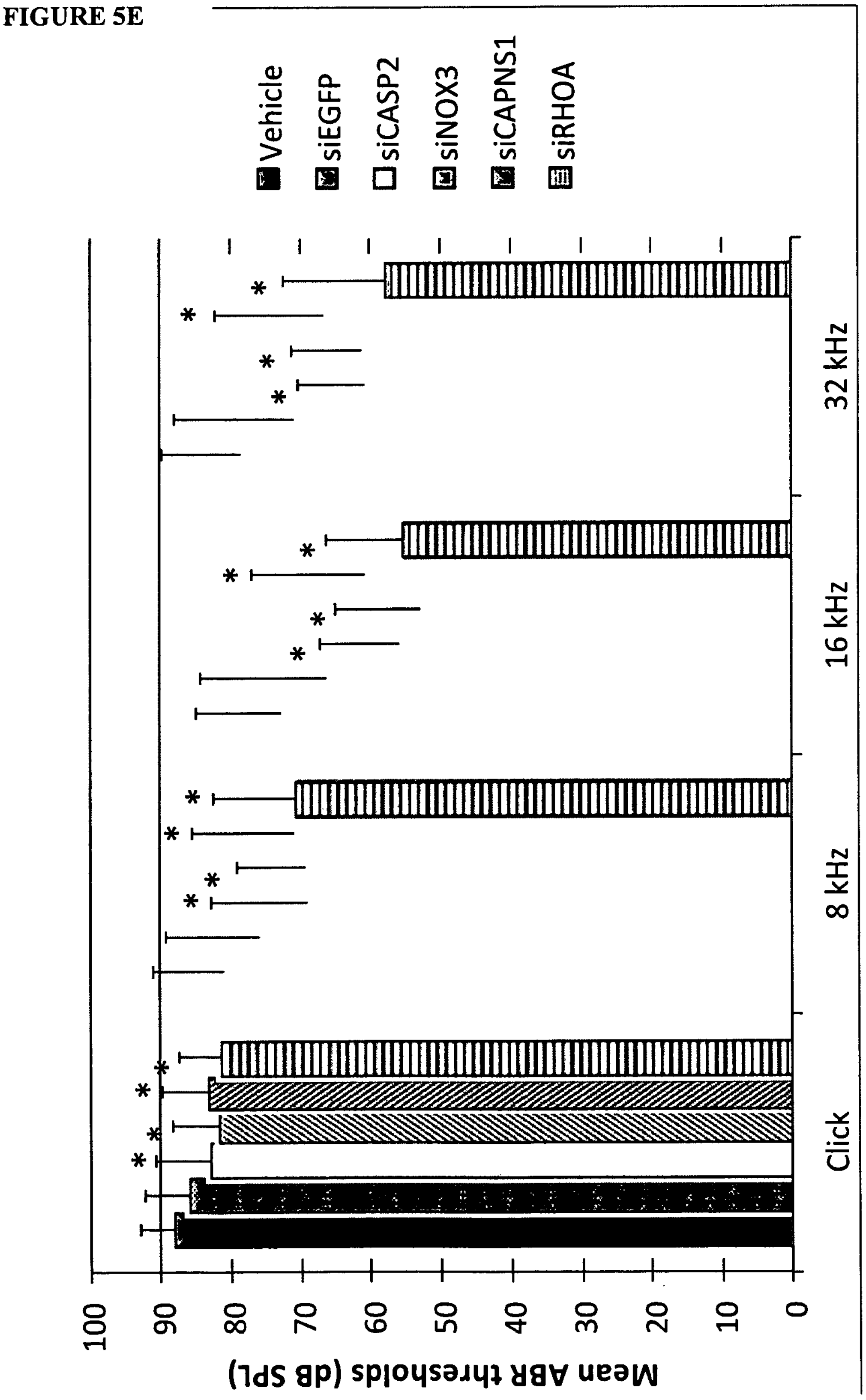
FIG. 5E is a bar graph showing relative improvement in ABR at P90 in siRNA treated animals compared to vehicle-treated and siEGFP-treated animals.

Results of ABR functional test: Phex$^{hyp\text{-}Duk}$/Y mice display significant loss of hearing at all frequencies. The major loss of hearing function occurs before P29 when systematic measurements started and there was a trend for further deterioration in negative control groups but not in the siRNA treated groups. Already at P29, hearing function in siRNA-treated mice (2 treatments on P15 and P22) appear significantly better than in vehicle-treated mice at all frequencies and this difference in favor of siRNA-treated mice became more profound with time. Starting from P70, hearing function at 16-32 kHz became significantly better in all siRNA treated group compared to siEGFP-treated animals. ABR results at day P90 are shown in FIG. 5E. In all FIGS. 5A-5D, a dotted line with open squares represent vehicle; short dashes dashed line with open triangles represents siCASP2 treated animals; medium dashes dashed line with plus sign ("+") represents siEGFP treated animals; medium dashes dashed line with closed circles represents siEGFP treated animals; long dashes dashed line with stars represents siRHOA treated animals; a solid line with open circles represents siCAPNS1 treated animals. The x-axis provides weekly test days from P29-P90 and the y-axis provides dB readings from ABR test. The y-axis is a different scale in the four tests, Click is ~75-87.5 dB, 8 KHz is ~60-80, 16 KHz is ~40-70 and 32 KHz is ~55-75.

FIG. 5E shows improvement in ABR at day P90 in animals treated with test compounds. There is no statistically significant difference between vehicle and siEGFP. ABR for normal mice at Click: 55 dB; at 8 kHz: 40 dB; 16 kHz: 35 dB, at 32 kHz 40 dB.

Conclusions: Phex$^{hyp\text{-}Duk}$/Y mice showed hearing function protection in the siCASP2, siCAPNS1, siNOX3 and siRHOA treated groups. Histology verified neuroprotection of the spiral ganglia and vestibular ganglia neurons.

Figures 6A, 6B, 6C, 6D, 6E, 6F:
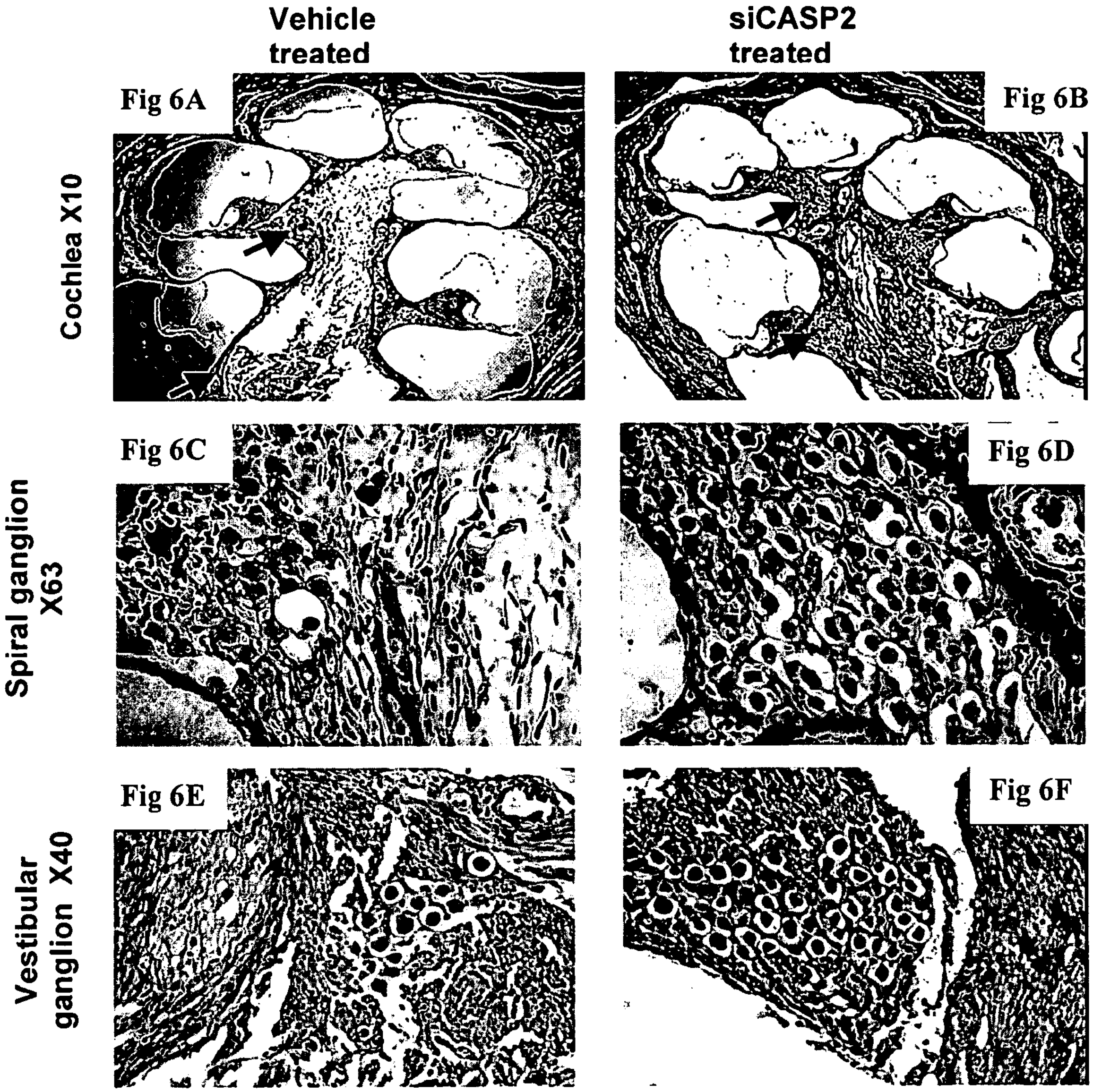
FIGS. 6A-6F show histological evaluation of the inner ear neurons of Phex$^{hyp-Duk}$/Y mice and the significant neuroprotection of spiral and vestibular ganglions provided by siCASP2 (1007). Arrows in FIGS. 6A and 6B show spiral ganglion (SG).
Figure 7A:
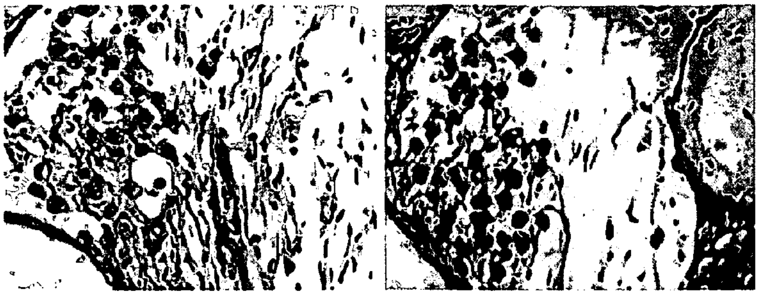
FIGS. 7A-7D show histological evaluation of the inner ear neurons of Phex$^{hyp-Duk}$/Y mice and the significant neuroprotection of spiral ganglions provided by siCAPNS1 (FIG. 7B), siNOX3 (FIG. 7C) and siRHOA (FIG. 7D) compared to vehicle-treated and siEGFP-treated animals (FIG. 7A).
Figure 7B:
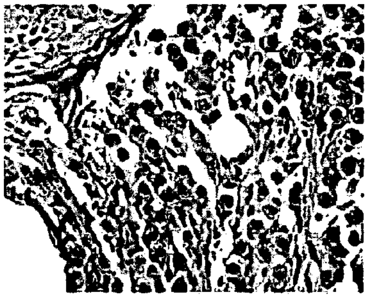
Figure 7C:
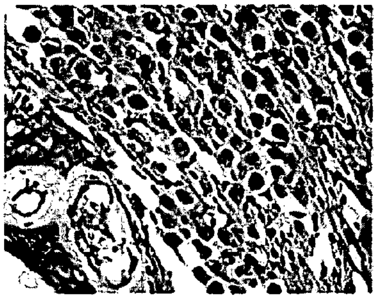
Figure 7D:
Figure 8A:
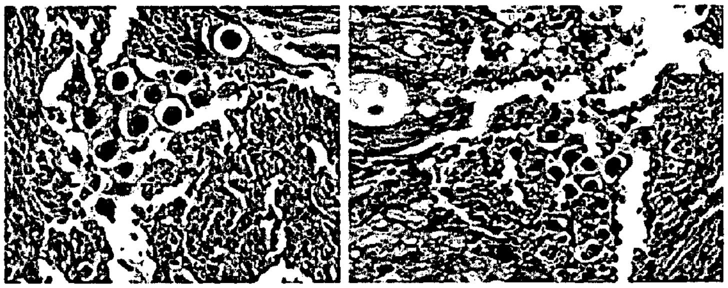
FIGS. 8A-8D show histological evaluation of the inner ear neurons of Phex$^{hyp-Duk}$/Y mice and the significant neuroprotection of vestibular ganglions provided by siCAPNS1 (FIG. 8B), siNOX3 (FIG. 8C) and siRHOA (FIG. 8D) compared to vehicle-treated and siEGFP-treated animals (FIG. 8A).
Figure 8B:
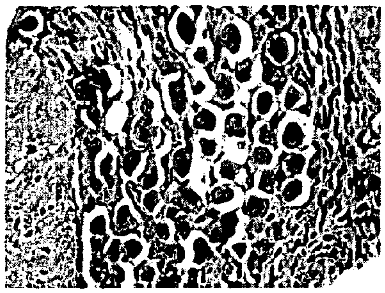
Figure 8C:
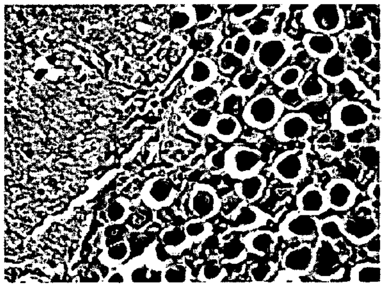
Figure 8D:
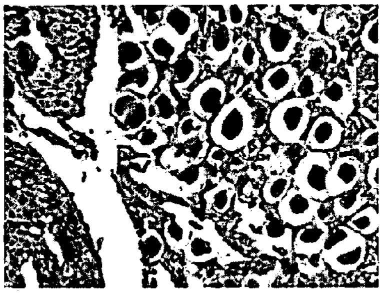
Figure 9A:
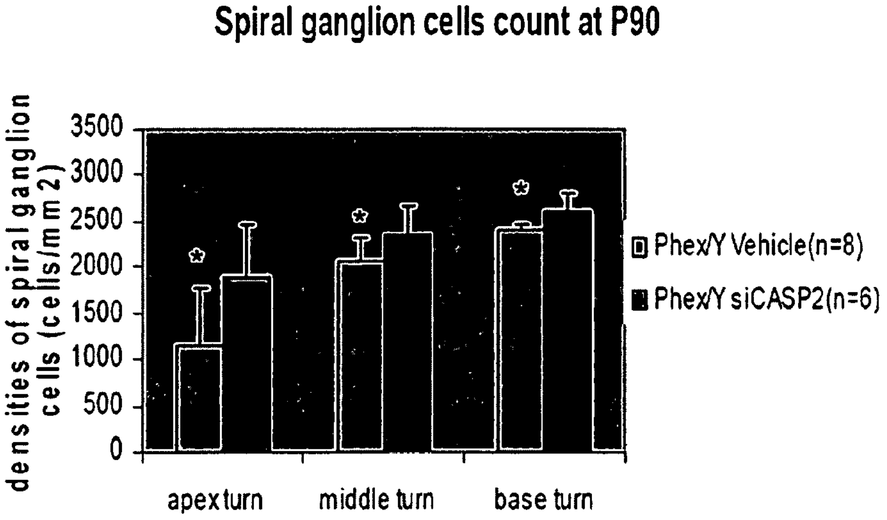
FIGS. 9A and 9B show protection of spiral ganglion cells at P90 in siCASP2-treated ears.
Figure 9B:
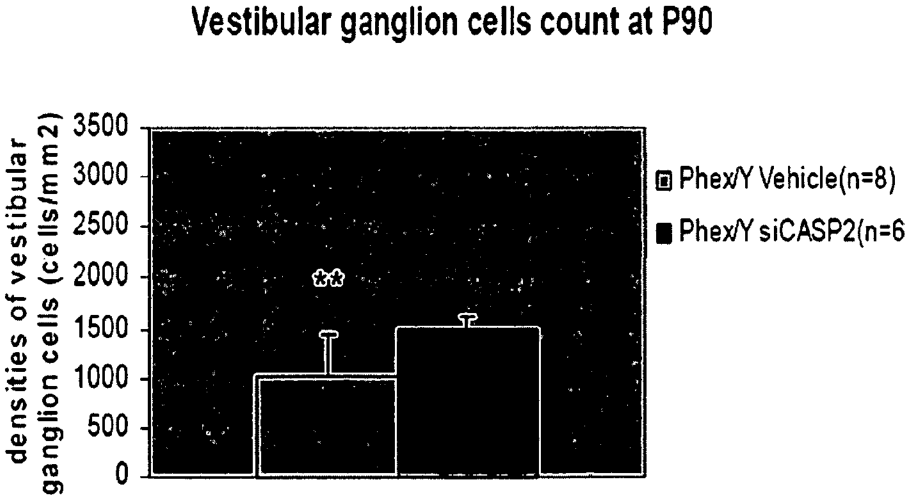

Results of histological staining: Histological analysis of the inner ear sections prepared from all mice at study termination demonstrated substantial and significant preservation of the spiral and vestibular ganglia cells in the siRNA treated mice compared to controls. ELH (Endolymphatic hydrops) phenotype, typical for this model, was not influenced by siRNA treatment. As expected, at this stage of the disease (P90), no changes in sensory epithelia were observed in all study groups. Spiral ganglion cells and vestibular ganglion cells showed significant protection from apoptotic death in dsRNA treated ears of Phex$^{hyp\text{-}Duk}$/Y mice compared to vehicle-treated group. Compare FIGS. 6B to 6A, 6D to 6C and 6F to 6E. Black (distorted tissue) show regions of ganglia cell death in FIG. 6A and regions of dense ganglia in FIG. 6B. Cochlear hair cells and vestibular hair cells appear non-affected in the model and treatment with siCASP2 produced no additional effects compared to control. Similar results were obtained with siCAPNS1, siNOX3 and siRHOA treated animals. FIG. 7A shows ganglia cells in the cochlear apex turn from vehicle-treated (left panel) or siEGFP-treated (right panel) Phex$^{hyp\text{-}Duk}$ mutant mice. FIGS. 7B, 7C and 7D show ganglia cells in the cochlear apex turn from siCAPNS1-, siNOX3- and siRHOA-treated animals, respectively. All magnifications are x63. FIG. 8A shows vestibular ganglia cells from vehicle-treated (left panel) or siEGFP-treated (right panel) Phex$^{hyp\text{-}Duk}$ mutant male mice. FIGS. 8B, 8C and 8D show vestibular ganglia cells in the from siCAPNS1-, siNOX3- and siRHOA-treated animals, respectively. All magnifications are x63. Survival of the spiral ganglion cells is a critical factor in preservation of hearing.

The dsRNA delivery in this study, in mice, was achieved by eardrop application. In a clinical setting, transtympanic injection of drugs is clinically routine and use of eardrops for delivery of dsRNA is possible. Furthermore, the dsRNA utilized in the studies disclosed herein are merely non-limiting examples of dsRNA that down regulate CASP2, NOX3, CAPNS1 and RHOA, and dsRNA species having different sequences and structures that are active in down regulating their respective genes are useful in practicing the methods and kits disclosed herein.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the removed material is specifically recited herein. Other embodiments are within the following claims.

The invention claimed is:

1. A method of treating Ménière's disease in a subject in need thereof, the method comprising administering to the subject's ear a double-stranded RNA (dsRNA) compound that down-regulates expression of a Caspase 2, Apoptosis-Related Cysteine Peptidase (CASP2) gene, wherein the CASP2 gene encodes an mRNA having a sequence set forth in any one of SEQ ID NO:1-3, in an amount effective to provide neuroprotection to a neuron in a spiral ganglion or a vestibular ganglion in the subject's ear.

2. The method of claim 1, wherein the dsRNA compound is formulated as a pharmaceutically acceptable salt of the compound.

3. The method of claim 1, wherein the neuron is in comprised within, a spiral ganglion.

4. The method of claim 1, wherein the neuron is in a vestibular ganglion.

5. The method of claim 1, wherein the neuroprotection comprises protecting the neuron from cell death.

6. The method of claim 5, wherein cell death of the neuron comprises apoptotic cell death.

7. The method of claim 1, wherein the neuroprotection comprises an improvement of cochlear function or of vestibular function, or of both cochlear and vestibular function.

8. The method of claim 1, wherein the dsRNA compound has the structure:

```
                        (sense strand, SEQ ID NO: 24)
5' z"-GCCAGAAUGUGGAACUCCU-Z' 3'

                    (antisense strand, SEQ ID NO: 25)
3' Z-CGGUCUUACACCUUGAGGA 5'
```

wherein each A, C, U, and G is an unmodified or modified ribonucleotide or an unconventional moiety and each consecutive ribonucleotide or unconventional moiety is joined to the next ribonucleotide or unconventional moiety by a phosphodiester bond;

wherein the sense strand comprises, counting from the 5' terminus, an unmodified ribonucleotide at positions 1, 2, 3, 4, 5, 6, 7, 8, 9, 10, 11, 12, 13, 14, 15, 16, 17, and 19, and a L-deoxycytidine at position 18 (set forth in SEQ ID NO:24);

wherein the antisense strand comprises, counting from the 5' terminus, a 2'-O-methyl sugar modified ribonucleotide at each one of positions 2, 4, 6, 8, 11, 13, 15, 17, and 19, and an unmodified ribonucleotide at each of positions 1, 3, 5, 7, 9, 10, 12, 14, 16, and 18 (set forth in SEQ ID NO:25);

wherein z" is covalently attached to the 5' terminus of the sense strand (set forth in SEQ ID NO:26) and comprises an inverted deoxyabasic moiety; and wherein Z and Z' are both absent.

9. The method of claim 1, wherein the dsRNA molecule is formulated for transtympanic administration.

10. The method of claim 1, wherein the dsRNA molecule is formulated as eardrops.

11. The method of claim 1, wherein the subject is a mammal.

12. The method of claim 11, wherein the subject is a human.

13. The method of claim 1, wherein multiple neurons are protected from cell death in both the spiral ganglion and the vestibular ganglion.

14. The method of claim 1, wherein the subject has symptoms comprising fluctuating hearing loss and any one or more of vertigo, endolymphatic hydrops, nausea, and tinnitus.

* * * * *